(12) United States Patent
Herold et al.

(10) Patent No.: US 8,497,245 B2
(45) Date of Patent: Jul. 30, 2013

(54) TRYPSIN-LIKE SERINE PROTEASE INHIBITORS, THEIR PREPARATION AND USE AS SELECTIVE INHIBITORS OF THE CLOTTING FACTORS IIA AND XA

(75) Inventors: Peter Herold, Muenchenstein (CH); Stjepan Jelakovic, Freiburg (DE); Mohammed Daghish, Leipzig (DE); Claudia Reichelt, Leipzig (DE); Alexander Schulze, Bad Liebenwerda (DE); Andrea Schweinitz, Jena (DE); Friedrich-Alexander Ludwig, Leipzig (DE); Adel Rafai Far, Kirkland (CA); Ting Kang, Mount-Royal (CA)

(73) Assignee: The Medicines Company (Leipzig) GmbH, Leipzig (DE)

( * ) Notice: Subject to any disclaimer, the term of this patent is extended or adjusted under 35 U.S.C. 154(b) by 0 days.

(21) Appl. No.: 13/332,900

(22) Filed: Dec. 21, 2011

(65) Prior Publication Data

US 2012/0252743 A1 Oct. 4, 2012

Related U.S. Application Data

(60) Provisional application No. 61/425,597, filed on Dec. 21, 2010.

(51) Int. Cl.
*A61K 38/05* (2006.01)
(52) U.S. Cl.
USPC ......... 514/13.7; 514/14.3; 514/16.4; 514/183
(58) Field of Classification Search
None
See application file for complete search history.

(56) References Cited

U.S. PATENT DOCUMENTS

| | | | |
|---|---|---|---|
| 5,914,319 | A | 6/1999 | Schacht et al. |
| 6,831,196 | B2 | 12/2004 | Stürzebecher et al. |
| 6,841,701 | B2 | 1/2005 | Stürzebecher et al. |
| 7,402,586 | B2 | 7/2008 | Lu et al. |
| 7,772,251 | B2 | 8/2010 | Stürzebecher et al. |
| 7,838,560 | B2 | 11/2010 | Stürzebecher et al. |
| 8,124,587 | B2 | 2/2012 | Steinmetzer et al. |
| 8,207,378 | B2 | 6/2012 | Steinmetzer et al. |
| 2006/0148901 | A1 | 7/2006 | Stürzebecher et al. |
| 2007/0066539 | A1 | 3/2007 | Stürzebecher et al. |
| 2009/0117185 | A1* | 5/2009 | Steinmetzer et al. ......... 424/474 |
| 2011/0002992 | A1 | 1/2011 | Stürzebecher et al. |
| 2011/0065799 | A1 | 3/2011 | Stürzebecher et al. |

FOREIGN PATENT DOCUMENTS

| | | |
|---|---|---|
| WO | 02/059065 | 8/2002 |
| WO | WO-2004/000310 A1 | 12/2003 |
| WO | WO-2004/000818 A1 | 12/2003 |
| WO | 2012/004678 | 1/2012 |

OTHER PUBLICATIONS

U.S. Appl. No. 13/471,007, filed May 14, 2012, Steinmetzer et al.

(Continued)

*Primary Examiner* — Cecilia J Tsang
*Assistant Examiner* — Fred Reynolds
(74) *Attorney, Agent, or Firm* — Clark & Elbing LLP

(57) ABSTRACT

The invention provides methods of making and using compounds of the formula:

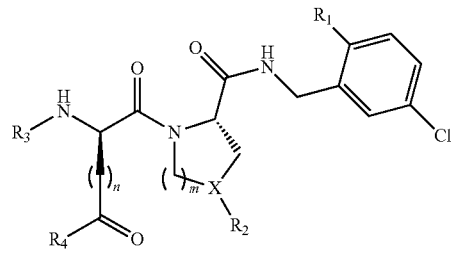

or a pharmaceutically acceptable salt thereof; wherein n is an integer between 1 and 2 inclusively; m is an integer between 0 and 2 inclusively; X is selected from the group consisting of CH or N; $R_1$ is selected from the group consisting of —$CH_2NH_2$, and

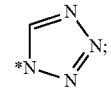

$R_2$ is selected from the group consisting of —H, —OH, —$NH_2$ and acetyl; $R_3$ is selected from the group consisting of —H, benzyloxycarbonyl and benzylsulfonyl; and $R_4$ is selected from the group consisting of —OH,

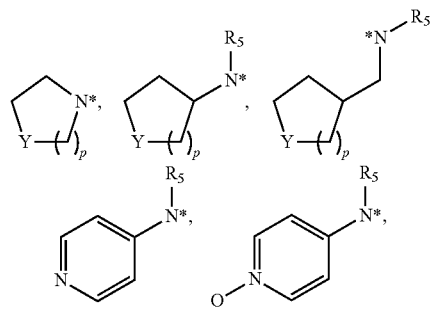

wherein p is an integer between 0 and 2 inclusively, Y is selected from the group consisting of —O—, —S—, —S(═O)—, —$SO_2$—, methylene, —CH(OH)—, —CH($NH_2$)—, —CH($CH_2$—OH)—, —CH($CH_2$—$NH_2$)— or —N($R_6$)—, $R_5$ is selected from the group consisting of —H or a simple ($C_1$-$C_3$) alkyl and $R_6$ is selected from the group consisting of —H, a simple ($C_1$-$C_3$) alkyl or a simple ($C_1$-$C_3$) acyl. These compounds are useful as anticoagulant agents as a result of their selective dual inhibition of thrombin and prothrombinase.

12 Claims, No Drawings

OTHER PUBLICATIONS

International Search Report and Written Opinion issued in corresponding International Application No. PCT/CA2011/001398, mailed Apr. 5, 2012.

Deng et al., "Development of an oxazolopyridine series of dual thrombin/factor Xa inhibitors via structure-guided lead optimization," *Bioorg. Med. Chem. Lett.* 13: 4411-4416 (2005).

Kishimoto et al., "MII8—A rationally engineered low-molecular-weight heparin designed specifically for the treatment of acute coronary syndromes," *Thromb. Haemost.* 102: 900-906 (2009).

Maryanoff et al., "Exploration of Potential Prodrugs of RWJ-445167, an Ozyguanidine-based Dual Inhibitor of Thrombin and Factor Xa," *Chem. Biol. Drug Des.* 68: 29-36 (2006).

Petitou et al., "From heparin to EP217609: The Long way to a new pentasaccharide-based neutralisable anticoagulant with an unprecedented pharmacological profile," *Thromb. Haemost.* 102: 804-810 (2009).

Ries et al., "Heterocyclic Thrombin Inhibitors. Part 2: Quinoxalinone Derivatives as Novel, Potent Antithrombotic Agents," *Bioorg. Med. Chem. Lett.* 13;2297-2302 (2003).

* cited by examiner

TRYPSIN-LIKE SERINE PROTEASE INHIBITORS, THEIR PREPARATION AND USE AS SELECTIVE INHIBITORS OF THE CLOTTING FACTORS IIA AND XA

CROSS-REFERENCE TO RELATED APPLICATIONS

This application claims benefit of U.S. Provisional Application No. 61/425,597, filed on Dec. 21, 2010, which is hereby incorporated by reference in its entirety.

FIELD OF THE INVENTION

The invention relates to the fields of organic chemistry, serine proteases (particularly thrombin and Factor Xa), thrombosis and hemostasis, and to the therapeutic modulation of blood coagulation.

BACKGROUND OF THE INVENTION

Thrombin and factor Xa are key enzymes of blood coagulation. Factor Xa (FXa) is activated from its precursor, factor X, by either the intrinsic tenase complex (factor IXa/factor VIIIa) or the extrinsic tenase complex (tissue factor/FVIIa). Factor Xa activates prothrombin to thrombin, a reaction that is enhanced 400,000-fold when FXa is incorporated into the prothrombinase complex consisting of factor Va, calcium and phospholipids. Thrombin catalyzes the conversion of fibrinogen to fibrin and activates platelets both of which results in the formation of blood clots. Thrombin has additional functions both within and outside the coagulation system. By activating factors VIII, V, and XI, thrombin amplifies its own generation whereas protein C activation by thrombin contributes to the downregulation of coagulation. Activation of factor XIII as well as the thrombin activatable fibrinolysis inhibitor (TAFI) by thrombin affect the fibrinolytic system and contribute to clot stabilization, and several cellular and inflammatory functions of thrombin are mediated mainly via binding to the protease-activated receptors.

Both thrombin and factor Xa are validated targets for anticoagulant therapies. The majority of anticoagulant drugs in clinical use have anti-thrombin or anti-FXa activity, or both. Direct thrombin inhibition attenuates fibrin formation, thrombin-mediated activation of factors V, VIII, XI and XIII, and thrombin-induced platelet activation and aggregation.

Factor Xa has become an attractive target for antithrombotic therapy because of its position upstream of thrombin in the sequence of coagulation reactions. The fact that activation of one factor Xa molecule results in the generation of 1000 molecules of thrombin suggests that small amounts of a factor Xa inhibitor can effectively block thrombin generation without the need for high systemic levels of antithrombotic drug concentrations while low levels of thrombin remain active to ensure primary hemostasis and other functions of thrombin. Selective factor Xa inhibition has been shown in numerous animal studies to provide antithrombotic efficacy with little or no effect on markers of primary hemostasis (Leadley et al., Curr. Top. Med. Chem. 1, 151-159, 2001).

Heparin targets multiple enzymes in the coagulation cascade including thrombin and factor Xa. It has been the mainstay of antithrombotic therapy for more than 60 years but its use is associated with a number of disadvantages. Limitations of heparin result from its indirect, antithrombin (AT)-dependent mode of inhibition as well as from non-specific binding to plasma proteins and cells. Low molecular heparins (anti-Xa and anti-thrombin activity) and the sulfated pentasaccharides (selective anti-Xa agents) lack do not display the same nonspecific binding affinities and have replaced unfractionated heparin in some clinical settings. However, it has been demonstrated that clot-associated thrombin and prothrombinase contribute to thrombus growth and thrombin generation (Orfeo et al., J. Biol. Chem. 283, 9776-9786, 2008 and Brufatto et al., J. Thromb. Haemost. 1, 1258-1263, 2003), but are protected against AT-dependent anticoagulants like heparin, LMWHs, and pentasaccharides (Weitz et al., J Clin. Invest. 86, 385-391, 1990).

Small molecule direct inhibitors that simultaneously target thrombin and factor Xa have the potential to attenuate thrombin generation and thrombin activity more effectively than AT-dependent anticoagulants. The concept of dual inhibition of thrombin and factor Xa is also supported by the findings of Gould et al. (J Thromb. Haemost. 4, 834-841; 2010) demonstrating a synergistic antithrombotic effect of combining low doses of a direct thrombin inhibitor and a direct factor Xa inhibitor in vitro and in an animal model of thrombosis. Since bleeding time was not increased compared to the additive effect of each drug alone, the authors suggest that direct inhibition of multiple coagulation enzymes may provide an improved efficacy-to-safety ratio. Results from a study comparing unfractionated heparin, LMWH, a pentasaccharide, and a direct selective factor Xa inhibitor in vitro further support the concept that polytherapeutic agents are more effective anticoagulants than certain single-target agents in preventing surface-induced clot formation (Montalescot and Walenga, Clin. Appl. Thromb. Hemost. 15, 183-196, 2009).

During the past 10 years an increasing number of small molecule, selective factor Xa and thrombin inhibitors has been published and summarized in several review articles.

Several synthetic inhibitors of the active site of factor Xa have been disclosed. Two classes of inhibitors are to be distinguished: oral inhibitors and inhibitors for parenteral use. Xarelto (Rivaroxaban) with a Ki (against FXa) of 0.4 nM, (Perzborn et al., J Thromb Haemost 3:514-21, 2005), launched in 2008, and Apixaban with a Ki (against FXa) of 0.08 nM (BMS 652247, claimed in WO-03026652; April 2003; Apixaban, an oral, direct and highly selective factor Xa inhibitor: In vitro, antithrombotic and antihemostatic studies, Wong et al., J. Thromb. Haemostasis, 6, 820-829, 2008), are examples of oral anticoagulants in clinical use or in clinical development.

Similarly, synthetic inhibitors of the active site of thrombin (factor IIa), so-called direct thrombin inhibitors (DTI) have been disclosed, such as Exanta (Ximelagatran; Eriksson et al., J. Thromb. Haemost. 1, 2490-2496, 2003) with a Ki 2 nM, which has been withdrawn from the market in 2006, and Pradaxa (Dabigatran) with a Ki of 0.41 nM; first claimed in WO-9837075; Baetz and Spinler, Pharmacotherapy, 28, 1354-1373, 2008).

Argatroban is a small molecule DTI based on arginine, with Ki of 27-39 nM (Berry et al., Br. J. Pharmacol. 113, 1209-14, 1994). Examples of parenteral DTI in development are Melagatran (discontinued; Ki 1.3 nM), Flovagatran (Paion), or NU172 (Nuvelo) (Gross and Weitz, Clin Pharmacol Therapeut 86, 139-146, 2009; Weitz. Thromb. Haemost. 103, 62-70, 2010).

Similarly, there are selective direct FXa inhibitors in different stages of development such as Otamixaban (Guertin et al. Bioorg. Med. Chem. Lett. 12, 1671-1674, 2002) and selective peptidomimetic FXa inhibitors (Donneke et al., Bioorg. Med. Chem. Lett. 17, 3322-3329, 2007).

Stürzebecher et al. have described a series of N-terminal sulfonylated benzamidine peptidomimetics having various effects on serine proteases. Included within this class are factor Xa inhibitors, useful as anticoagulants and antithrombotics (U.S. Pat. No. 6,841,701); urokinase inhibitors, useful as tumor suppressors (US Pat. Application Publication No. 2005/0176993, U.S. Pat. No. 6,624,169); inhibitors of plasma kallikrein (PK), factor XIa and factor XIIa, useful as anticoagulants and antithrombotics (US Pat. Application Publication No. 2006/0148901); and matriptase inhibitors, useful as tumor suppressors (US Pat. Application Publication No. 2007/0055065). Clinical use of these inhibitors has not been reported.

A common feature of all these DTI and FXa inhibitors is their pronounced specificity of inhibition towards only one enzyme, either thrombin or FXa. Whereas unfractionated heparin (UFH) inhibits thrombin and FXa to similar extents, numerous FXa inhibitors and in particular sulfated glycosaminoglycans based on a reduction in the chain length as compared to low molecular weight heparin (LMWH), such as the clinically used Arixtra (Fondaparinux), Fragmin (Dalteparin) or Danaparoid present greater selectivity towards the inhibition of FXa (Eikelboom and Weitz, *Circulation*, 121, 1523-1532, 2010). Idrabiotaparinux, which is a modified fondaparinux with an antidote recognition moiety, is also an example of an indirect FXa inhibitor. In contrast to LMWH, fondaparinux and the mono-selective thrombin or FXa inhibitors, UFH indirectly inhibits not only thrombin and FXa, but also factors XIa and, to a lesser extent, XIIa and is thus effective in modulating the contact activation pathway. "This might explain in part why early attempts to use LMWH to prevent clotting in cardiac bypass circuits did not show any promise and why the risk of thrombosis of cardiac catheters is higher with fondaparinux than with UFH." (Hirsh et al., *Circulation* 116, 552-560, 2007).

In contrast to inhibitors with a pronounced mono specificity, the concept of a dual inhibitor bears attractive resemblance to natural inhibitors of coagulation, namely heparin which inhibits both thrombin and FXa and has equal activity against both enzymes. None of the drawbacks or adverse effects of heparin has been attributed to its multiple mode of inhibition. Moreover, its multi-target activity, also involving inhibition of contact phase proteases, might be an advantage in situations of blood contact with foreign surfaces without contributing to hemorrhagic effects. The ability of the newly developed monoselective synthetic FXa and thrombin inhibitors to reproduce the favorable effects and therapeutic profile of heparin has been questioned (Fareed et al., *Semin. Thromb. Hemost.* 34, 58-73, 2008). In major randomized trials, selective agents so far have not demonstrated superiority over UFH or LMWH with regard to ischemic endpoints suggesting that compounds with multiple sites of action, like UFH or LMWH, result in better ischemic outcome in patients with acute coronary syndrome (ACS) (Cohen, *Am. J Med.* 123, 103-110, 2010). Selective agents like the tissue factor/factor VIIa inhibitor rNAPc2 and the selective indirect FXa inhibitor fondaparinux, have shown insufficient antithrombotic activity in ACS patients undergoing PCI (Chan et al., *J Thromb. Thrombolysis* 28, 366-380, 2009). Increased incidence of catheter thrombosis with fondaparinux compared to UFH suggests that additional thrombin inhibition is required to prevent contact-mediated activation, a phenomenon that is even more relevant in cardiopulmonary bypass (CPB) surgery.

Data from a study comparing UFH, LMWH, fondaparinux and otamixaban in vitro support the concept that polytherapeutic agents, including UFH and enoxaparin, are more effective anticoagulants than certain single-target agents in preventing surface-induced clot formation (Montalescot and Walenga, *Clin. Appl. Thromb. Hemost.* 15, 183-196, 2009).

Dual inhibition of thrombin and FXa has the potential to effectively suppress thrombin generation and thrombin activity. A synergistic antithrombotic effect by simultaneous inhibition of thrombin and FXa has also been demonstrated in in vitro and animal models, and a ratio of anti-Xa/anti-thrombin activity of 2-3 has been found to be optimal with regard to efficacy and bleeding (Gould et al., *J. Thromb. Haemost.* 4, 834-841, 2006).

Tanogitran (Linz et al., WO 2004/000818; Ries et al., WO 2004/000310), which is characterized by an FXa/thrombin ratio of 0.1, RWJ445167 (Tianbao et al., U.S. Pat. No. 7,402,586; Maryanoff et al., *Chem. Biol. Drug Des.* 68:29-36, 2006)) with a ratio of <0.02, a series of oxazolopyridine based dual inhibitors (Deng et al., *Bioorg. Med. Chem. Lett.* 15, 4411-4416, 2005), and a series of quinoxalinone based dual inhibitors (Ries et al., *Bioorg. Med. Chem. Lett.* 13, 2297-2302, 2003) are dual thrombin/FXa inhibitors disclosed in the literature. There are also two products based on LMWH: M118 (Momenta; Kishimoto et al., *Thromb. Haemost.* 102, 900-906, 2009) and EP217609, (Endotis Pharma; Petitou, et al., *Thromb. Haemost.* 102, 804-810, 2009), both of which are equipotent against thrombin and FXa and share the specific feature that their action can be controlled by an antidote.

BRIEF DESCRIPTION OF THE INVENTION

It has been found that compounds of general formula I,

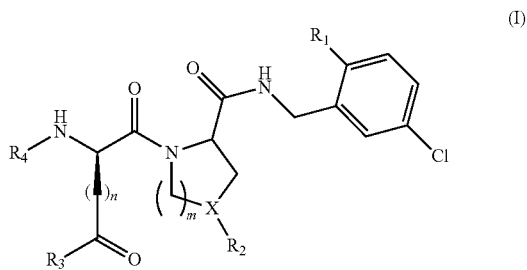

or a pharmaceutically acceptable salt thereof wherein X, $R_1$ to $R_4$, n, and m are as defined below, are effective and selective dual inhibitors of thrombin and factor Xa. The invention accordingly provides compounds of formula I, methods for the preparation of compounds of formula I, and pharmaceutical compositions comprising compounds of formula I. The invention also provides methods of inhibiting thrombin and factor Xa in a patient, methods for therapeutic modulation of the blood coagulation cascade, especially methods for the treatment of thrombotic disease in a patient, by administration of the compounds of formula I.

The invention further provides methods for the use of these compounds in manufacturing medicaments for inhibiting thrombin and factor Xa in a patient, medicaments for therapeutic modulation of the coagulation cascade. Subjects who may be treated with the compositions of the invention include, but are not limited to, patients experiencing thrombotic and thromboembolic disease, patients in situations requiring the establishment of reperfusion or delaying the occlusion of blood circulation such as patients experiencing acute coronary syndrome, atrial fibrillation, deep-vein thrombosis and pulmonary embolism, acute disseminated intravascular coagulation, and heparin-induced thrombocytopenia (HIT), and patients requiring percutaneous coronary intervention, cardiopulmonary bypass for heart surgery, an extracorporeal membrane oxygenation circuit for extracorporeal life support, interventional cardiology (angioplasty and stent implantation), and haemofiltration.

DETAILED DESCRIPTION OF THE INVENTION

The invention provides compounds having the following formula (I) A compound having the following formula

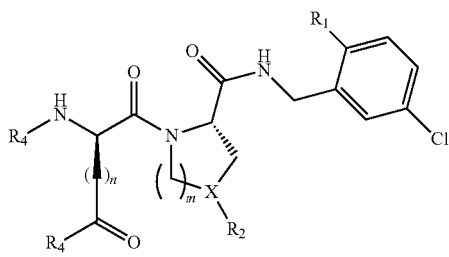

or a pharmaceutically acceptable salt thereof;
wherein:
n is an integer between 1 and 2 inclusively;
m is an integer between 0 and 2 inclusively;
X is selected from the group consisting of CH or N;
$R_1$ is selected from the group consisting of —$CH_2NH_2$, and

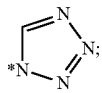

$R_2$ is selected from the group consisting of —H, —OH, —$NH_2$ and acetyl;
$R_3$ is selected from the group consisting of —H, benzyloxycarbonyl and benzylsulfonyl; and
$R_4$ is selected from the group consisting of —OH,

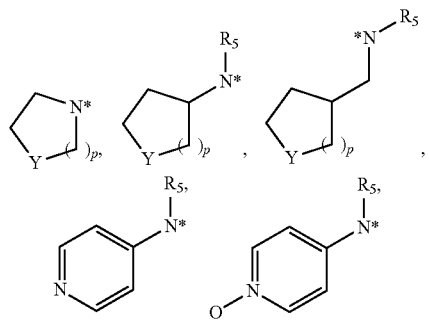

wherein p is an integer between 0 and 2 inclusively, Y is selected from the group consisting of —O—, —S—, —S(=O)—, —$SO_2$—, methylene, —CH(OH)—, —CH($NH_2$)—, —CH($CH_2$—OH)—, —CH($CH_2$—$NH_2$)— or —N($R_6$)—, $R_5$ is selected from the group consisting of —H or a simple ($C_1$-$C_3$) alkyl and $R_6$ is selected from the group consisting of —H; a simple ($C_1$-$C_3$) alkyl or a simple ($C_1$-$C_3$) acyl. In some embodiments, $R_4$ is

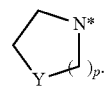

In some embodiments, n is 2. In other embodiments, m is 1. In still other embodiments, X is CH, and $R_2$ is —H or —$NH_2$. In certain embodiments, $R_1$ is —$CH_2NH_2$.

In preferred embodiments, $R_3$ is selected from the group consisting of benzyloxycarbonyl and benzylsulfonyl.

In another preferred embodiments, $R_4$ is selected from the group of

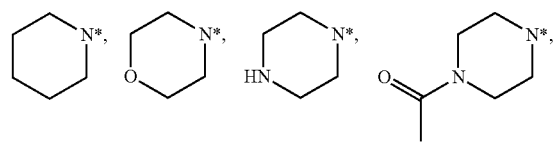

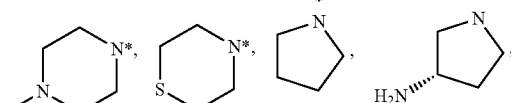

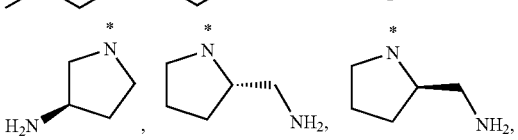

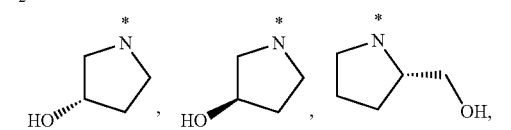

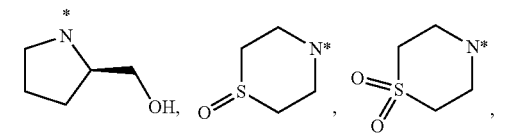

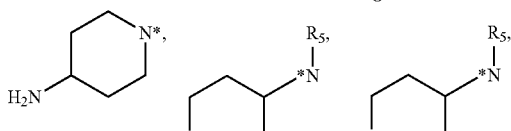

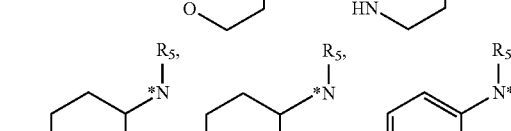

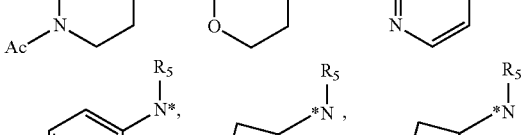

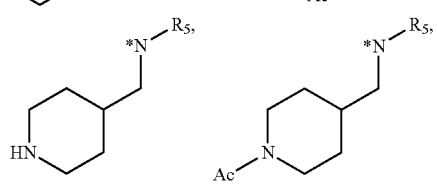

wherein $R_5$ is —H or methyl. In some embodiments, $R_4$ is
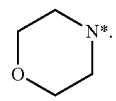
In another preferred embodiment, $R_1$ is —$CH_2NH_2$, and $R_4$ is selected from the group of
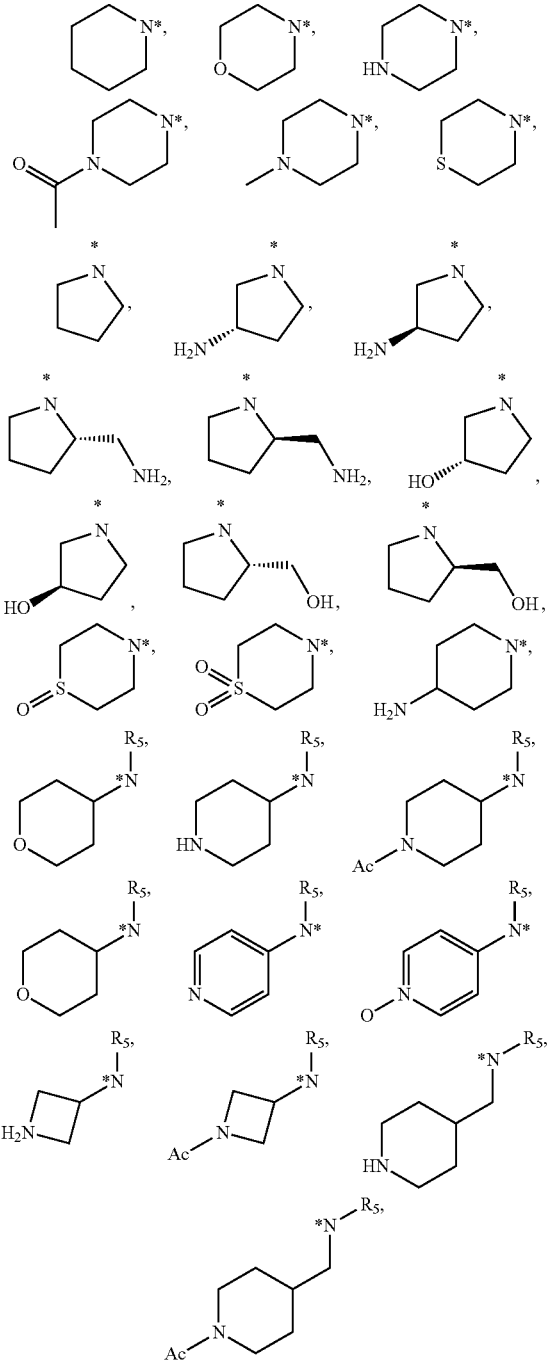
and wherein $R_5$ is —H or methyl
Representative examples of the compounds of the invention are set out below.
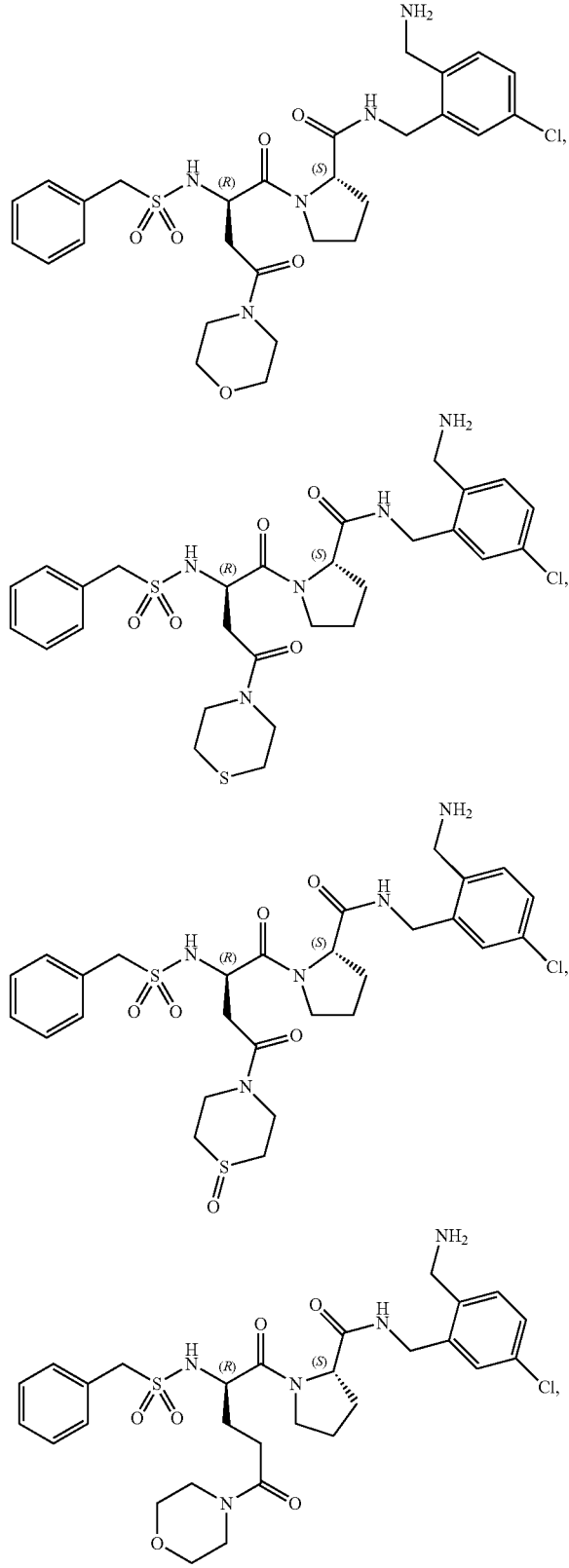

-continued
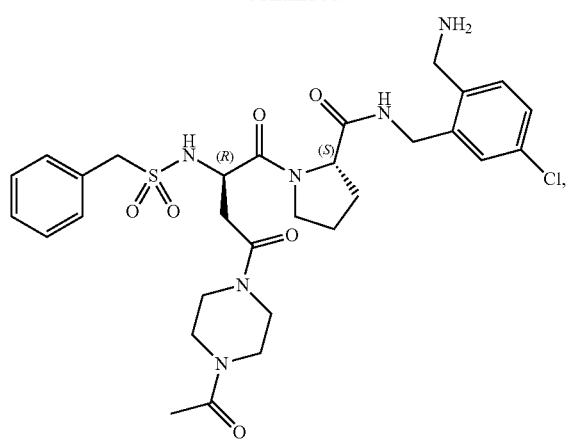
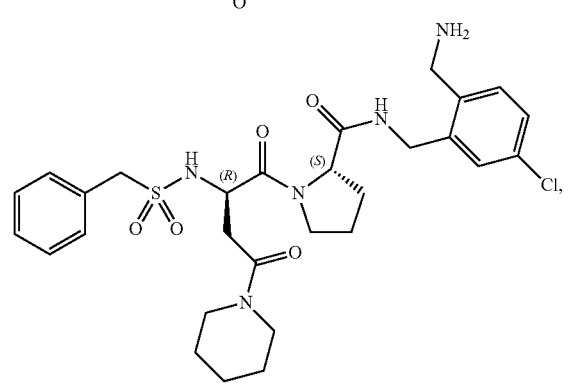
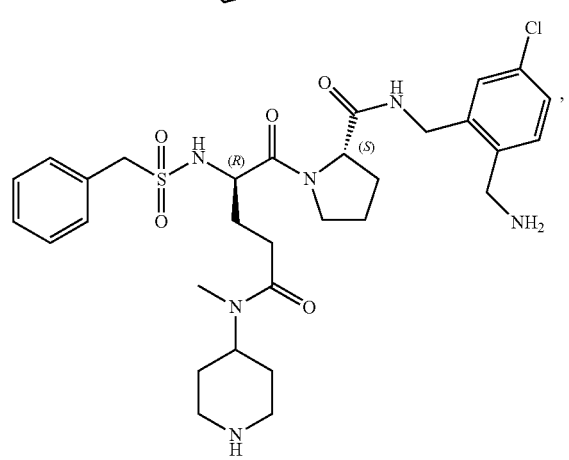
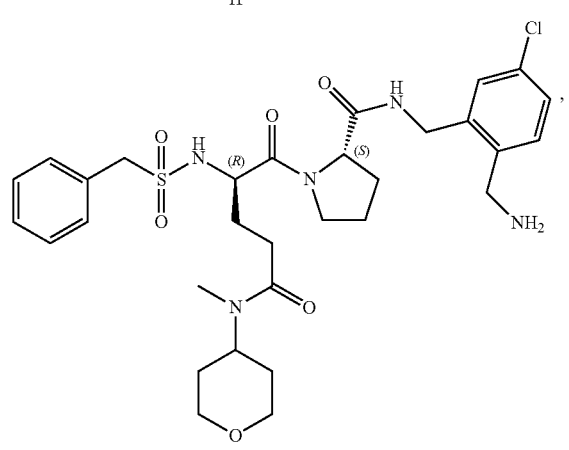
-continued
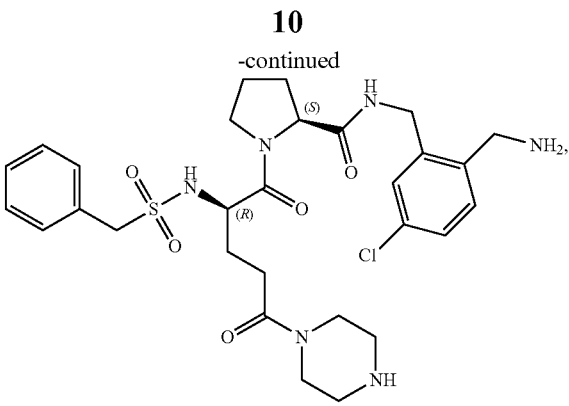
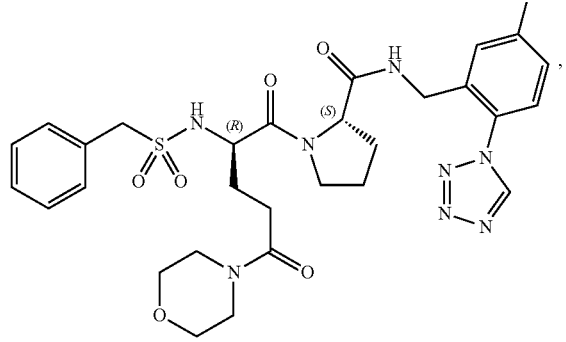
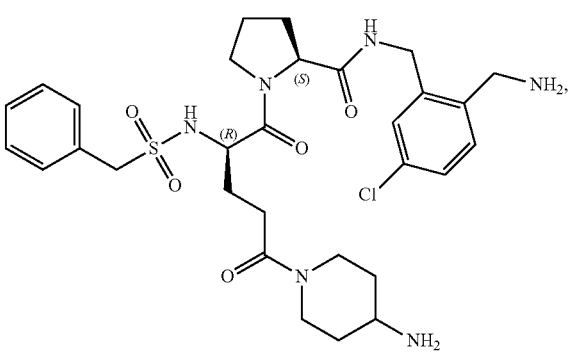
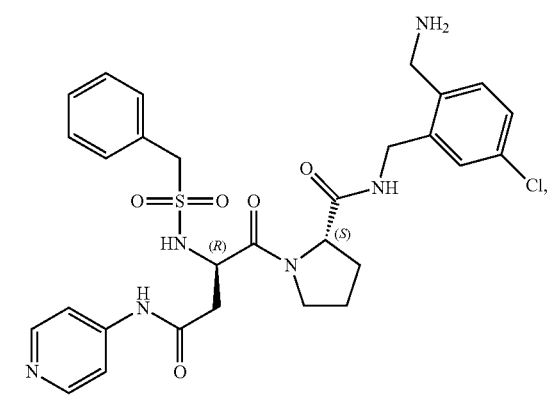

11
-continued
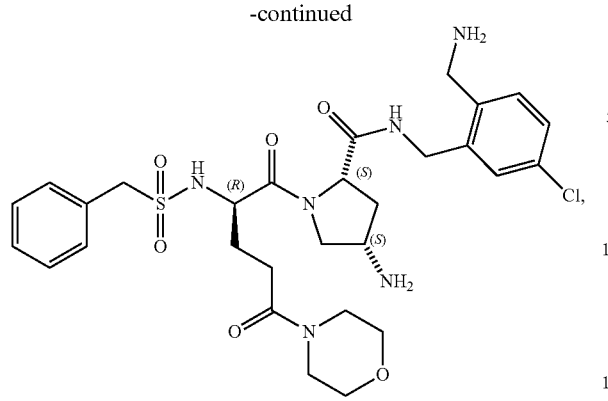
12
-continued
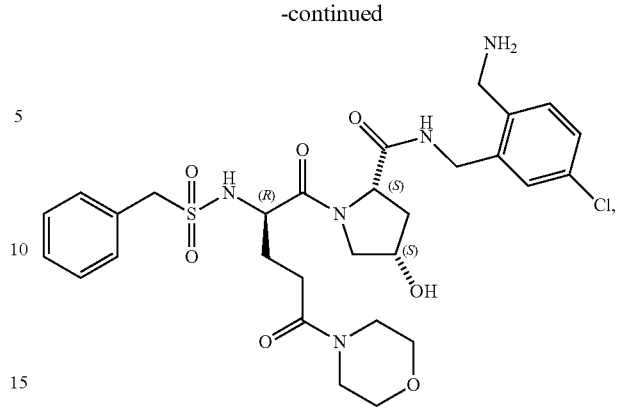
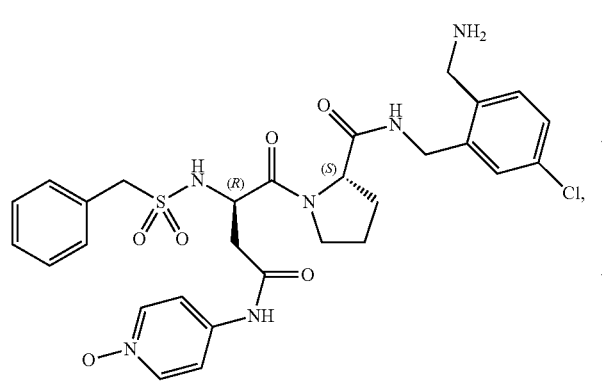
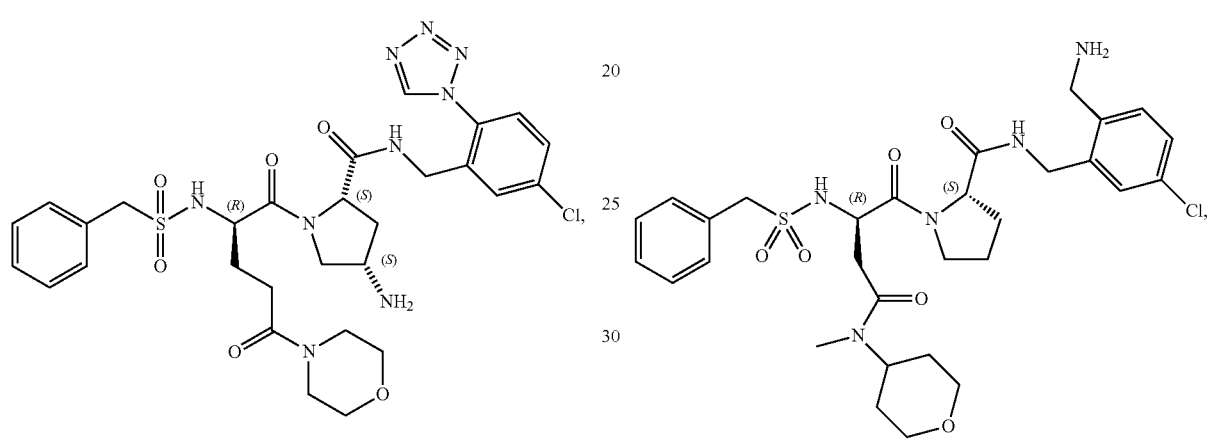
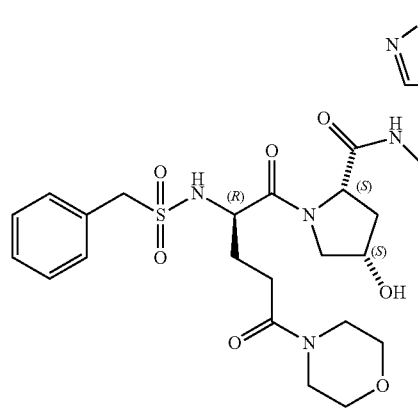
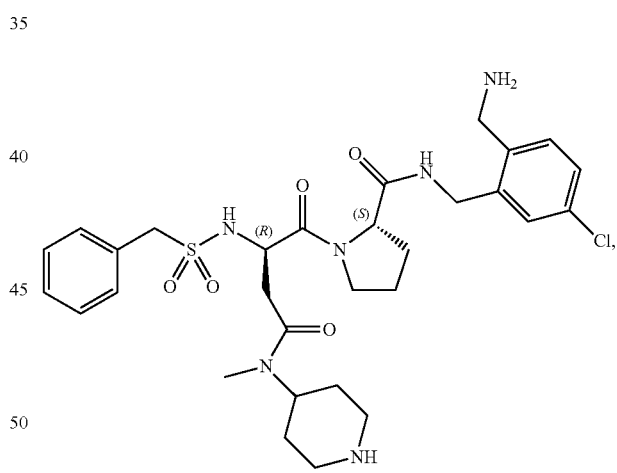
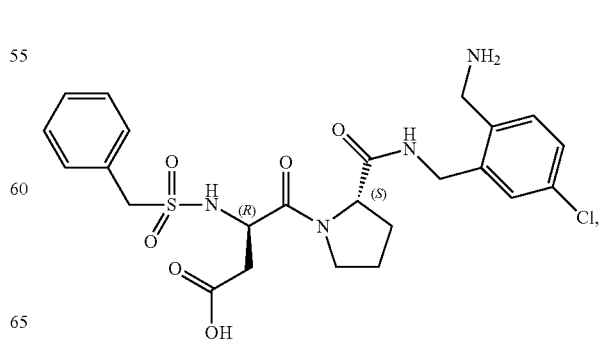

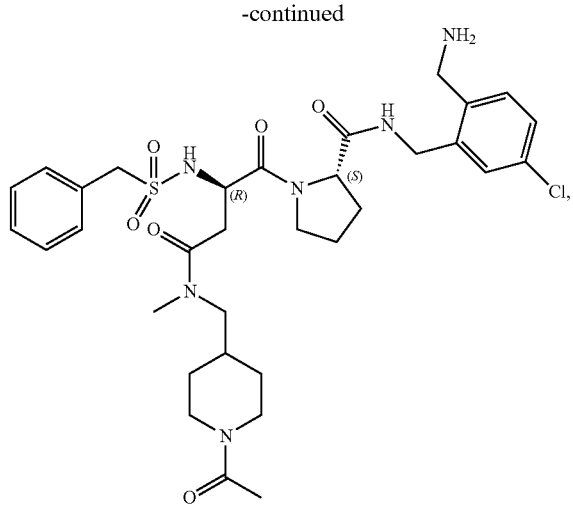
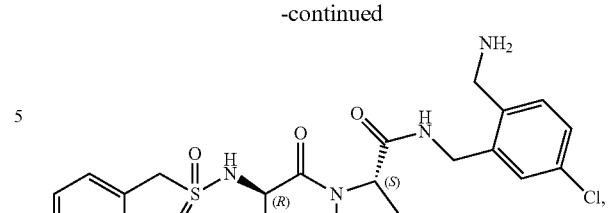
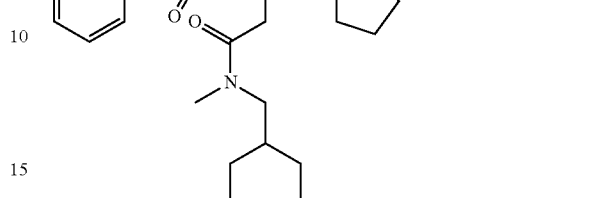
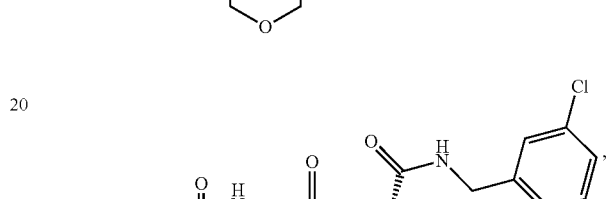
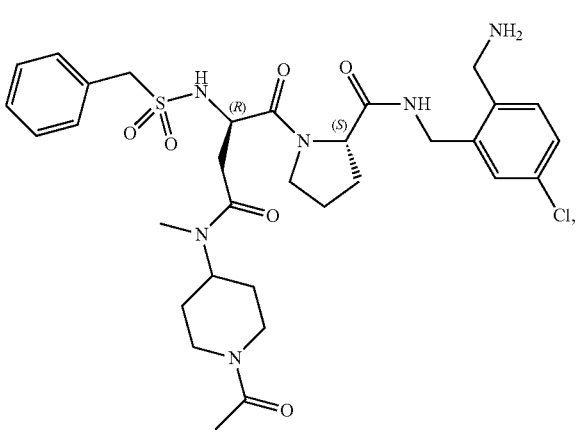
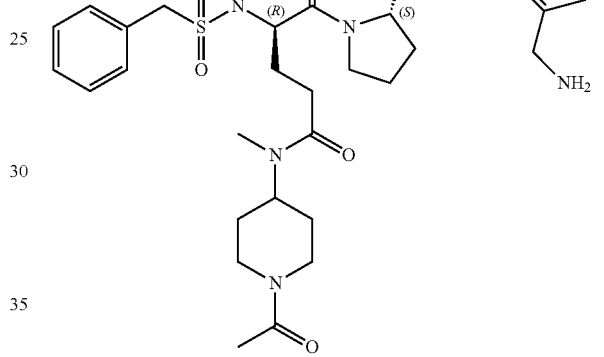
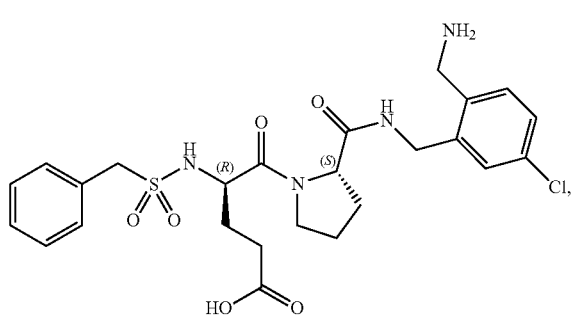
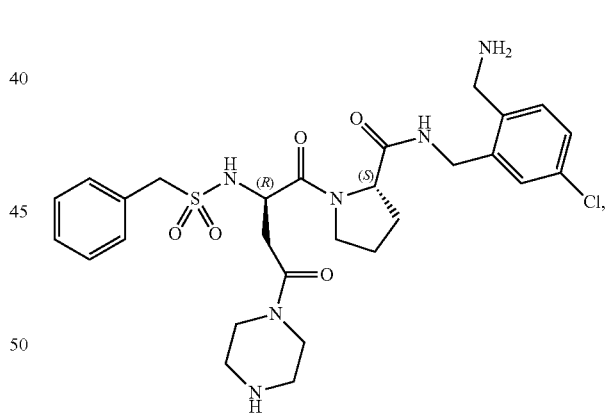
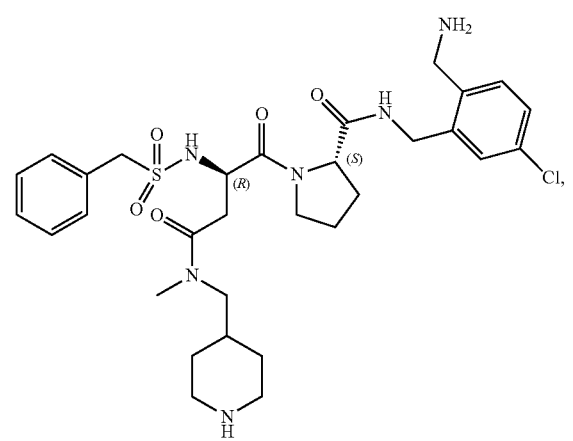
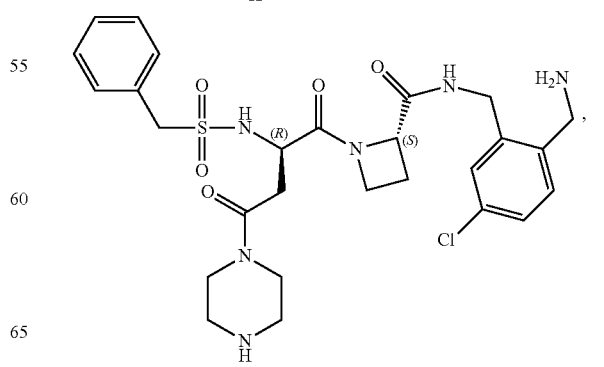

15
-continued
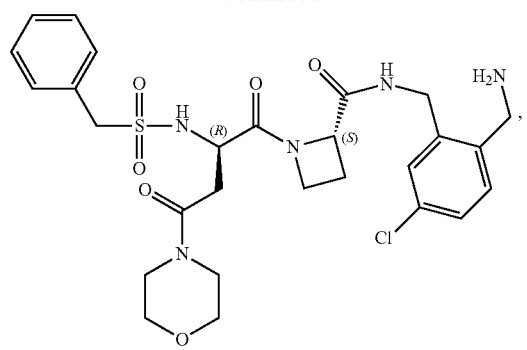
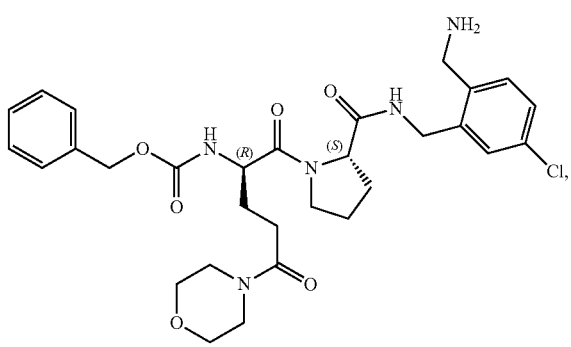
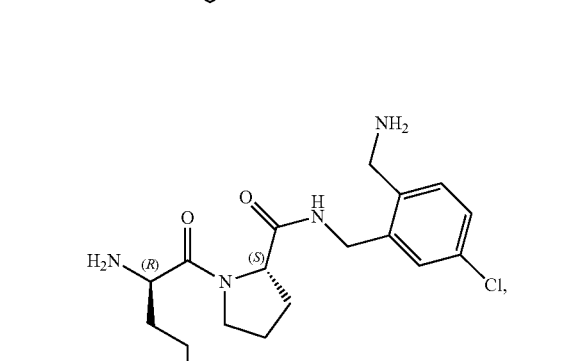
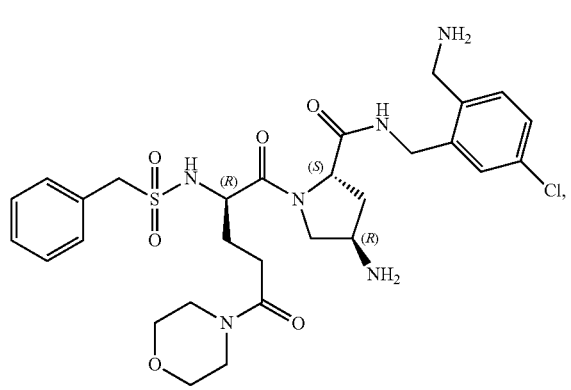
16
-continued
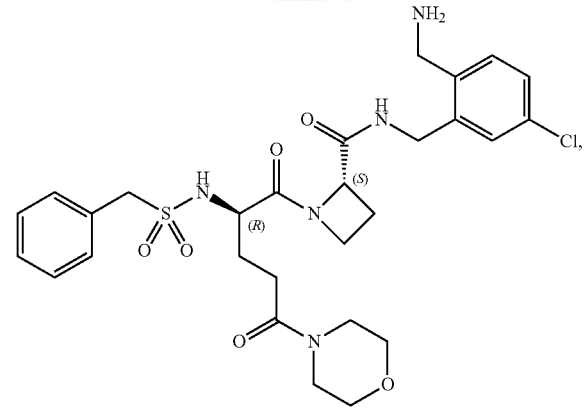
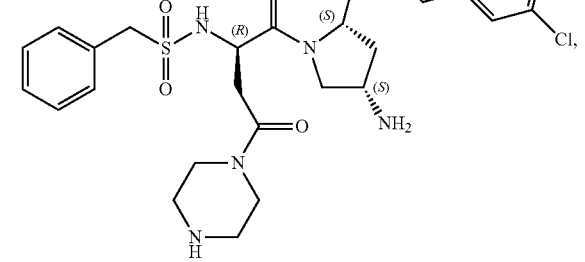

17
-continued
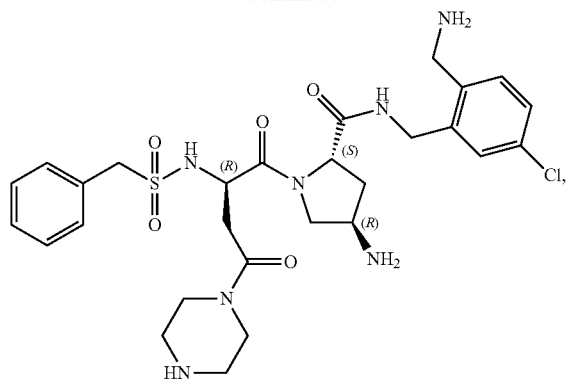
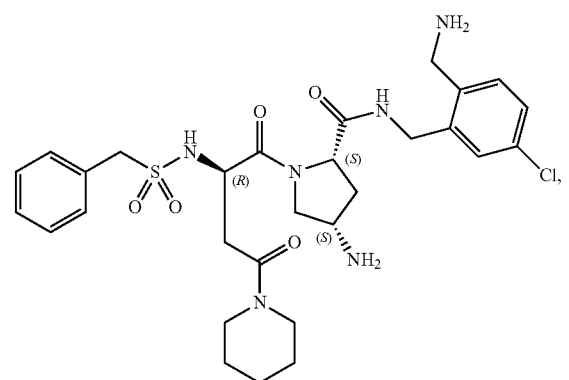
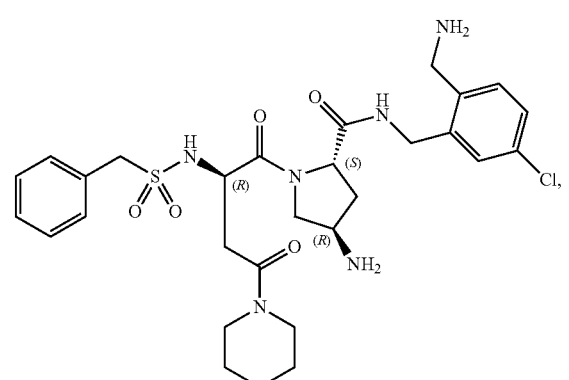
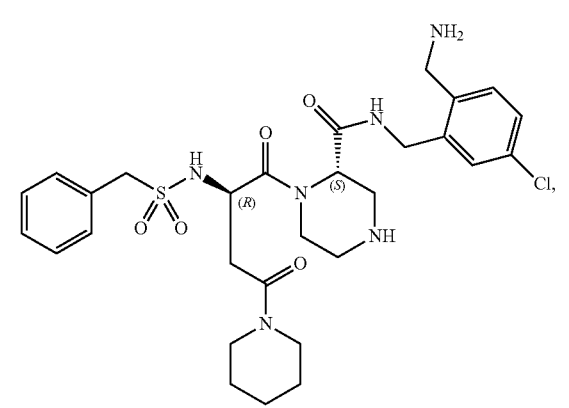
18
-continued
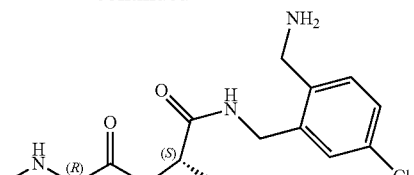
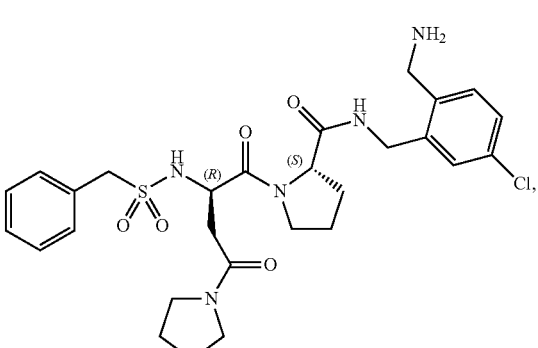
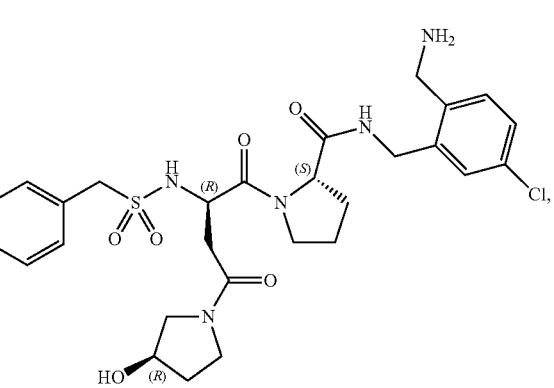
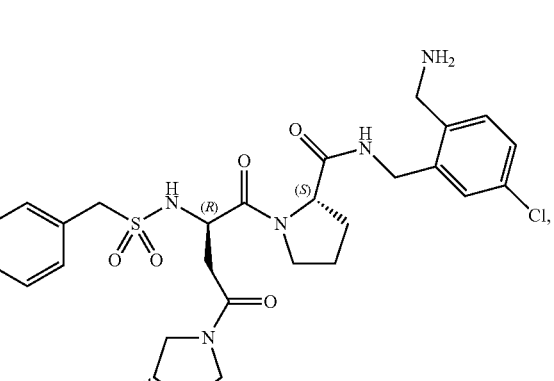

-continued

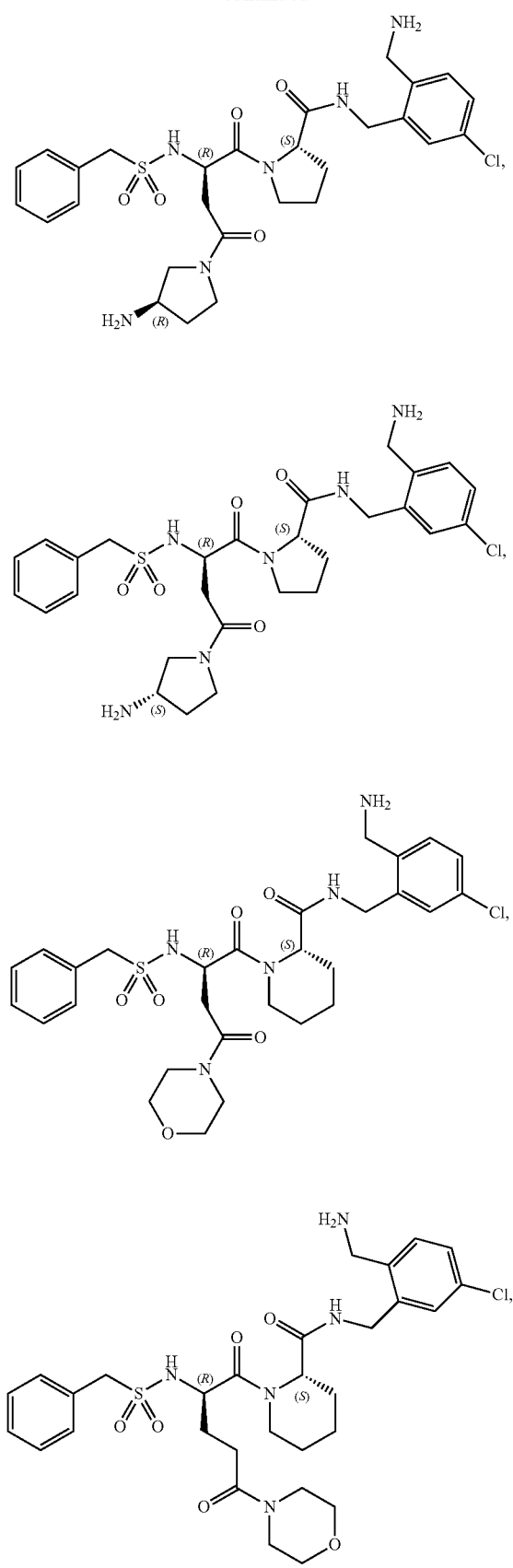

-continued

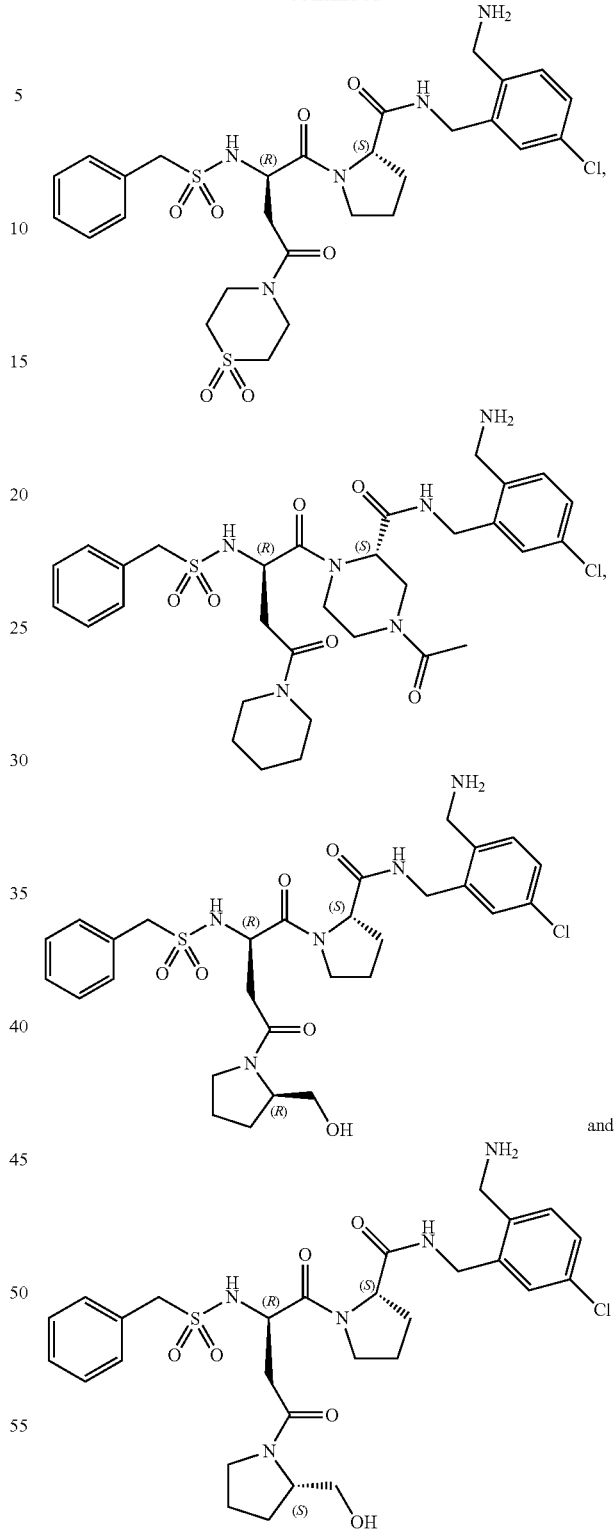

or a pharmaceutically acceptable salt thereof.

The pharmaceutically acceptable salts of the compounds of the invention are preferably formed by addition of any acid known to be useful in the formation of pharmaceutical salts. Preferred acids for salt formation include HCl, HBr, sulfuric acid, phosphoric acid, acetic acid, citric acid, methanesulfonic acid, trifluoroacetic acid, and p-toluenesulfonic acid.

The invention also provides pharmaceutical composition comprising one or more compounds of the invention, in combination with one or more pharmaceutically acceptable carriers or excipients. Such excipients include, but are not limited to, fillers, binding agents, lubricants, preservatives, water, buffers, and disintegrants. The compositions may be in the form of solids or liquids, compounded for oral administration, or solutions or suspensions suitable for parenteral administration. In particular, a buffered saline solution suitable for parenteral administration is provided, as are powdered or lyophilized compositions suitable for reconstitution into a buffered saline solution.

Pharmaceutically acceptable carriers and excipient are those compounds, solutions, substances or materials that can be used to produce formulations of the compounds of the present invention that are suitable for administered to a subject. In particular, carriers and excipients of the present invention are those useful in preparing a pharmaceutical composition that is generally safe, non-toxic and neither biologically nor otherwise undesirable, and that may present pharmacologically favorable profiles, and includes carriers and excipient that are acceptable for veterinary use as well as human pharmaceutical use. Suitable pharmaceutically acceptable carriers and excipients are well known in art and can be determined by those of skill in the art as the clinical situation warrants. The skilled artisan will understand that diluents are included within the scope of the terms carriers and excipients. Examples of suitable carriers and excipients include saline, buffered saline, dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717), hydrophilic and hydrophobic carriers, and combinations thereof. Hydrophobic carriers include, for example, fat emulsions, lipids, PEGylated phospholids, polymer matrices, biocompatible polymers, lipospheres, vesicles, particles, and liposomes.

Excipients included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof. The compositions may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate. The particular carrier, diluent or excipient used will depend upon the means and purpose for which the active ingredient is being applied. Pharmaceutically acceptable excipients also include tonicity agents that make the composition compatible with blood. Tonicity agents are particularly desirable in injectable formulations.

The compounds of the general formula I can be prepared by sequential formation of amide and sulfonamide bonds using suitably selected protecting groups. The term "protecting group" refers to a chemical group that exhibits the following characteristics: 1) reacts with a specific functionality to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Wuts and Greene (2007) Greene's Protective Groups in Organic Synthesis, 4$^{th}$ Ed. (John Wiley & Sons, Inc., New York). Preferred amino protecting groups include, but are not limited to, benzyloxycarbonyl (CBz), t-butyloxycarbonyl (Boc), t-butyldimethylsilyl (TBDMS), 9-fluorenyl-methyl-oxycarbonyl (Fmoc), 6-nitroveratryloxy carbonyl (Nvoc), nitropiperonyl, pyrenylmethoxycarbonyl, benzyl, nitrobenzyl, dimethoxybenzyl, 5-bromo-7-nitroindolinyl, and the like. Preferred hydroxyl protecting groups include acetyl, benzoyl, benzyl, tetrahydropyranyl, TBDMS, methoxy or ethoxy methyl ether and the like. Preferred carboxyl protecting groups include, but are not limited to, methyl, ethyl, benzyl, TBDMS, 2,2,2-trichloroethyl, 2-(trimethylsilyl)ethyl, (2-(trimethylsilyl)ethoxy)methyl, phenyl and nitrophenyl esters, ethyl, methyl and phenyl thioesters and the like.

The compounds of the invention may be prepared in several ways. Preferred synthetic approaches involve the formation of amide and sulfonamide bonds between pre-synthesized components.

As used herein, the expression "an activated carboxylic acid" derived from a given acid refers to derivatives of carboxyxlic acids that are reactive toward amines, including but not limited to active esters, mixed anhydrides, and acyl halides, as are well-known in the art of peptide synthesis. Suitable examples include, but are not limited to, N-hydroxybenzotriazole esters, O-acylated isoureas, pentachloro- and pentafluoro-phenyl esters, acyl chlorides, and mixed anhydrides with hindered acids and carbonic acid monoesters. Additional suitable examples are acyloxy phosphonium salts. Preferred activated carboxylic acids are the mixed anhydride obtained by reaction with isobutyl chloroformate, or the N-hydroxybenzotriazole ester. These activated carboxylic acid derivatives may be used in pure form or may be produced transiently in the reaction mixture using methods that are well known to those skilled in the art.

Compounds of structure

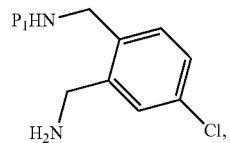

wherein $P^1$ is an amino protecting group are known in the prior art and for example can be obtained by the methods described in Nelson et al., *J. Org. Chem.* 69, 3620-3627, 2004 and Selnik et al., WO 02/50056, 2002. Compounds of structure

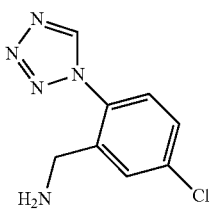 [SMILES: NCc1cc(Cl)ccc1-n1cnnn1]

are similarly known in the prior art and can be obtained by the methods described in Young et al., *J. Med. Chem.* 47, 2995-3008, 2004.

In an embodiment of the invention, the compounds of the invention may be prepared by the acylation of a compound of structure

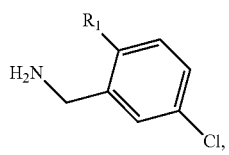

wherein $R_1$ is selected from the group consisting of —$CH_2NHP^1$, and

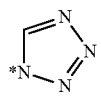

and $P^1$ is an amino protecting group with an activated carboxylic acid derived from the acid of formula A

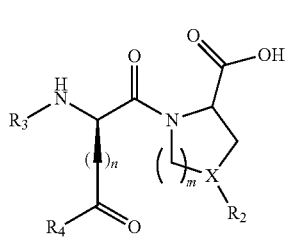

(A)

wherein n is an integer between 1 and 2 inclusively; m is an integer between 0 and 2 inclusively; X is selected from the group consisting of CH or N; $R_2$ is selected from the group consisting of —H, —OH and —$NHP^2$ if X is CH and —$P^2$ or acetyl if X is N; $R_3$ is selected from the group consisting of —H, benzyloxycarbonyl and benzylsulfonyl; and $R_4$ is selected from the group consisting of —$OP^3$,

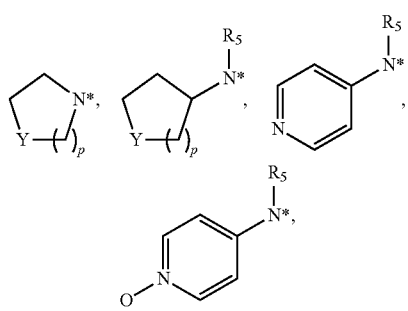

wherein p is an integer between 1 and 2 inclusively, Y is selected from the group consisting of —O—, —S—, —S(=O)—, —$SO_2$—, methylene, —CH(OH)—, —CH($NHP^2$)— or —N($R_6$)— and $R_5$ is selected from the group consisting of —H or a simple ($C_1$-$C_3$) alkyl and $R_6$ is selected from the group consisting of —$P^2$, a simple ($C_1$-$C_3$) alkyl or a simple ($C_1$-$C_3$) acyl; Each $P^2$ is independently an amino protecting group; and $P^3$ is a carboxyl protecting group. Subsequent cleavage of the amino protecting groups $P^1$ and $P^2$ or of the amino protecting groups $P^1$ and $P^2$ and the carboxyl protecting group $P^3$ affords the compounds of the invention.

If $P^1$ and one or all of the $P^2$ groups are the same amino protecting group, or protecting groups that are removed under the same conditions, then the final deprotection may be performed as a single step. For example, if $P^1$ and $P^2$ are all tert-butyloxycarbonyl protecting groups, they may all be removed in a single protolytic step, by treatment with a strong acid such as trifluoroacetic acid in dichloromethane or hydrochloric acid in dioxane. Similarly if $P^1$ is a tert-butyloxycarbonyl group and one or all of the $P^2$ groups are benzyloxycarbonyl groups, they may all be removed in a single synthetic step by treatment with a strong acid such as hydrobromic acid in acetic acid. In contrast, the removal of the protecting groups can be performed in two separate steps. Thus, if $P^1$ is a tert-butyloxycarbonyl protecting group and one or all of the $P^2$ groups are 9-fluorenylmethyloxycarbonyl groups, then $P^2$ removal may be performed with a strongly basic reagent, such as piperidine alone or in dimethylformamide, and in a subsequent step, $P^1$ removal may be performed by treatment with a strong acid, such as trifluoroacetic acid in dichloromethane or hydrochloric acid in dioxane.

Similarly, $P^3$ may be removed in concert with $P^1$ and/or $P^2$ or it may be removed in a separate step. For example, if $P^3$ is a tert-butyl protecting group and $P^1$ is a tert-butyloxycarbonyl group, they may all be removed by treatment with a strong acid such as trifluoroacetic acid in dichloromethane or hydrochloric acid in dioxane. In contrast, $P^3$ may be removed in a separate step from the removal of $P^1$ and/or $P^2$. Thus if $P^3$ is a methyl group and $P^1$ is a tert-butyloxycarbonyl group, then $P^3$ may be removed by treatment with a strong nucleophile, such as lithium hydroxide in dioxane/water, and $P^1$ may be removed in a separate step, by treatment with a strong acid, such as trifluoroacetic acid in dichloromethane or hydrochloric acid in dioxane.

Final purification of the compounds of the invention is preferably carried out by preparative reversed-phase chromatography, crystallization and/or recrystallization. In particular, the selection of a suitably crystalline salt of the compounds of the invention can be a preferred method for the final purification of the compounds of the invention on a large scale, as is routine in the art.

In an embodiment of the invention, compounds of general formula A can further be prepared by the acylation of an amine of general formula

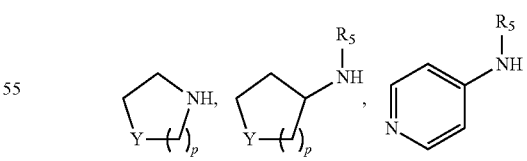

wherein p is an integer between 1 and 2 inclusively, Y is selected from the group consisting of —O—, —S—, —S(=O)—, —$SO_2$—, methylene, —CH(OH)—, —CH($NHP^2$)— or —N($R_6$)—, $R_5$ is selected from the group consisting of —H or a simple ($C_1$-$C_3$) alkyl and $R_6$ is selected from the group consisting of —$P^2$; a simple ($C_1$-$C_3$) alkyl or a simple ($C_1$-$C_3$) acyl, with an activated carboxylic acid derived from structure G (G)

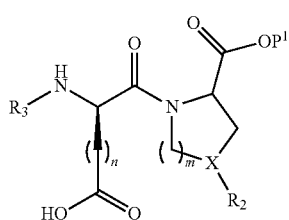

wherein n is an integer between 1 and 2 inclusively; m is an integer between 0 and 2 inclusively; X is selected from the group consisting of CH or N; $R_2$ is selected from the group consisting of —H, —OH and —$NHP^2$ if X is CH and —$P^2$ or acetyl if X is N; $R_3$ is selected from the group consisting of benzyloxycarbonyl and benzylsulfonyl; $P^1$ is a carboxyl protecting group; and each $P^2$ is independently an amino protecting group. Subsequent cleavage of the protecting groups $P^1$; affords compounds of general formula A. The sequence of deprotection steps is described herein.

In a further embodiment of the invention, the compounds of general formula A can further be prepared by acylation of an amine of formula H with an activated carboxylic acid derived from the acid of formula I

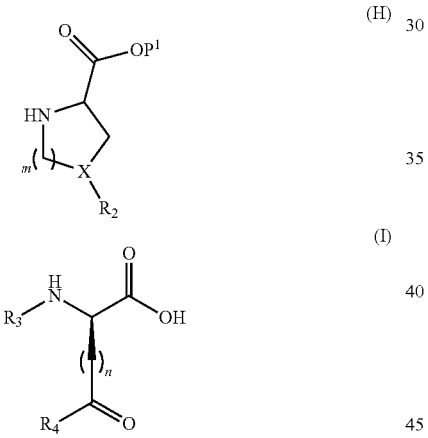

(H)

(I)

wherein n is an integer between 1 and 2 inclusively; m is an integer between 0 and 2 inclusively; X is selected from the group consisting of CH or N; $P^1$ is a carboxyl protecting group; $R_2$ is selected from the group consisting of —H, —OH and —$NHP^2$ if X is CH and —$P^2$ or acetyl if X is N; $R_3$ is selected from the group consisting of benzyloxycarbonyl and benzylsulfonyl; and $R_4$ is selected from the group consisting of —$OP^3$,

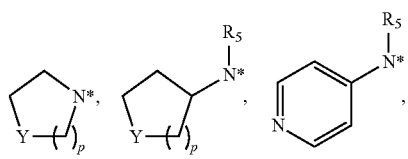

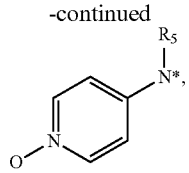

wherein p is an integer between 1 and 2 inclusively, Y is selected from the group consisting of —O—, —S—, —S(=O)—, —$SO_2$—, methylene, —CH(OH)—, —CH($NHP^2$)— or —N($R_6$)—, $R_5$ is selected from the group consisting of —H or a simple ($C_1$-$C_3$) alkyl and $R_6$ is selected from the group consisting of —$P^2$, a simple ($C_1$-$C_3$) alkyl or a simple ($C_1$-$C_3$) acyl; Each $P^2$ is independently an amino protecting group; and $P^3$ is a carboxyl protecting group. Subsequent cleavage of the protecting group $P^1$. Affords compounds of general formula A. The sequence of deprotection steps is described herein.

In a further embodiment of the invention, the compounds of the invention may be prepared by acylation of a compound of structure

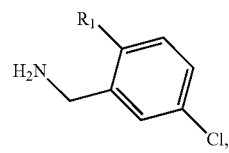

wherein $R_1$ is selected from the group consisting of —$CH_2NHP^1$, and

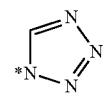

and $P^1$ is an amino protecting group with an activated carboxylic acid derived from the acid of formula B

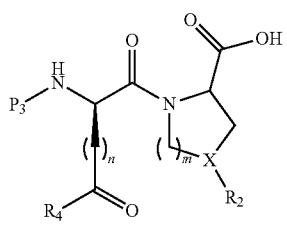

(B)

wherein n is an integer between 1 and 2 inclusively; m is an integer between 0 and 2 inclusively; X is selected from the group consisting of CH or N; $R_2$ is selected from the group consisting of —H, —OH and —$NHP^2$ if X is CH and —$P^2$ or acetyl if X is N; $R_4$ is selected from the group consisting of —$OP^4$,

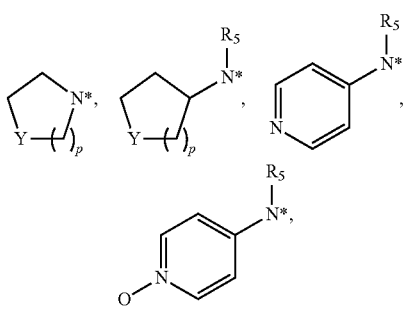

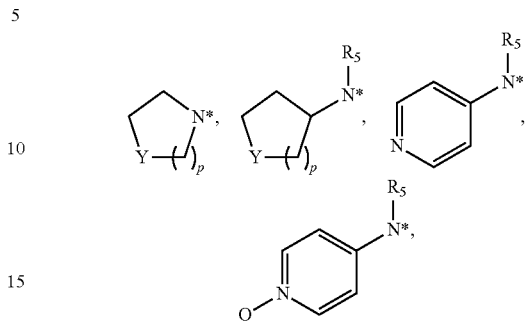

wherein p is an integer between 1 and 2 inclusively, Y is selected from the group consisting of —O—, —S—, —S(=O)—, —SO$_2$—, methylene, —CH(OH)—, —CH(NHP$^2$)— or —N(R$_6$)—, R$_5$ is selected from the group consisting of —H or a simple (C$_1$-C$_3$) alkyl and R$_6$ is selected from the group consisting of —P$^2$, a simple (C$_1$-C$_3$) alkyl or a simple (C$_1$-C$_3$) acyl; Each P$^2$ is independently an amino protecting group; P$^3$ is an amino protecting group which can be cleaved in the presence of P$^1$, P$^2$ and P$^4$; and P$^4$ is a carboxyl protecting group. The amino protecting group P$^3$; is subsequently cleaved and the resulting deprotected amino group is treated with a benzylsulfonyl halide, before cleavage of the amino protecting groups P$^1$ and P$^2$ and the carboxyl protecting group P$^4$. The sequence of deprotection steps is described herein.

In a further embodiment of the invention, the compounds of the invention may be prepared by acylation of an amine of formula D with an activated carboxylic acid derived from the acid of formula E

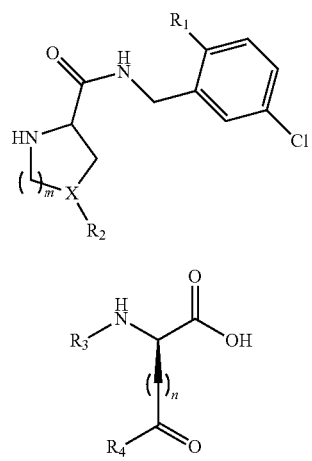

wherein n is an integer between 1 and 2 inclusively; m is an integer between 0 and 2 inclusively; X is selected from the group consisting of CH or N; R$_1$ is selected from the group consisting of —CH$_2$NHP$^1$, and

P$^1$ is an amino protecting group; R$_2$ is selected from the group consisting of —H, —OH and —NHP$^2$ if X is CH and —P$^2$ or acetyl if X is N; R$_3$ is selected from the group consisting of benzyloxycarbonyl and benzylsulfonyl; and R$_4$ is selected from the group consisting of —OP$^3$, wherein p is an integer between 1 and 2 inclusively, Y is selected from the group consisting of —O—, —S—, —S(=O)—, —SO$_2$—, methylene, —CH(OH)—, —CH(NHP$^2$)— or —N(R$_6$)—, R$_5$ is selected from the group consisting of —H or a simple (C$_1$-C$_3$) alkyl and R$_6$ is selected from the group consisting of —P$^2$, a simple (C$_1$-C$_3$) alkyl or a simple (C$_1$-C$_3$) acyl; Each P$^2$ is independently an amino protecting group; and P$^3$ is a carboxyl protecting group. Subsequent cleavage of the protecting groups P$^1$, P$^2$ and P$^3$ affords the compounds of the invention. The sequence of deprotection steps is described herein.

Compounds of the general formula D can further be obtained by the acylation of acylation of a compound of structure

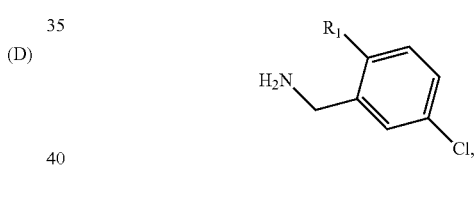

wherein R$_1$ is selected from the group consisting of —CH$_2$NHP$^1$, and

and P$^1$ is an amino protecting group with an activated carboxylic acid derived from a compound of structure

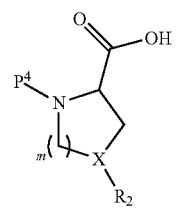

wherein m is an integer between 0 and 2 inclusively, X is selected from the group consisting of CH or N, R$_2$ is selected from the group consisting of —H, —OH and —NHP$^2$ if X is CH and —P$^2$ or acetyl if X is N, and each P$^2$ and P$^4$ are each amino protecting groups whereby P⁴ can be selectively removed in the presence of P²; and subsequent cleavage of protecting group P⁴.

In a further embodiment of the invention, the compounds of the invention may be prepared by the acylation of an amine of general formula

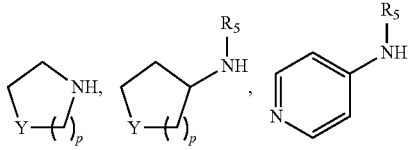

wherein p is an integer between 1 and 2 inclusively, Y is selected from the group consisting of —O—, —S—, —S(=O)—, —SO₂—, methylene, —CH(OH)—, —CH(NHP²)— or —N(R₆)—, R₅ is selected from the group consisting of —H or a simple (C₁-C₃) alkyl and R₆ is selected from the group consisting of —P², a simple (C₁-C₃) alkyl or a simple (C₁-C₃) acyl with an activated carboxylic acid derived from structure F

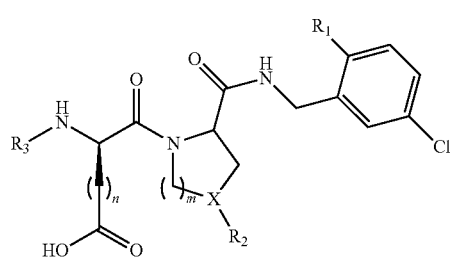

(F)

wherein n is an integer between 1 and 2 inclusively; m is an integer between 0 and 2 inclusively; X is selected from the group consisting of CH or N; R₁ is selected from the group consisting of —CH₂NHP¹, and

wherein P¹ is an amino protecting group; R₂ is selected from the group consisting of —H, —OH and —NHP² if X is CH and —P² or acetyl if X is N; R₃ is selected from the group consisting of benzyloxycarbonyl and benzylsulfonyl; and Each P² is independently an amino protecting group. Subsequent cleavage of the amino protecting groups P¹ and P² affords the compounds of the invention. The sequence of deprotection is described herein.

Compounds of general formula F can be prepared by any of the processed described herein, wherein R₄ is OP³ and P³ is a carboxyl protecting group that can be removed in the presence of all other protecting groups. Subsequent removal of P³ affords the compounds of general formula F.

The key intermediates used in the processes described in herein leading to the compounds of the invention are themselves embodiments of the inventions. This includes compound having the general formula A

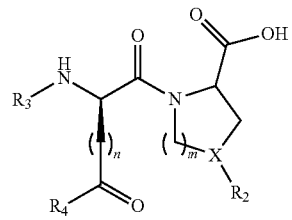

(A)

wherein n is an integer between 1 and 2 inclusively; m is an integer between 0 and 2 inclusively; X is selected from the group consisting of CH or N; R₂ is selected from the group consisting of —H, —OH and —NHP² if X is CH and —P² or acetyl if X is N; R₃ is selected from the group consisting of —P², benzyloxycarbonyl and benzylsulfonyl; and R₄ is selected from the group consisting of —OP³,

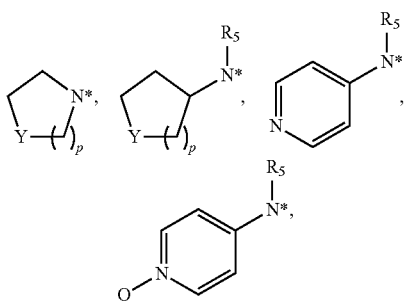

wherein p is an integer between 1 and 2 inclusively, Y is selected from the group consisting of —O—, —S—, —S(=O)—, —SO₂—, methylene, —CH(OH)—, —CH(NHP²)— or —N(R₆)—, R₅ is selected from the group consisting of —H or a simple (C₁-C₃) alkyl and R₆ is selected from the group consisting of —P², a simple (C₁-C₃) alkyl or a simple (C₁-C₃) acyl; Each P² is independently an amino protecting group; and P³ is a carboxyl protecting group.

Similarly, are also included as embodiments of the invention, compounds having the general formula C

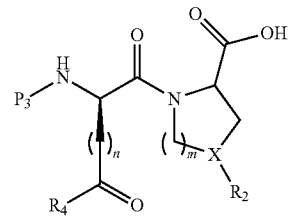

(C)

wherein n is an integer between 1 and 2 inclusively; m is an integer between 0 and 2 inclusively; X is selected from the group consisting of CH or N; R₂ is selected from the group consisting of —H, —OH and —NHP² if X is CH and —P² or acetyl if X is N; R₄ is selected from the group consisting of —OP⁴,

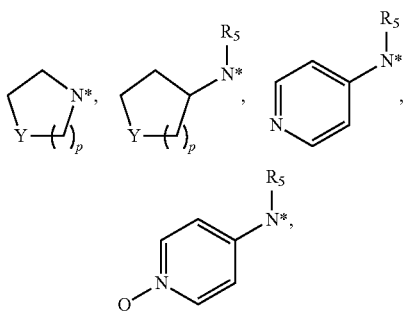

wherein p is an integer between 1 and 2 inclusively, Y is selected from the group consisting of —O—, —S—, —S(=O)—, —SO$_2^-$, methylene, —CH(OH)—, —CH(NHP$^2$)— or —N(R$_6$)—, R$_5$ is selected from the group consisting of —H or a simple (C$_1$-C$_3$) alkyl and R$_6$ is selected from the group consisting of —P$^2$, a simple (C$_1$-C$_3$) alkyl or a simple (C$_1$-C$_3$) acyl; Each P$^2$ is independently an amino protecting group; P$^4$ is a carboxyl protecting group; and P$^3$ is an amino protecting group which can be cleaved in the presence of each P$^2$.

Similarly, are also included as embodiments of the invention, compounds having the

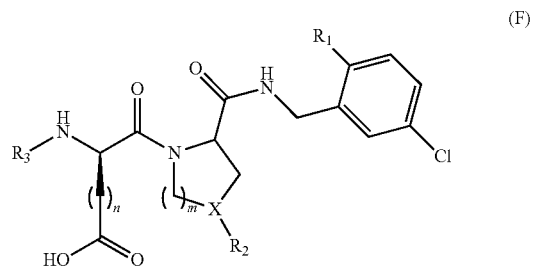

wherein n is an integer between 1 and 2 inclusively; m is an integer between 0 and 2 inclusively; X is selected from the group consisting of CH or N; R$_1$ is selected from the group consisting of —CH$_2$NHP$^1$, and

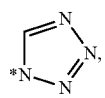

wherein P$^1$ is an amino protecting group; R$_2$ is selected from the group consisting of —H, —OH and —NHP$^2$ if X is CH and —P$^2$ or acetyl if X is N; R$_3$ is selected from the group consisting of —P$^2$, benzyloxycarbonyl and benzylsulfonyl; and each P$^2$ is independently an amino protecting group.

Similarly, are also included as embodiments of the invention, compounds having the following formula G

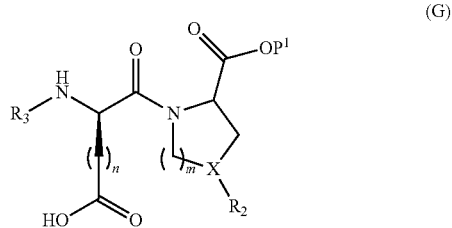

wherein n is an integer between 1 and 2 inclusively; m is an integer between 0 and 2 inclusively; X is selected from the group consisting of CH or N; R$_2$ is selected from the group consisting of —H, —OH and —NHP$^2$ if X is CH and —P$^2$ or acetyl if X is N; R$_3$ is selected from the group consisting of —P$^2$, benzyloxycarbonyl and benzylsulfonyl; P$^1$ is a carboxyl protecting group; and each P$^2$ is independently an amino protecting group.

Representative examples of the intermediates used in the preparation of the compounds of the invention are described, but are not limited to, the compounds in the exemplification section. These intermediates are themselves compounds of the invention.

The invention also provides methods for therapy or prevention of a cardiovascular disorder, a thrombotic disorder or thromboembolic event in a patient, which comprise administering to a patient in need thereof an effective amount of at least one compound of formula I.

The compounds of the invention are useful for the therapeutic modulation of the blood coagulation cascade. As used herein, "therapeutic modulation" includes a condition were anticoagulation is indicated, and the in vivo stabilization or promotion of innate hemostatic activities. In particular, the compounds are useful for the therapy or prevention of a cardiovascular disorder, a thrombotic disease condition or a thromboembolic event in a patient. In these patients, there is a need to establish reperfusion or to delay reocclusion of the blood circulation in a patient, which can be performed by the administration of the compounds of the invention. Patients in need of such treatment include those undergoing surgery, in particular organ transplant and cardiac surgical procedures, and those suffering from an acquired or inborn derangement of hemostasis.

Subjects who may be treated with the compositions of the invention include, but are not limited to patients experiencing acute coronary syndrome, atrial fibrillation, deep-vein thrombosis and pulmonary embolism, acute disseminated intravascular coagulation, and heparin-induced thrombocytopenia (HIT), and patients requiring percutaneous coronary intervention, cardiopulmonary bypass for heart surgery, an extracorporeal membrane oxygenation circuit for extracorporeal life support, interventional cardiology (angioplasty and stent implantation), and haemofiltration.

In other preferred embodiments, the compounds of the invention can be used for treating or preventing thrombin-induced inflammation in a patient, including in situations wherein said inflammation is caused by a disease selected from the group consisting of adult respiratory distress syndrome, septic shock, septicemia and reperfusion damage; They can be used to inhibit thrombus accretion in a patient caused by clot-bound thrombin; They can be used for inhibiting platelet-dependent thrombosis in a patient; and they can be used for treating or preventing disseminated intravascular coagulation in a patient.

Preferably the compound or compounds are administered in the form of a pharmaceutical composition as described above. Those skilled in the art will appreciate that suitable doses will vary with the particular compound, the route of administration, the condition to be treated, and the hemostatic status of the patient. In general, daily doses in the range of 1 mg to 500 mg will be effective. Effective dosing levels can be determined by dose-ranging studies, which are routine and well within the ability of those skilled in the art. Dosing may be continuous (e.g., via an intravenous line), or unit doses can be administered one or more times daily, as needed to maintain an effective concentration in vivo. Preferably, dosing is adjusted so as to maintain a mean blood level ranging from 0.01 to 10 µg/ml during the period for which therapeutic modulation of the blood coagulation cascade is desired.

The invention further provides methods for dually inhibiting human thrombin and factor Xa, in a patient in need thereof, comprising administering to said patient an effective amount of one or more compounds of formula I. Effective doses are determined as described above.

The invention also provides for the use of a compound of formula I in the manufacture of medicaments for the therapeutic modulation of the blood coagulation cascade, the dual inhibition of human thrombin and factor Xa.

In another embodiment of the inventions, the compounds of the invention may be used in the manufacture of a composition for coating the surface of an invasive device to be inserted into a patient. In a preferred embodiment, the invasive device is a blood contacting invasive device. Examples of such devices are prostheses, stents, shunts, catheters or local drug delivery devices. As used herein, an invasive device may be any suitable medical device that can be implanted in a human or veterinary patient. Examples of such implantable devices include but are not limited to self-expandable stents, balloon-expandable stents, stent-grafts, grafts (e.g., aortic grafts), heart valve prostheses, cerebrospinal fluid shunts, pacemaker electrodes, catheters, endocardial leads, anastomotic devices and connectors, orthopedic implants such as screws, spinal implants, and electro-stimulatory devices. The underlying structure of the device can be of virtually any design. The device can be made of a metallic material or an alloy such as, but not limited to, stainless steel, titanium, tantalum, nickel-titanium alloy, platinum-iridium alloy, gold, magnesium, or combinations thereof. Devices made from polymers, including bioabsorbable or biostable polymers, could also be used with the embodiments of the present invention.

In preferred embodiments, the patient treated with the compounds of the invention is a human being.

The following examples are presented by way of example, and are intended to illustrate and explain the invention in detail. The scope of the invention is not limited to the examples presented.

EXAMPLES

Example 1

Synthesis of Dual Thrombin/Factor Xa Inhibitors

Analytical Methods
A.1.1 Analytical HPLC 1

| Variable | Parameters |
|---|---|
| Device | Shimadzu LC-10A system |
| Column | Phenomenex Luna $C_{18}$ 100 Å, 5 µm column, 4.6 × 250 mm |
| Mobile phase | A: TFA, 0.1%(v/v) in water; B: TFA, 0.1%(v/v) in methanol |
| Method | Linear gradient of 1% B per min |
| Flow rate | 1.0 mL/min |
| Detection wavelength | UV 220 nm |
| Column temperature | 25° C. |
| Injection volume | 30 µl |

A.1.2 Analytical HPLC 2

| Variable | Parameters |
|---|---|
| Device | Agilent 1100 series LC/MSD |
| Column | Phenomenex Onyx monolithic $C_{18}$ column, 2.0 × 50 mm |
| Mobile phase | A: formic acid, 0.1%(v/v) in water; B: formic acid, 0.1%(v/v) in methanol |
| Method | Linear gradient of 15 or 13.3% B per min |
| Flow rate | 0.6 mL/min |
| Detection wavelength | UV 220 nm |
| Column temperature | 25° C. |
| Injection volume | 20 µl |

A.1.3 Preparative HPLC

| Variable | Parameters |
|---|---|
| Device | Shimadzu LC-8A system |
| Column | Phenomenex Luna $C_8$(2) 100 Å, 5 µm column, 30 × 250 mm |
| Mobile phase | A: TFA, 0.1%(v/v) in $H_2O$; B: TFA, 0.09%(v/v) in methanol |
| Method | Linear gradient of 45% B in 120 min |
| Flow rate | 20.0 mL/min |
| Detection wavelength | UV 220 nm |
| Column temperature | 30° C. |

A.1.4 Mass Spectroscopy

Mass spectra were recorded on an Esquire HCT ESI-MS (Bruker Daltonics) or on an Agilent single quadrupole ESI-MS.

Abbreviations
Ac Acetyl
Amb(2-AMe[Boc]-5-Cl) (2-Aminomethyl-4-chlorobenzyl)-carbamic acid tert-butyl ester
Amb(2-AMe-5-Cl) 4-Chloro-1,2-benzenedimethanamine
Asp Aspartic acid
Aze Azetidine-2-carboxylic acid
Bn Benzyl
Boc tert.-Butyloxycarbonyl
Bzls Benzylsulfonyl CAS Chemical Abstracts Service registry number
Cbz Benzyloxycarbonyl
DCM Dichloromethane
DIEA Diisopropylethylamine
DMF N,N-Dimethylformamide
EDCxHCl 1-ethyl-3-(3-dimethylaminopropyl) carbodiimide hydrochloride
EtOH ethanol
Fmoc Fluorenylmethyloxycarbonyl
Glu Glutamic acid
HBTU O-Benzotriazole-N,N,N',N'-tetramethyl-uronium-hexafluoro-phosphate
HOBt Hydroxybenzotriazole
HPLC high performance liquid chromatography
Hyp 4-Hydroxypyrrolidine-2-carboxylic acid
iPrOH 2-propanol
mCPBA 3-Chloroperoxybenzoic acid
Me Methyl
MeOH methanol
MS mass spectroscopy
NMM N-Methylmorpholine
Pro Proline
PyBop benzotriazol-1-yl-oxytripyrrolidinophosphonium hexafluorophosphate
sat. saturated
tBu tert-Butyl
TEA Triethylamine
TFA Trifluoroacetic acid
THF tetrahydrofuran
TLC thin layer chromatography 1. Synthesis of Precursors:
1.1 Boc-D-Glu(morpholino)-OBn

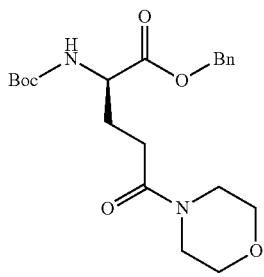 [SMILES: CC(C)(C)OC(=O)N[C@H](CCC(=O)N1CCOCC1)C(=O)OCc1ccccc1]

To a solution of Boc-D-Glu-OBn (3.4 g, 10.0 mmol) and morpholine (0.9 mL, 10.0 mmol) in dry DMF (60 mL) was added HBTU (4.2 g, 11.0 mmol) and DIEA (4.3 mL, 25.0 mmol) at 0° C. The mixture was stirred at 0° C. for 15 min and at room temperature for 2.0 h. The solvent was evaporated in vacuo, the residue dissolved in ethyl acetate and consecutively washed with aqueous 5% KHSO$_4$, saturated aqueous NaHCO$_3$, and brine. The organic layer was dried over Na$_2$SO$_4$ and the solvent evaporated in vacuo.

Yield: 4.4 g (>100%, white powder)
HPLC: 76.7% B HPLC 1; MS calc.: 406.5, found 407.1 (M+H)$^+$ 1.2 H-D-Glu(morpholino)-OBn×TFA

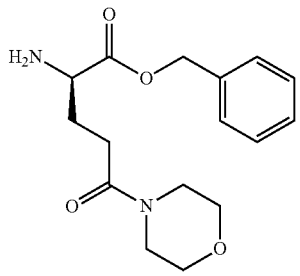 [SMILES: N[C@H](CCC(=O)N1CCOCC1)C(=O)OCc1ccccc1]

To a solution of compound 1.1 (4.1 g, 10.0 mmol) in DCM (10 mL) was added TFA (10 mL). The mixture was stirred at room temperature for 1.0 h. The solvent was evaporated in vacuo to obtain the crude title compound.

Yield: 4.0 g (98%, oil)
HPLC: 44.7% B HPLC 1; MS calc.: 306.2, found 307.0 (M+H)$^+$ 1.3 Bzls-D-Glu(morpholino)-OBn

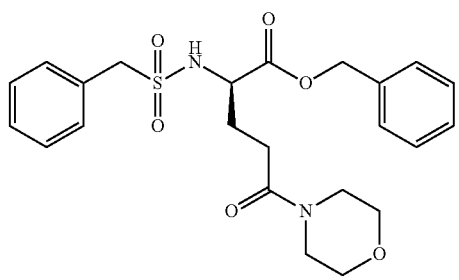 [SMILES: O=C(OCc1ccccc1)[C@@H](CCC(=O)N1CCOCC1)NS(=O)(=O)Cc1ccccc1]

To a solution of compound 1.2 (3.0 g, 7.1 mmol) in DCM (50 mL) was added Bzls-chloride (2.0 g, 10.7 mmol) and TEA (3.0 mL, 21.4 mmol) at 0° C. and the mixture was stirred for 3 h. The solvent was evaporated in vacuo, the residue dissolved in ethyl acetate, washed with aqueous 5% KHSO$_4$, saturated aqueous NaHCO$_3$ and brine. The organic layer was dried over Na$_2$SO$_4$ and concentrated to dryness in vacuo to afford the title compound.

Yield: 3.0 g (92%, oil).
HPLC: 73.4% B HPLC 1; MS calc.: 460.5, found 461.0 (M+H)$^+$ 1.4 Bzls-D-Glu(morpholino)-OH

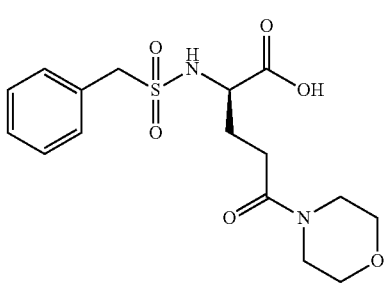 [SMILES: O=C(O)[C@@H](CCC(=O)N1CCOCC1)NS(=O)(=O)Cc1ccccc1]

To a solution of compound 1.3 (3.0 g, 6.5 mmol) in ethanol (30 mL) was added 10% Pd/C (30 mg) at room temperature under nitrogen. The nitrogen was replaced by hydrogen and the mixture stirred at room temperature 4 h. The mixture was flushed with nitrogen, filtered through Celite and the solvent was evaporated in vacuo to afford the crude title compound.

Yield: 2.3 g (95%, solid).

HPLC: 64.3% B HPLC 1; MS calc.: 370.4, found 370.9 (M+H)$^+$ 1.5 Bzls-D-Asp(1-Boc-piperazin-4-yl)-OBn

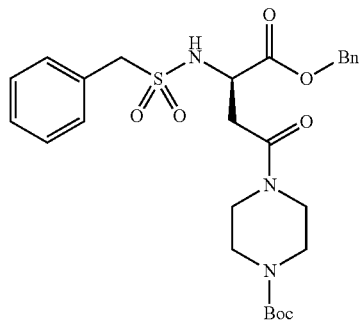 [SMILES: CC(C)(C)OC(=O)N1CCN(C(=O)C[C@@H](NS(=O)(=O)Cc2ccccc2)C(=O)OCc2ccccc2)CC1]

The title compound was prepared according to the procedure described for compound 1.1 using 1.24 (0.62 g, 1.65 mmol), Boc-piperazine and PyBop as coupling reagent.

Yield: 1.4 g (88%, white foam)

HPLC: 77.0% B HPLC 1; MS calc.: 545.2, found 544.0 (M−H)$^−$ 1.6 Bzls-D-Asp(1-Boc-piperazin-4-yl)-OH

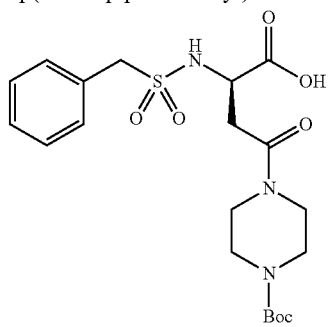

A mixture of benzyl ester 1.5 (1.42 g, 2.6 mmol) in dioxane (5 mL) and aqueous 1 M LiOH (5 mL) was stirred at room temperature for 4 h. The reaction was stopped by the addition of 5 mL 1N HCl, the solvent was evaporated in vacuo, the residue dissolved in ethyl acetate and consecutively washed with aqueous 5% KHSO$_4$, and brine. The organic layer was dried over over Na$_2$SO$_4$ and the solvent evaporated in vacuo to afford the title compound.

Yield: 1.1 g (90%, white foam)

HPLC: 63.9% B HPLC 1; MS calc.: 455.2, found 453.9 (M−H)$^−$

The compounds listed in Table 1 were prepared according to the procedure described for compound 1.1 and deprotection of the intermediates was done according to the procedure described for compound 1.2 or 1.4:

TABLE 1

| # | Structure | Precursors | MS calculated/ found | HPLC % B |
|---|---|---|---|---|
| 1.7 | 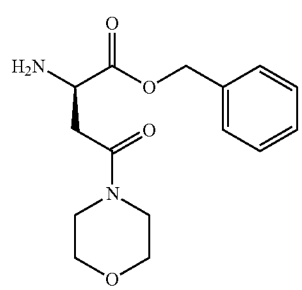 [SMILES: N[C@H](CC(=O)N1CCOCC1)C(=O)OCc1ccccc1] | a) Boc-D-Asp-OBn<br>b) Morpholine<br>deprotection performed<br>as for deprotection<br>performed as for 1.2 | 292.1/293.2<br>(M + H)$^+$ | 30.9<br>HPLC 2 |
| 1.8 | 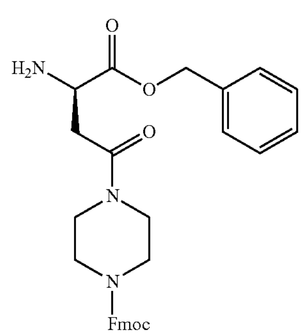 | a) Boc-D-Asp-OBn<br>b) Fmoc-Piperazine<br>deprotection performed<br>as for 1.2 | 513.2/514.3<br>(M + H)$^+$ | 86.9<br>HPLC 2 |

TABLE 1-continued

| # | Structure | Precursors | MS calculated/ found | HPLC % B |
|---|---|---|---|---|
| 1.9 | 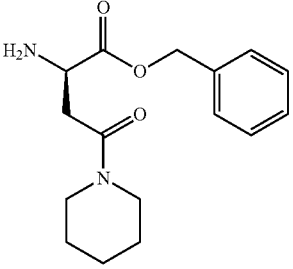 [SMILES: N[C@H](CC(=O)N1CCCCC1)C(=O)OCc1ccccc1] | a) Boc-D-Asp-OBn<br>b) Piperidine deprotection performed as for 1.2 | 290.2/291.1 $(M + H)^+$ | 48.5 HPLC 2 |
| 1.10 | 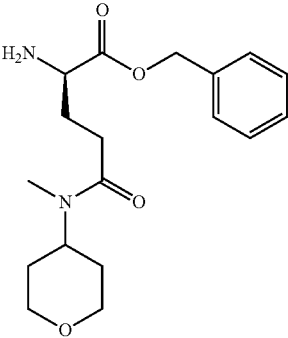 [SMILES: CN(C(=O)CC[C@@H](N)C(=O)OCc1ccccc1)C1CCOCC1] | a) Boc-D-Glu-OBn<br>b) CAS 220641-87-2 deprotection performed as for 1.2 | 334.2/335.1 $(M + H)^+$ | 26.8 HPLC 1 |
| 1.11 | 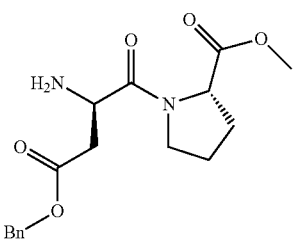 [SMILES: COC(=O)[C@@H]1CCCN1C(=O)[C@H](N)CC(=O)OCc1ccccc1] | a) Boc-D-Asp(OBn)-OH<br>b) H-Pro-OMe deprotection performed as for 1.2 | 334.2/335.1 $(M + H)^+$ | 28.6 HPLC 1 |
| 1.12 | 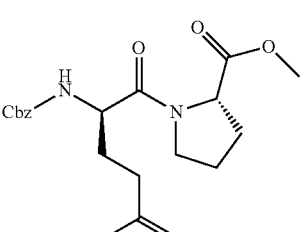 | a) Cbz-D-Glu(OtBu)-OH<br>b) H-Pro-OMe deprotection performed as for 1.2 | 392.2/415.0 $(M + Na)^+$ | 68.4 HPLC 1 |
| 1.13 | 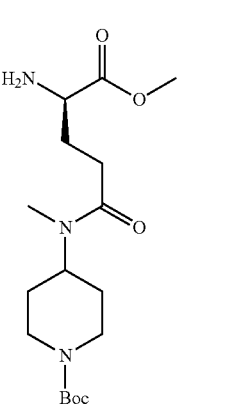 [SMILES: COC(=O)[C@H](N)CCC(=O)N(C)C1CCN(C(=O)OC(C)(C)C)CC1] | a) Cbz-D-Glu-OMe<br>b) 1-Boc-4-Methyl-aminopiperidine deprotection performed as for 1.4 | 357.2/358.1 $(M + Na)^+$ | 45.7 HPLC 1 |

The compounds listed in Table 2 were prepared according to the procedure described for compound 1.3 and deprotection of the intermediates were done according to procedure described for compound 1.2, 1.4 or 1.6:

TABLE 2

| # | Structure | Precursors | MS calculated/ found | HPLC % B |
|---|---|---|---|---|
| 1.14 | 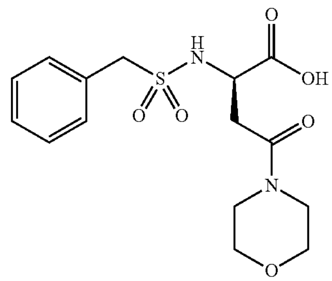 [SMILES: O=C(O)[C@@H](CC(=O)N1CCOCC1)NS(=O)(=O)Cc1ccccc1] | a) 1.7<br>b) Bzls-chloride deprotection performed as for 1.4 | 356.1/357.1 (M + H)+ | 56.0 HPLC 2 |
| 1.15 | 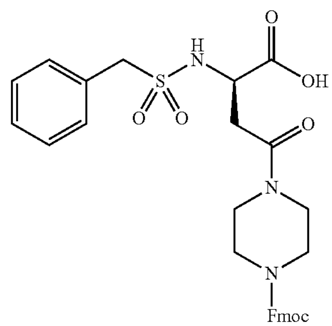 | a) 1.8<br>b) Bzls-chloride deprotection performed as for 1.4 | 577.2/578.2 (M + H)+ | 100.0 HPLC 2 |
| 1.16 | 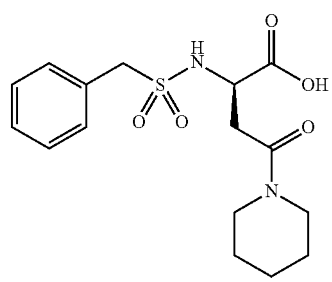 [SMILES: O=C(O)[C@@H](CC(=O)N1CCCCC1)NS(=O)(=O)Cc1ccccc1] | a) 1.9<br>b) Bzls-chloride deprotection performed as for 1.4 | 354.1/355.0 (M + H)+ | 74.1 HPLC 2 |
| 1.17 | 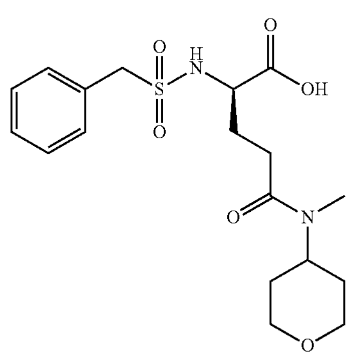 [SMILES: CN(C(=O)CC[C@@H](NS(=O)(=O)Cc1ccccc1)C(=O)O)C1CCOCC1] | a) 1.10<br>b) Bzls-chloride deprotection performed as for 1.6 | 398.2/397.0 (M − H)− | 64.1 HPLC 1 |

TABLE 2-continued

| # | Structure | Precursors | MS calculated/ found | HPLC % B |
|---|---|---|---|---|
| 1.18 | [structure] | a) 1.2<br>b) Phenacetyl chloride deprotection performed as for 1.4 using 1:1 ethanol/acetic acid as solvent | 334.2/335.0 (M + H)+ | 63.3 HPLC 1 |
| 1.19 | [structure] | a) H-D-Asp(OBn)-L-Pro-OMe<br>b) Bzls-chloride deprotection performed as for 1.4 | 398.1/399.0 (M + H)+ | 50.8 HPLC 1 |
| 1.20 | [structure] | a) 1.13<br>b) Bzls-chloride deprotection performed as for 1.6 | 497.2/496.1 (M − H)− | 71.0 HPLC 1 |

1.21 Bzls-D-Glu(OtBu)-OH

To a mixture of H-D-Glu(OtBu)-OH×H$_2$O (1.0 g, 4.5 mmol), aqueous 1M NaOH (4.5 mL, 4.5 mmol), dioxane (30 mL) and water (15 mL) was added a solution of Bzls-chloride (4.9 g, 25.8 mmol) in 30 portions over 24 h. The pH was maintained between 8-9 by addition of aqueous 1M NaOH. Stirring was continued until no more starting material was detected by TLC. The solvent was evaporated in vacuo and the residue portioned between ethyl acetate and aqueous 5% KHSO$_4$. The organic layer was washed with aqueous 5% KHSO$_4$ and brine, dried over Na$_2$SO$_4$, and evaporated in vacuo to afford the title compound.

Yield: 1.6 g (100%, white solid).

HPLC: 66.5% B HPLC 1; MS calc.: 357.1, found 355.8 (M−H)−

The compounds listed in Table 3 were prepared according to the procedure described for compound 1.21.

TABLE 3

| # | Structure | Precursors | MS calculated/ found | HPLC % B |
|---|---|---|---|---|
| 1.22 | 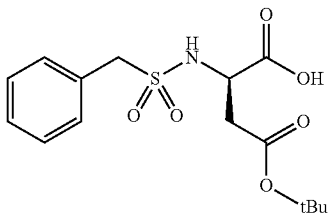 [SMILES: CC(C)(C)OC(=O)C[C@@H](NS(=O)(=O)Cc1ccccc1)C(=O)O] | a) H-D-Asp(OtBu)-OH<br>b) Bzls-chloride | 343.1/342.0<br>(M − H)⁻ | 34.4<br>HPLC 2 |
| 1.23 | 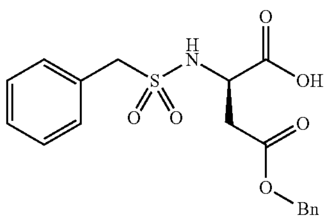 [SMILES: O=C(C[C@@H](NS(=O)(=O)Cc1ccccc1)C(=O)O)OCc1ccccc1] | a) H-D-Asp(OBn)-OH<br>b) Bzls-chloride | 377.1/375.9<br>(M − H)⁻ | 60.1<br>HPLC 1 |
| 1.24 | 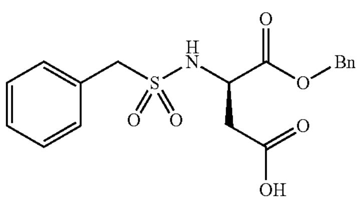 [SMILES: O=C(O)C[C@@H](NS(=O)(=O)Cc1ccccc1)C(=O)OCc1ccccc1] | a) H-D-Asp-OBn<br>b) Bzls-chloride | 377.1/377.8<br>(M + H)⁺ | 55.2<br>HPLC 1 |

1.25 Boc-D-Asp-L-Pro-OtBu

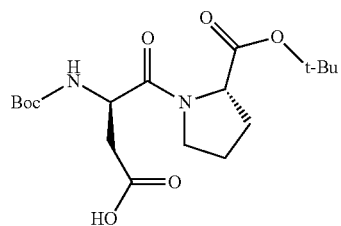 [SMILES: CC(C)(C)OC(=O)N[C@H](CC(=O)O)C(=O)N1CCC[C@H]1C(=O)OC(C)(C)C]

To a mixture of Boc-D-Asp(OBn)-OH (2.0 g, 6.2 mmol), L-Pro-OtBu (1.3 g, 6.2 mmol) and HOBt (125 mg, 0.9 mmol) in EtOH (15 mL) was added DIEA (2.4 mL, 13.6 mmol). The mixture was stirred to complete dissolution and cooled in an ice bath. EDC×HCl (1.4 g, 7.4 mmol) was added and the mixture was stirred at room temperature for 6.0 h. The mixture was concentrated in vacuo, taken up in 100 mL Ethyl acetate and 50 mL 5% NaH₂PO₄. The organic layer was collected, washed with 50 mL 5% NaH₂PO₄ and 2×50 mL saturated NaHCO₃, dried over Na₂SO₄ and concentrated in vacuo. After purification by SiO₂ chromatography (1% TEA in DCM), deprotection of the resulting intermediate was done according to procedure described for compound 1.4 using MeOH as solvent to afford the title compound.

Yield: 1.82 g (72%, white foam)

HPLC: 93.3% B HPLC 2; MS calc.: 386.2, found 385.0 (M−H)⁻

1.26 H-D-Asp(4-amino-pyridine)-L-Pro-OH

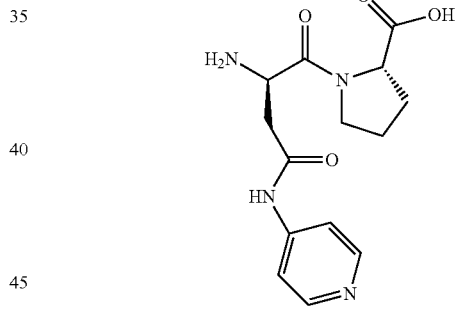

To a solution of compound 1.25 (908 mg, 2.4 mmol) in THF (40 mL) was added TEA (360 µl, 2.6 mmol). At −10° C. (bath temperature) isobutyl chloroformate (307 µl, 2.4 mmol) was added dropwise. The mixture was stirred for 1 h at −10° C. 4-Aminopyridine (221 mg, 2.4 mmol) was added in one portion. The mixture was left to come to room temperature on its own and stir there for a total of 6 h. The volatiles were removed in vacuo. The mixture was dissolved in 100 mL of ethyl acetate, followed by 50 mL of saturated NaHCO₃. The pH was adjusted to 9 with Na₂CO₃. The organic layer was separated, and the aqueous layer was extracted with 3×50 mL of 4:1 CHCl₃:iPrOH. The combined organics were dried over Na₂SO₄, filtered through a pad of 1:1 SiO₂:celite and concentrated in vacuo. The resulting intermediate was deprotected according to the procedure described for compound 1.2 to afford the title compound, which was used directly in the next step.

Yield: not applicable (used crude, syrup).

HPLC: 34.6% B HPLC 2; MS calc.: 306.1, found 307.0 (M+H)⁺

1.27 Bzls-D-Asp(4-amino-pyridine)-L-Pro-OH

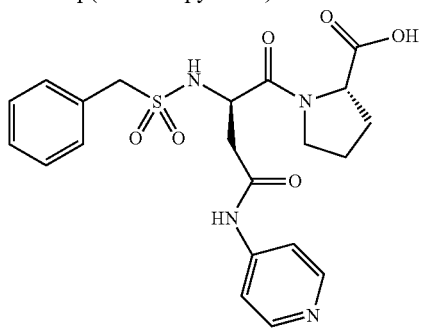

Compound 1.27 was prepared according to the procedure described for compound 1.21 using the crude intermediate 1.26 without workup. The resulting crude intermediate was used directly in the next step.

Yield: not applicable (used crude, gum).

HPLC: 37.4% B HPLC 2; MS calc.: 460.1, found 461.2 $(M+H)^+$

The compounds listed in Table 4 were prepared according to the procedure described for compound 1.1 and deprotection of the intermediates was done according to procedure described for compound 1.2, 1.4 or 1.6:

TABLE 4

| # | Structure | Precursors | MS calculated/ found | HPLC % B |
|---|---|---|---|---|
| 1.28 | 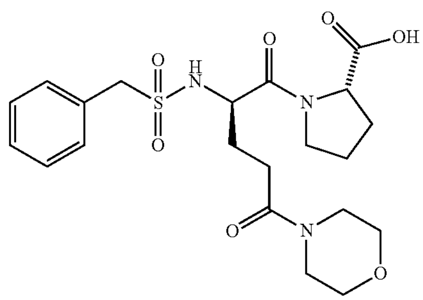 [SMILES: O=C(O)[C@@H]1CCCN1C(=O)[C@@H](CCC(=O)N1CCOCC1)NS(=O)(=O)Cc1ccccc1] | a) 1.4<br>b) H-L-Pro-OMe<br>deprotection performed as for 1.6 | 467.2/468.0<br>$(M + H)^+$ | 68.7<br>HPLC 1 |
| 1.29 | 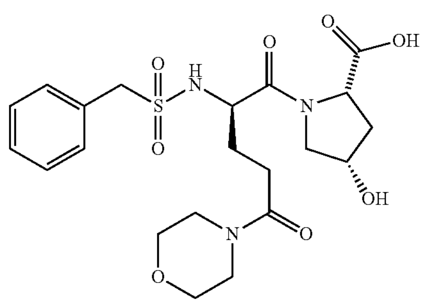 [SMILES: O=C(O)[C@@H]1C[C@H](O)CN1C(=O)[C@@H](CCC(=O)N1CCOCC1)NS(=O)(=O)Cc1ccccc1] | a) 1.4<br>b) H-cis-Hyp-OMe × HCl<br>deprotection performed as for 1.6 | 483.2/481.9<br>$(M - H)^-$ | 60.5<br>HPLC 1 |
| 1.30 | 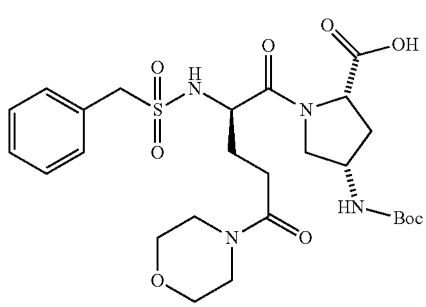 [SMILES: CC(C)(C)OC(=O)N[C@H]1C[C@@H](C(=O)O)N(C(=O)[C@@H](CCC(=O)N2CCOCC2)NS(=O)(=O)Cc2ccccc2)C1] | a) 1.4<br>b) CAS 168263-82-9<br>deprotection performed as for 1.6 | 582.2/581.1<br>$(M - H)^-$ | 68.2<br>HPLC 1 |

TABLE 4-continued

| # | Structure | Precursors | MS calculated/ found | HPLC % B |
|---|---|---|---|---|
| 1.31 | 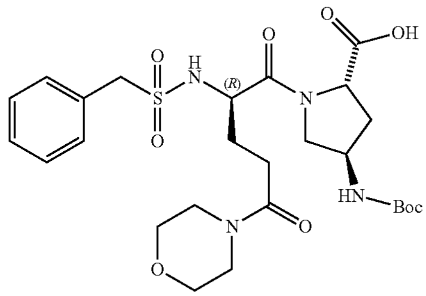 | a) 1.4<br>b) CAS 473806-21-2<br>deprotection performed as for 1.6 | 582.2/583.2<br>(M + H)⁺ | 64.8<br>HPLC 1 |
| 1.32 | 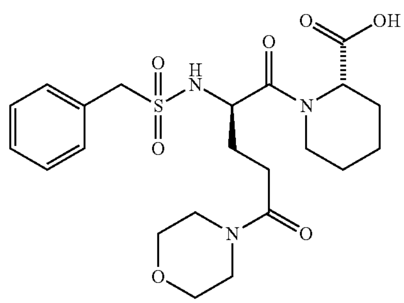 [SMILES: O=C(O)[C@@H]1CCCCN1C(=O)[C@@H](CCC(=O)N1CCOCC1)NS(=O)(=O)Cc1ccccc1] | a) 1.4<br>b) CAS 18650-39-0<br>deprotection performed as for 1.6 | 481.2/482.2<br>(M + H)⁺ | 74.0<br>HPLC 2 |
| 1.33 | 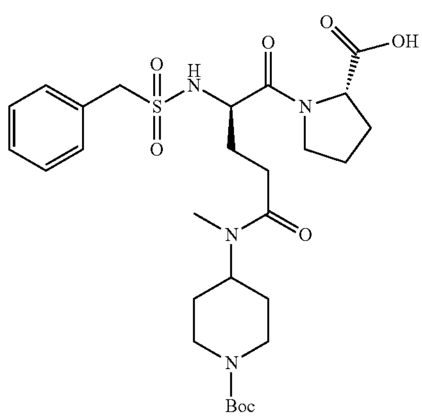 [SMILES: CN(C(=O)CC[C@@H](NS(=O)(=O)Cc1ccccc1)C(=O)N1CCC[C@H]1C(=O)O)C1CCN(C(=O)OC(C)(C)C)CC1] | a) 1.20<br>b) H-L-Pro-OMe<br>deprotection performed as for 1.6 | 594.3/617.1<br>(M + Na)⁺ | 69.88<br>HPLC 1 |
| 1.34 | 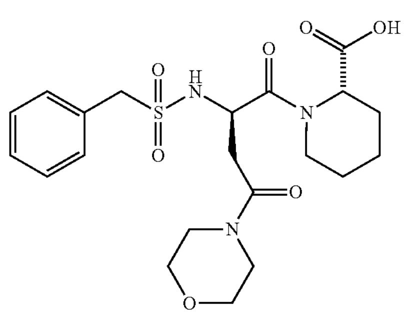 [SMILES: O=C(O)[C@@H]1CCCCN1C(=O)[C@@H](CC(=O)N1CCOCC1)NS(=O)(=O)Cc1ccccc1] | a) 1.14<br>b) CAS 18650-39-0<br>deprotection performed as for 1.6 | 467.2/468.1<br>(M + H)⁺ | 73.1<br>HPLC 2 |

TABLE 4-continued

| # | Structure | Precursors | MS calculated/ found | HPLC % B |
|---|---|---|---|---|
| 1.35 | 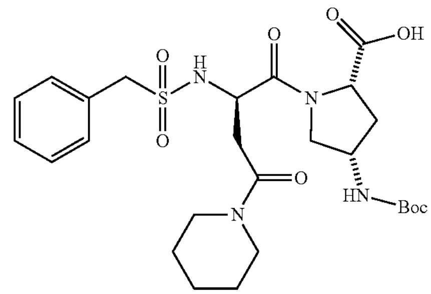 [SMILES: CC(C)(C)OC(=O)N[C@H]1C[C@@H](C(=O)O)N(C(=O)[C@@H](CC(=O)N2CCCCC2)NS(=O)(=O)Cc2ccccc2)C1] | a) 1.16<br>b) CAS 168263-82-9 deprotection performed as for 1.6 | 566.2/567.1 (M + H)+ | 90.7 HPLC 2 |
| 1.36 | 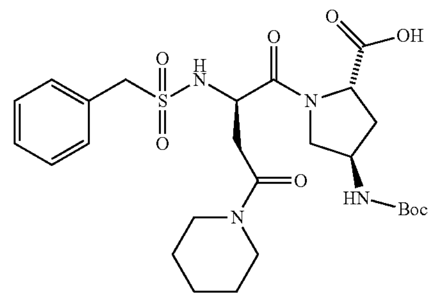 [SMILES: CC(C)(C)OC(=O)N[C@@H]1C[C@@H](C(=O)O)N(C(=O)[C@@H](CC(=O)N2CCCCC2)NS(=O)(=O)Cc2ccccc2)C1] | a) 1.16<br>b) CAS 473806-21-2 deprotection performed as for 1.6 | 566.2/567.1 (M + H)+ | 92.9 HPLC 2 |
| 1.37 | 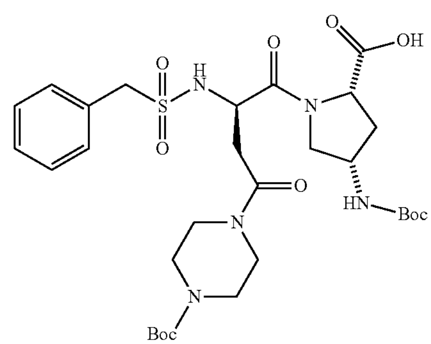 [SMILES: CC(C)(C)OC(=O)N[C@H]1C[C@@H](C(=O)O)N(C(=O)[C@@H](CC(=O)N2CCN(C(=O)OC(C)(C)C)CC2)NS(=O)(=O)Cc2ccccc2)C1] | a) 1.6<br>b) CAS 168263-82-9 deprotection performed as for 1.6 | 667.3/668.1 (M + H)+ | 74.9% B HPLC 1 |
| 1.38 | 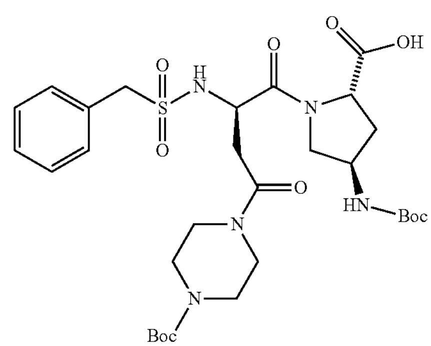 [SMILES: CC(C)(C)OC(=O)N[C@@H]1C[C@@H](C(=O)O)N(C(=O)[C@@H](CC(=O)N2CCN(C(=O)OC(C)(C)C)CC2)NS(=O)(=O)Cc2ccccc2)C1] | a) 1.6<br>b) CAS 473806-21-2 deprotection performed as for 1.6 | 667.3/668.1 (M + H)+ | 74.9% B HPLC 18 |
| 1.39 | 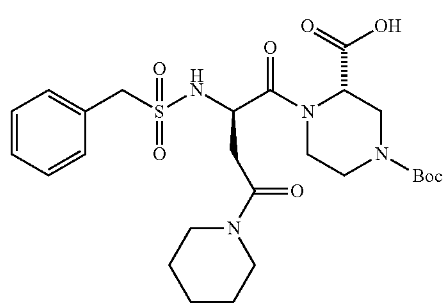 [SMILES: CC(C)(C)OC(=O)N1CCN(C(=O)[C@@H](CC(=O)N2CCCCC2)NS(=O)(=O)Cc2ccccc2)[C@H](C(=O)O)C1] | a) 1.16<br>b) CAS 314741-39-4 deprotection performed as for 1.6 | 566.2/567.1 (M + H)+ | 91.0 HPLC 2 |

TABLE 4-continued

| # | Structure | Precursors | MS calculated/found | HPLC % B |
|---|---|---|---|---|
| 1.40 | 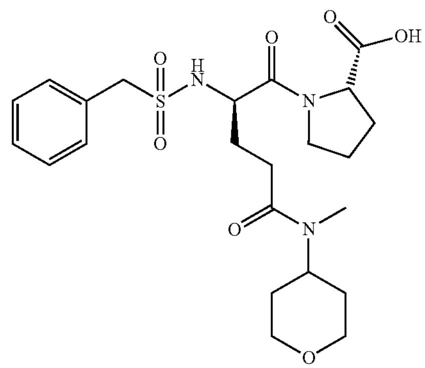 | a) 1.17<br>b) H-L-Pro-OtBu deprotection performed as for 1.2 | 495.2/496.1 $(M + H)^+$ | 52.6 HPLC 1 |
| 1.41 | 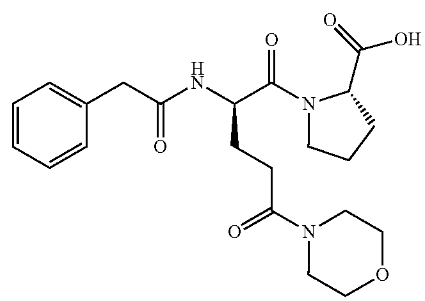 [SMILES: O=C(Cc1ccccc1)N[C@H](CCC(=O)N1CCOCC1)C(=O)N1CCC[C@H]1C(=O)O] | a) 1.18<br>b) H-L-Pro-OtBu deprotection performed as for 1.2 | 431.2/429.9 $(M - H)^-$ | 61.2 HPLC 1 |
| 1.42 | 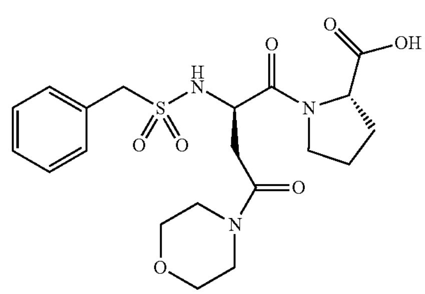 [SMILES: O=C(O)[C@@H]1CCCN1C(=O)[C@@H](CC(=O)N1CCOCC1)NS(=O)(=O)Cc1ccccc1] | a) 1.14<br>b) H-L-Pro-OtBu deprotection performed as for 1.2 | 453.2/452.4 $(M - H)^-$ | 51.0 HPLC 1 |
| 1.43 | 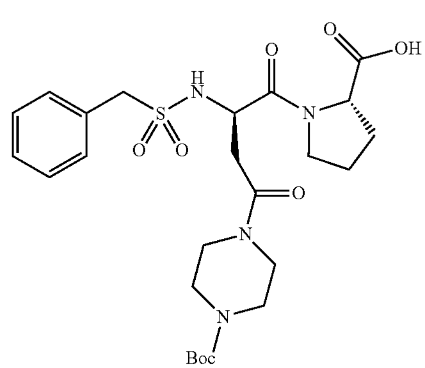 [SMILES: CC(C)(C)OC(=O)N1CCN(C(=O)C[C@@H](NS(=O)(=O)Cc2ccccc2)C(=O)N2CCC[C@H]2C(=O)O)CC1] | a) 1.19<br>b) Boc-Piperazine deprotection performed as for 1.6 | 552.2/551.1 $(M - H)^-$ | 55.7 HPLC 1 |

TABLE 4-continued

| # | Structure | Precursors | MS calculated/found | HPLC % B |
|---|---|---|---|---|
| 1.44 | 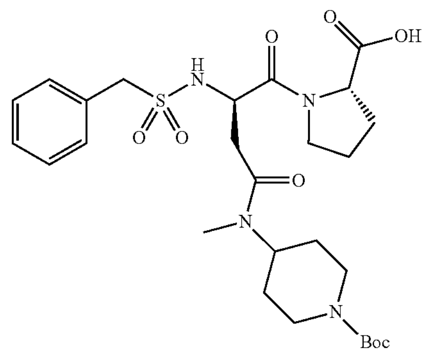 [SMILES: CN(C(=O)C[C@@H](NS(=O)(=O)Cc1ccccc1)C(=O)N1CCC[C@H]1C(=O)O)C1CCN(C(=O)OC(C)(C)C)CC1] | a) 1.19<br>b) Boc-4-Methylamino-piperidine deprotection performed as for 1.6 | 580.3/579.1<br>(M − H)⁻ | 55.2<br>HPLC 1 |
| 1.45 | 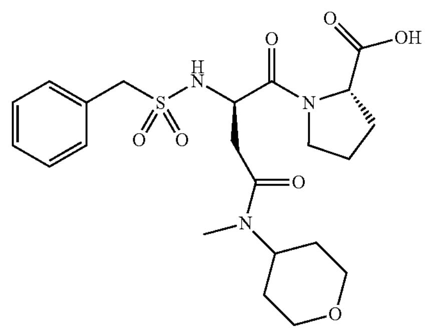 [SMILES: CN(C(=O)C[C@@H](NS(=O)(=O)Cc1ccccc1)C(=O)N1CCC[C@H]1C(=O)O)C1CCOCC1] | a) 1.19<br>b) CAS 220641-87-2 deprotection performed as for 1.6 | 481.2/482.1<br>(M + H)⁺ | 52.8<br>HPLC 1 |
| 1.46 | 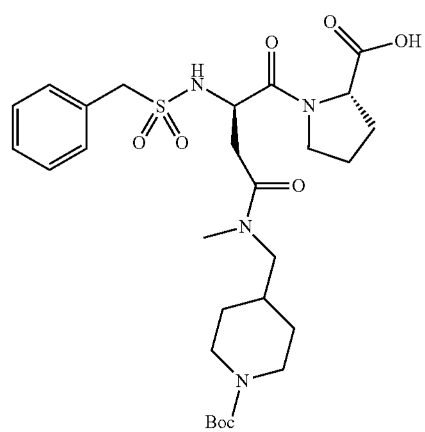 [SMILES: CN(CC1CCN(C(=O)OC(C)(C)C)CC1)C(=O)C[C@@H](NS(=O)(=O)Cc1ccccc1)C(=O)N1CCC[C@H]1C(=O)O] | a) 1.19<br>b) CAS 138022-02-3 deprotection performed as for 1.6 | 594.3/595.3<br>(M + H)⁺ | 92.8<br>HPLC 2 |
| 1.47 | 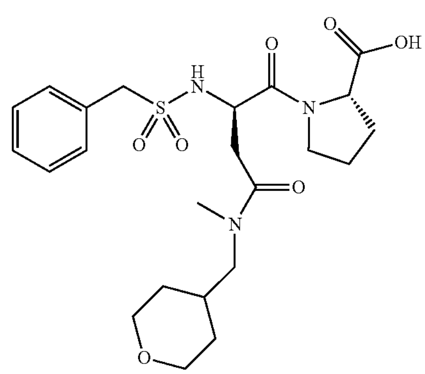 [SMILES: CN(CC1CCOCC1)C(=O)C[C@@H](NS(=O)(=O)Cc1ccccc1)C(=O)N1CCC[C@H]1C(=O)O] | a) 1.19<br>b) CAS 439081-52-4 deprotection performed as for 1.6 | 495.2/496.3<br>(M + H)⁺ | 74.6<br>HPLC 2 |

TABLE 4-continued

| # | Structure | Precursors | MS calculated/ found | HPLC % B |
|---|---|---|---|---|
| 1.48 | 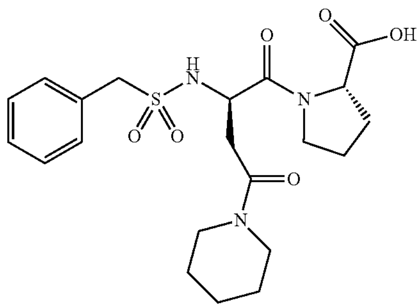 [SMILES: O=C(O)[C@@H]1CCCN1C(=O)[C@@H](CC(=O)N1CCCCC1)NS(=O)(=O)Cc1ccccc1] | a) 1.19<br>b) Piperidine deprotection performed as for 1.6 | 451.2/452.2<br>(M + H)+ | 78.4<br>HPLC 2 |
| 1.49 | 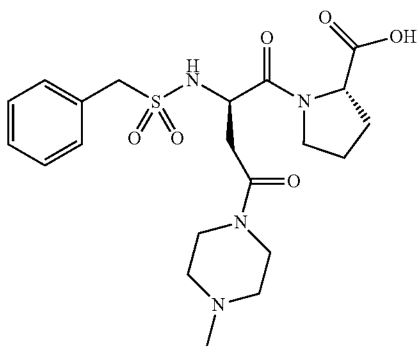 [SMILES: CN1CCN(C(=O)C[C@@H](NS(=O)(=O)Cc2ccccc2)C(=O)N2CCC[C@H]2C(=O)O)CC1] | a) 1.19<br>b) 1-Methyl-piperazine deprotection performed as for 1.6 | 466.2/467.3<br>(M + H)+ | 53.2<br>HPLC 1 |
| 1.50 | 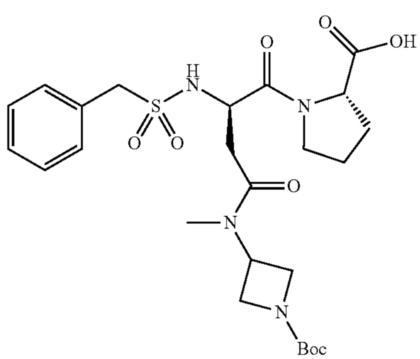 [SMILES: CN(C(=O)C[C@@H](NS(=O)(=O)Cc1ccccc1)C(=O)N1CCC[C@H]1C(=O)O)C1CN(C(=O)OC(C)(C)C)C1] | a) 1.19<br>b) CAS 454703-20-9 deprotection performed as for 1.6 | 552.2/551.2<br>(M − H)− | 46.3<br>HPLC 1 |
| 1.51 | 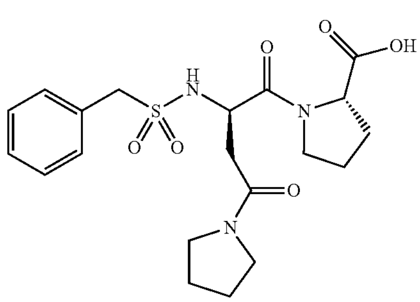 [SMILES: O=C(O)[C@@H]1CCCN1C(=O)[C@@H](CC(=O)N1CCCC1)NS(=O)(=O)Cc1ccccc1] | a) 1.19<br>b) Pyrrolidine deprotection performed as for 1.6 | 437.2/435.9<br>(M − H)− | 50.2<br>HPLC 1 |

TABLE 4-continued

| # | Structure | Precursors | MS calculated/ found | HPLC % B |
|---|---|---|---|---|
| 1.52 | 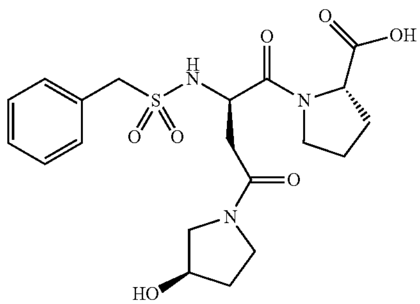 [SMILES: O=C(O)[C@@H]1CCCN1C(=O)[C@@H](CC(=O)N1CC[C@@H](O)C1)NS(=O)(=O)Cc1ccccc1] | a) 1.19<br>b) (R)-3-Pyrrolidinol deprotection performed as for 1.6 | 453.2/454.13<br>(M + H)+ | 46.4<br>HPLC 1 |
| 1.53 | 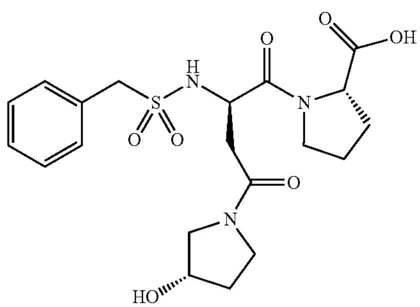 [SMILES: O=C(O)[C@@H]1CCCN1C(=O)[C@@H](CC(=O)N1CC[C@H](O)C1)NS(=O)(=O)Cc1ccccc1] | a) 1.19<br>b) (S)-3-Pyrrolidinol deprotection performed as for 1.6 | 453.2/454.0<br>(M + H)+ | 46.3<br>HPLC 1 |
| 1.54 | 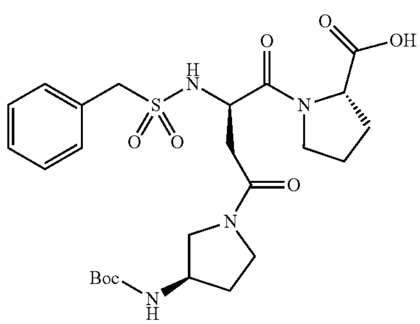 [SMILES: CC(C)(C)OC(=O)N[C@@H]1CCN(C(=O)C[C@@H](NS(=O)(=O)Cc2ccccc2)C(=O)N2CCC[C@H]2C(=O)O)C1] | a) 1.19<br>b) (R)-3-(Boc-amino)pyrrolidine deprotection performed as for 1.6 | 552.2/551.0<br>(M − H)− | 65.0<br>HPLC 1 |
| 1.55 | 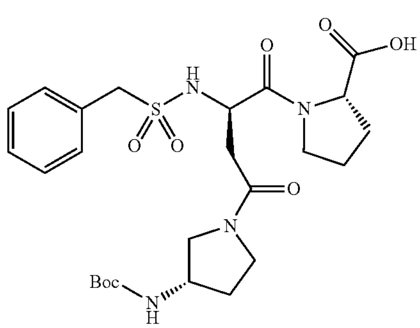 [SMILES: CC(C)(C)OC(=O)N[C@H]1CCN(C(=O)C[C@@H](NS(=O)(=O)Cc2ccccc2)C(=O)N2CCC[C@H]2C(=O)O)C1] | a) 1.19<br>b) (S)-3-(Boc-amino)pyrrolidine deprotection performed as for 1.6 | 552.2/551.0<br>(M − H)− | 64.7<br>HPLC 1 |
| 1.56 | 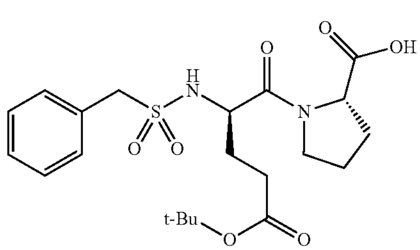 [SMILES: CC(C)(C)OC(=O)CC[C@@H](NS(=O)(=O)Cc1ccccc1)C(=O)N1CCC[C@H]1C(=O)O] | a) 1.21<br>b) H-L-Pro-OMe deprotection performed as for 1.6 | 454.2/455.1<br>(M + H)+ | 67.9<br>HPLC 1 |

TABLE 4-continued

| # | Structure | Precursors | MS calculated/ found | HPLC % B |
|---|---|---|---|---|
| 1.57 | 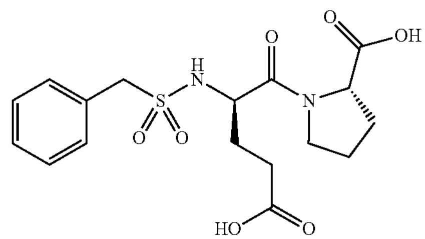 [SMILES: O=C(O)CC[C@@H](NS(=O)(=O)Cc1ccccc1)C(=O)N1CCC[C@H]1C(=O)O] | byproduct of 1.56 | 398.1/399.0 (M + H)+ | 59.2 HPLC 1 |
| 1.58 | 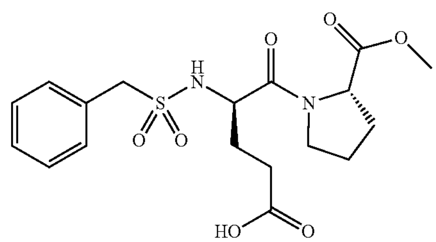 [SMILES: COC(=O)[C@@H]1CCCN1C(=O)[C@@H](CCC(=O)O)NS(=O)(=O)Cc1ccccc1] | a) 1.21 b) H-L-Pro-OMe deprotection performed as for 1.2 | 468.2/491.1 (M + Na)+ | 71.8 HPLC 1 |
| 1.59 | 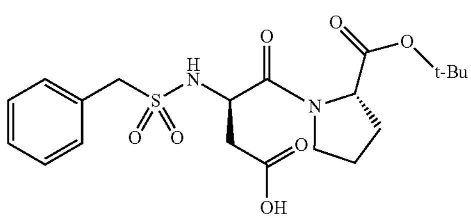 [SMILES: CC(C)(C)OC(=O)[C@@H]1CCCN1C(=O)[C@@H](CC(=O)O)NS(=O)(=O)Cc1ccccc1] | a) 1.23 b) H-L-Pro-OtBu deprotection performed as for 1.4 (60° C. instead of room temperature) | 440.2/439.3 (M − H)− | 71.1 HPLC 1 |
| 1.60 | 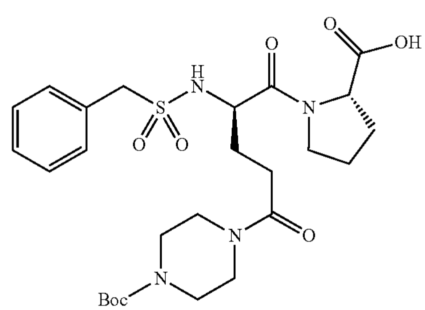 [SMILES: CC(C)(C)OC(=O)N1CCN(C(=O)CC[C@@H](NS(=O)(=O)Cc2ccccc2)C(=O)N2CCC[C@H]2C(=O)O)CC1] | a) 1.58 b) H-L-Pro-OMe deprotection performed as for 1.6 | 566.2/567.0 (M + H)+ | 64.6 HPLC 1 |
| 1.61 | 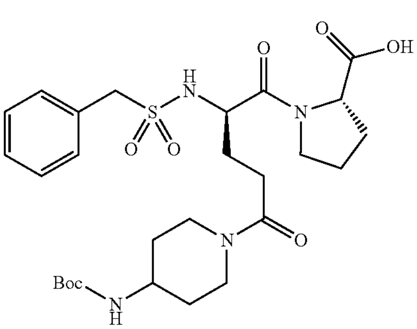 [SMILES: CC(C)(C)OC(=O)NC1CCN(C(=O)CC[C@@H](NS(=O)(=O)Cc2ccccc2)C(=O)N2CCC[C@H]2C(=O)O)CC1] | a) 1.58 b) 4-N-Boc-Aminopiperidin deprotection performed as for 1.6 | 580.3/579.1 (M − H)− | 60.2 HPLC 1 |

TABLE 4-continued

| # | Structure | Precursors | MS calculated/ found | HPLC % B |
|---|---|---|---|---|
| 1.62 | 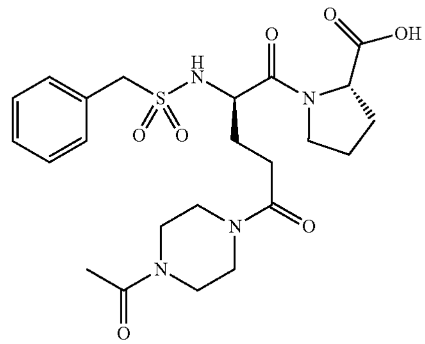 [SMILES: CC(=O)N1CCN(C(=O)CC[C@@H](NS(=O)(=O)Cc2ccccc2)C(=O)N2CCC[C@H]2C(=O)O)CC1] | a) 1.59<br>b) Acetyl-piperazine deprotection performed as for 1.2 | 494.2/492.9<br>(M − H)⁻ | 51.8<br>HPLC 1 |
| 1.63 | 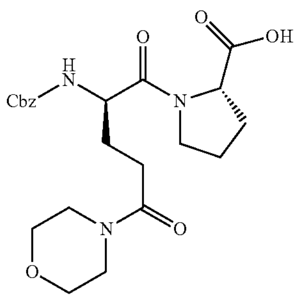 [SMILES: O=C(N[C@H](CCC(=O)N1CCOCC1)C(=O)N1CCC[C@H]1C(=O)O)OCc1ccccc1] | a) 1.12<br>b) Morpholine deprotection performed as for 1.6 | 447.2/470.1<br>(M + Na)⁺ | 54.8<br>HPLC 1 |

1.64  Bzls-D-Asp(N-[1-Ac-Piperidin-4-yl]-N-[methyl]amid)-L-Pro-OMe

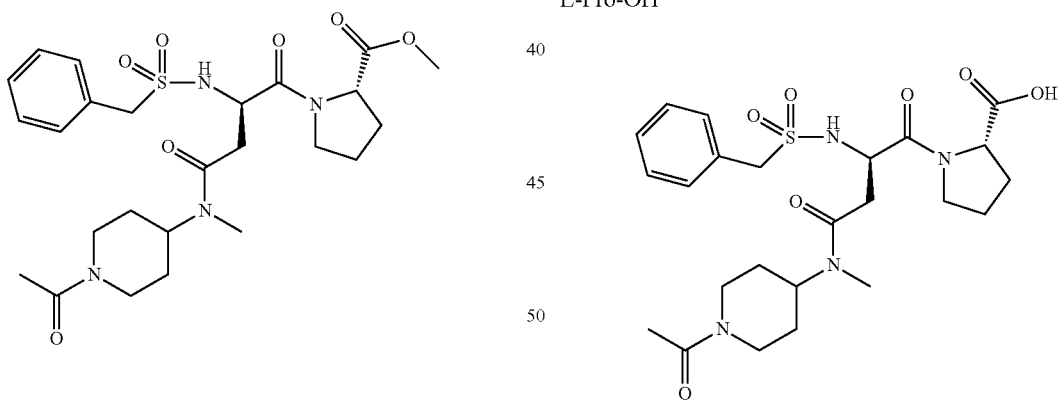

The methyl ester precursor to 1.44 was deprotected according to 1.2. To a solution of the resulting intermediate (470 mg, 0.8 mmol) in DCM (50 mL) was added TEA (0.6 mL, 4.5 mmol) and acetic anhydride (181 mg, 1.7 mmol). The mixture was stirred at room temperature for 3.0 h. The solvent was evaporated in vacuo, the residue dissolved in ethyl acetate and consecutively washed with aqueous 5% $KHSO_4$, saturated aqueous $NaHCO_3$, and brine. The organic layer was dried over $Na_2SO_4$ and the solvent evaporated in vacuo to afford the title compound.

Yield: 413 mg (100%, oil)

HPLC: 51.7% B HPLC 1; MS calc.: 536.2, found 537.2 (M+H)⁺

1.65 Bzls-D-Asp(N-(1-Ac-Piperidin-4-yl)-N-aminomethyl)-L-Pro-OH

Compound 1.64 (780 mg, 1.5 mmol) was converted to the title compound according to the procedure described for compound 1.6.

Yield: 135 mg (18%, oil)

HPLC: 51.7% B HPLC 1; MS calc.: 522.2, found 523.2 (M+H)⁺

The compounds listed in Table 5 were prepared according to the procedure described for compound 1.64 and following deprotection according to the procedure described for compound 1.6:

TABLE 5

| # | Structure | Precursors | MS calculated/found | HPLC % B |
|---|---|---|---|---|
| 1.66 | 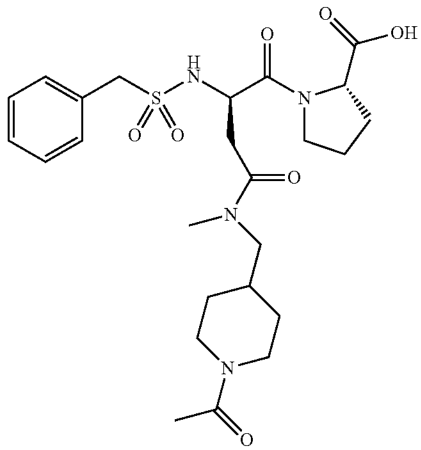 [SMILES: CC(=O)N1CCC(CN(C)C(=O)C[C@@H](NS(=O)(=O)Cc2ccccc2)C(=O)N2CCC[C@H]2C(=O)O)CC1] | a) methyl ester precursor to 1.46<br>b) acetyl chloride | 536.2/537.1<br>(M + H)+ | 72.0<br>HPLC 2 |
| 1.67 | 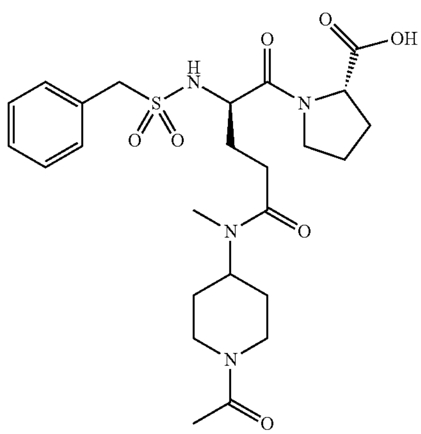 [SMILES: CC(=O)N1CCC(N(C)C(=O)CC[C@@H](NS(=O)(=O)Cc2ccccc2)C(=O)N2CCC[C@H]2C(=O)O)CC1] | a) methyl ester precursor to 1.33<br>b) acetic anhydride | 536.2/537.2<br>(M + H)+ | 50.0<br>HPLC 1 |

1.68 Bzls-D-Asp(thiomorpholino)-L-Pro-OtBu

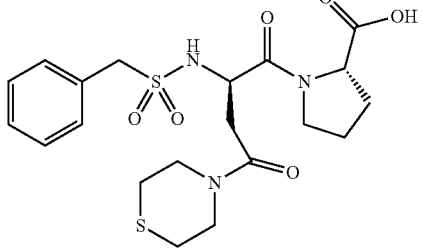

Compound 1.59 (442 mg, 1.0 mmol) and thiomorpholine were coupled according to the procedure described for compound 1.1 using PyBop as coupling reagent, and the resulting intermediate was converted to the title compound according to the procedure described for compound 1.2.

Yield: 465 mg (99%, oil)

HPLC: 58.4% B HPLC 1; MS calc.: 469.1, found 467.9 (M−H)−

1.69 Bzls-D-Asp(1-oxido-thiomorpholin-4-yl)-L-Pro-OtBu

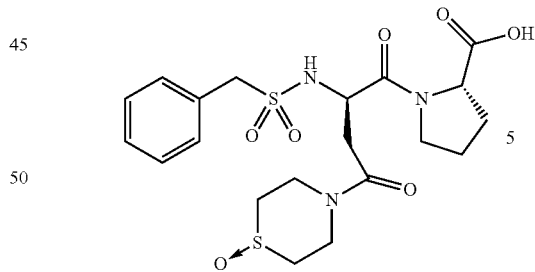

To a solution of the tert-butyl ester precursor to 1.68 (205 mg, 0.4 mmol) in EtOH (5 mL) was added NaIO$_4$ (111 mg, 0.5 mmol) at 0° C. The mixture was stirred for 1 h at 0° C. and then at room temperature overnight. The mixture was dissolved in 150 mL of ethyl acetate and 80 mL water. The organic layer was separated and washed with 3×50 mL water and 2×50 mL saturated brine, dried over Na$_2$SO$_4$, and evaporated in vacuo. The resulting intermediate was converted to the title compound according to the procedure described for compound 1.2.

Yield: 150 mg (77%, oil)

HPLC: 50.4% B HPLC 1; MS calc.: 485.1, found 483.9 (M−H)−

1.70 Bzls-D-Asp(1,1-dioxido-thiomorpholin-4-yl)-L-Pro-OtBu

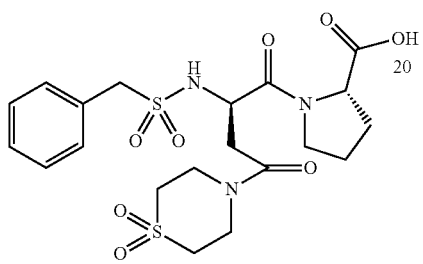 [SMILES: O=C(O)[C@@H]1CCCN1C(=O)[C@@H](CC(=O)N1CCS(=O)(=O)CC1)NS(=O)(=O)Cc1ccccc1]

To a solution of the tert-butyl ester precursor to 1.68 (208 mg, 0.4 mmol) in DCM (5 mL) was added 75% mCPBA (191 mg, 0.8 mmol) at room temperature and the mixture was stirred for 4 d. The mixture was dissolved in 50 mL DCM and 50 mL water. The organic layer was separated and washed with 2×50 mL NaHSO₃, 3×50 mL sat. NaHCO₃ and 2×50 mL brine, dried over Na₂SO₄ and evaporated in vacuo. The resulting intermediate was converted to the title compound according to the procedure described for compound 1.2.

Yield: 52 mg (26%, solid)

HPLC: 57.1% B HPLC 1; MS calc.: 501.1, found 499.9 (M−H)⁻

2. Synthesis of the Inhibitors 2.1 Bzls-D-Glu(morpholino)-L-Pro-Amb(2-AMe-5-Cl)×1 TFA

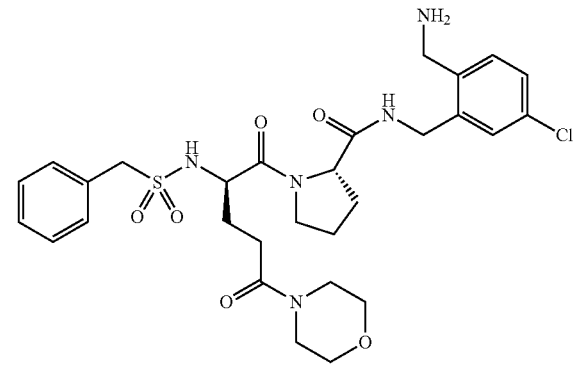 [SMILES: NCc1ccc(Cl)cc1CNC(=O)[C@@H]1CCCN1C(=O)[C@@H](CCC(=O)N1CCOCC1)NS(=O)(=O)Cc1ccccc1]

Compound 1.28 (193 mg, 0.41 mmol) and (2-Aminomethyl-4-chlorobenzyl)-carbamic acid tert-butyl ester (CAS 439116-15-1) were coupled according to the procedure described for compound 1.1. The resulting intermediate was deprotected according to the procedure described for compound 1.2 and purified by preparative reversed phase HPLC to afford the title compound.

Yield: 170 mg (56%, white solid)

HPLC: 52.2% B HPLC 1; MS calc.: 619.2, found 620.3 (M+H)⁺

The compounds listed in Table 6 were prepared according to the procedure described for compound 2.1:

TABLE 6

| # | Structure | Precursors | MS calculated/ found | HPLC % B |
|---|---|---|---|---|
| 2.2 | 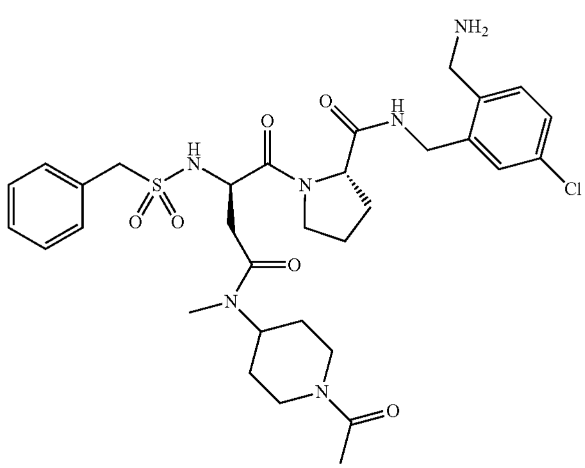 [SMILES: CC(=O)N1CCC(N(C)C(=O)C[C@@H](NS(=O)(=O)Cc2ccccc2)C(=O)N2CCC[C@H]2C(=O)NCc2cc(Cl)ccc2CN)CC1] | a) 1.65 | 674.3/675.3 (M + H)⁺ | 56.6 HPLC 1 |

TABLE 6-continued

| # | Structure | Precursors | MS calculated/ found | HPLC % B |
|---|---|---|---|---|
| 2.3 | 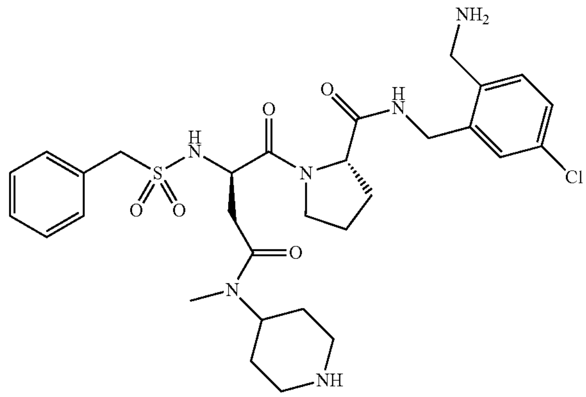 [SMILES: CN(C(=O)C[C@@H](NS(=O)(=O)Cc1ccccc1)C(=O)N1CCC[C@H]1C(=O)NCc1cc(Cl)ccc1CN)C1CCNCC1] | a) 1.44 | 632.3/633.2 (M + H)+ | 49.0 HPLC 1 |
| 2.4 | 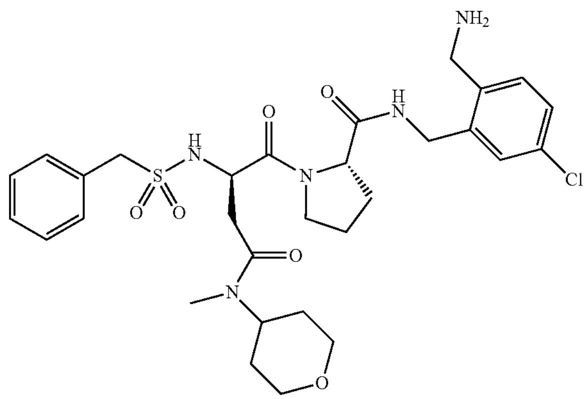 [SMILES: CN(C(=O)C[C@@H](NS(=O)(=O)Cc1ccccc1)C(=O)N1CCC[C@H]1C(=O)NCc1cc(Cl)ccc1CN)C1CCOCC1] | a) 1.45 | 633.2/634.2 (M + H)+ | 54.8 HPLC 1 |
| 2.5 | 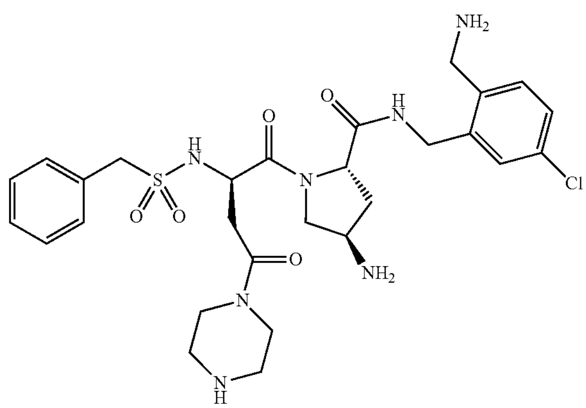 [SMILES: NCc1ccc(Cl)cc1CNC(=O)[C@@H]1C[C@@H](N)CN1C(=O)[C@@H](CC(=O)N1CCNCC1)NS(=O)(=O)Cc1ccccc1] | a) 1.38 | 619.2/620.2 (M + H)+ | 38.3 HPLC 1 |
| 2.6 | 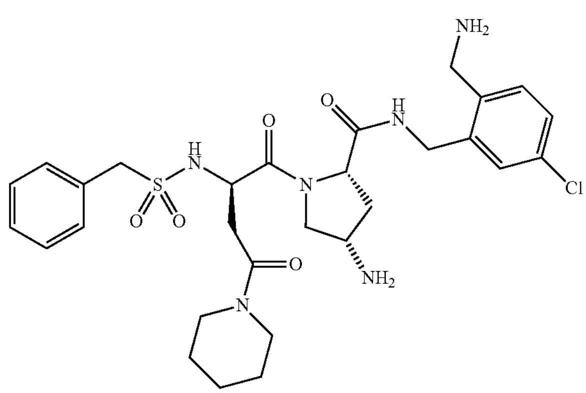 [SMILES: NCc1ccc(Cl)cc1CNC(=O)[C@@H]1C[C@H](N)CN1C(=O)[C@@H](CC(=O)N1CCCCC1)NS(=O)(=O)Cc1ccccc1] | a) 1.35 | 618.2/619.0 (M + H)+ | 60.8 HPLC 2 |

TABLE 6-continued

| # | Structure | Precursors | MS calculated/ found | HPLC % B |
|---|---|---|---|---|
| 2.7 | 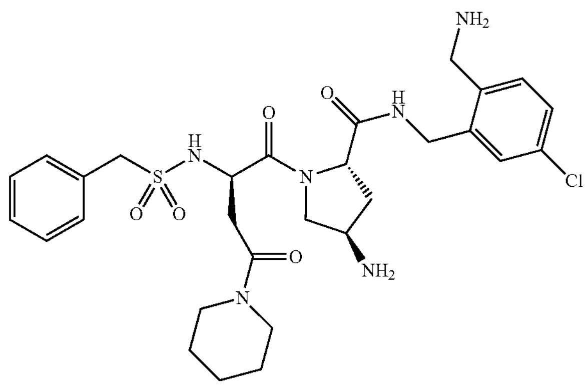 [SMILES: NCc1ccc(Cl)cc1CNC(=O)[C@@H]1C[C@@H](N)CN1C(=O)[C@@H](CC(=O)N1CCCCC1)NS(=O)(=O)Cc1ccccc1] | a) 1.36 | 618.2/619.0 (M + H)+ | 61.7 HPLC 2 |
| 2.8 | 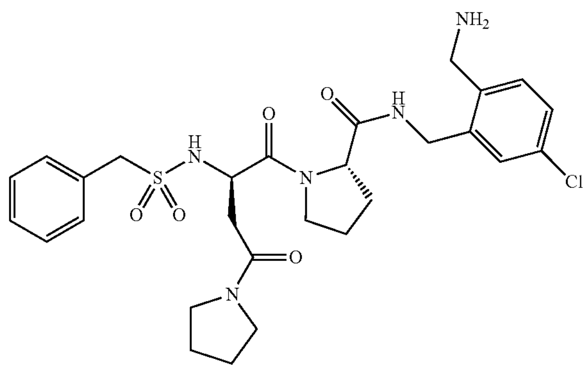 [SMILES: NCc1ccc(Cl)cc1CNC(=O)[C@@H]1CCCN1C(=O)[C@@H](CC(=O)N1CCCC1)NS(=O)(=O)Cc1ccccc1] | a) 1.51 | 589.2/590.0 (M + H)+ | 57.7 HPLC 1 |
| 2.9 | 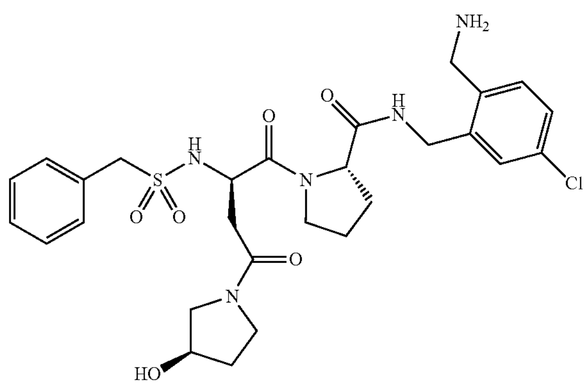 [SMILES: NCc1ccc(Cl)cc1CNC(=O)[C@@H]1CCCN1C(=O)[C@@H](CC(=O)N1CC[C@@H](O)C1)NS(=O)(=O)Cc1ccccc1] | a) 1.52 | 605.2/606.1 (M + H)+ | 55.1 HPLC 1 |
| 2.10 | 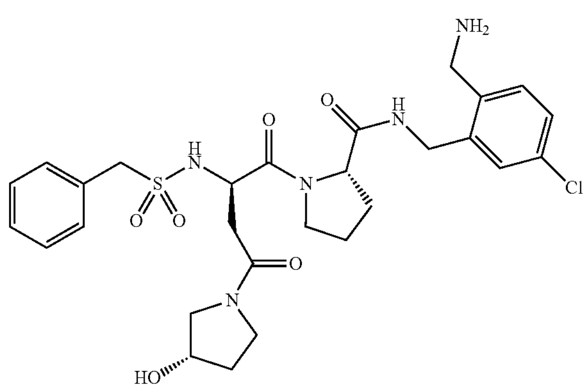 [SMILES: NCc1ccc(Cl)cc1CNC(=O)[C@@H]1CCCN1C(=O)[C@@H](CC(=O)N1CC[C@H](O)C1)NS(=O)(=O)Cc1ccccc1] | a) 1.53 | 605.2/606.1 (M + H)+ | 54.9 HPLC 1 |

TABLE 6-continued

| # | Structure | Precursors | MS calculated/ found | HPLC % B |
|---|---|---|---|---|
| 2.11 | 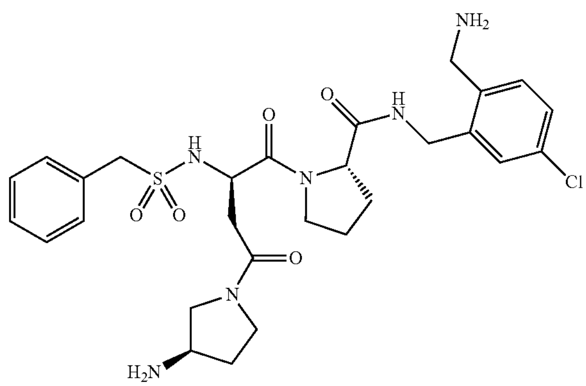 [SMILES: NCc1ccc(Cl)cc1CNC(=O)[C@@H]1CCCN1C(=O)[C@@H](CC(=O)N1CC[C@@H](N)C1)NS(=O)(=O)Cc1ccccc1] | a) 1.54 | 604.2/605.1 (M + H)+ | 48.6 HPLC 1 |
| 2.12 | 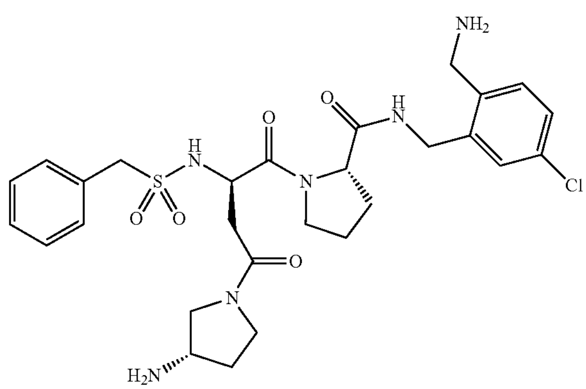 [SMILES: NCc1ccc(Cl)cc1CNC(=O)[C@@H]1CCCN1C(=O)[C@@H](CC(=O)N1CC[C@H](N)C1)NS(=O)(=O)Cc1ccccc1] | a) 1.55 | 604.2/605.1 (M + H)+ | 48.0 HPLC 1 |
| 2.13 | 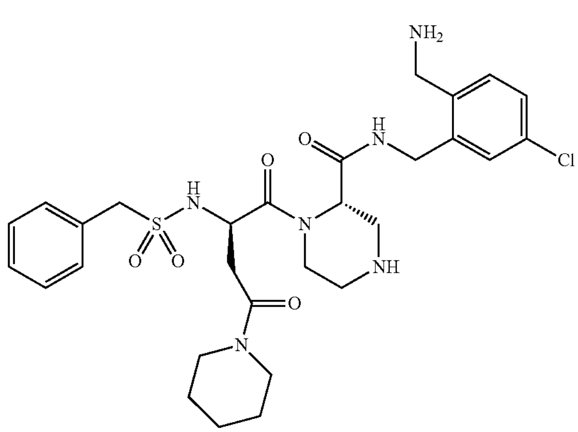 [SMILES: NCc1ccc(Cl)cc1CNC(=O)[C@@H]1CNCCN1C(=O)[C@@H](CC(=O)N1CCCCC1)NS(=O)(=O)Cc1ccccc1] | a) 1.39 | 618.2/619.0 (M + H)+ | 67.2 HPLC 2 |

TABLE 6-continued

| # | Structure | Precursors | MS calculated/ found | HPLC % B |
|---|---|---|---|---|
| 2.14 | 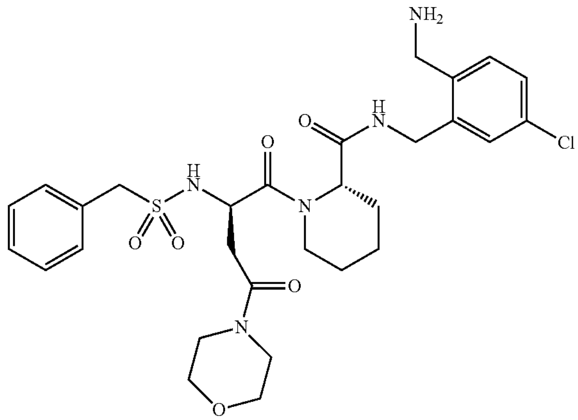 [SMILES: NCc1ccc(Cl)cc1CNC(=O)[C@@H]1CCCCN1C(=O)[C@@H](CC(=O)N1CCOCC1)NS(=O)(=O)Cc1ccccc1] | a) 1.34 | 619.2/620.2 (M + H)+ | 72.4 HPLC 2 |
| 2.15 | 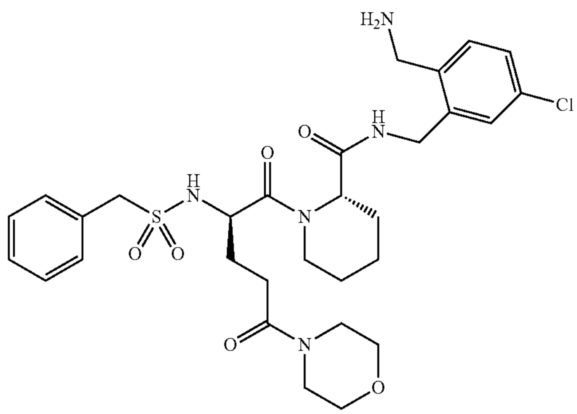 [SMILES: NCc1ccc(Cl)cc1CNC(=O)[C@@H]1CCCCN1C(=O)[C@@H](CCC(=O)N1CCOCC1)NS(=O)(=O)Cc1ccccc1] | a) 1.32 | 633.2/634.0 (M + H)+ | 70.7 HPLC 2 |
| 2.16 | 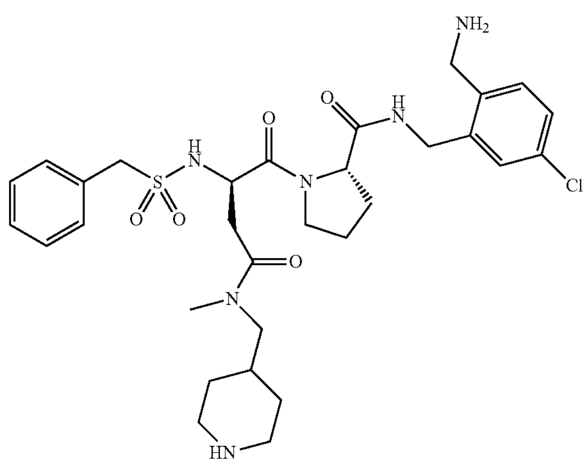 [SMILES: CN(CC1CCNCC1)C(=O)C[C@@H](NS(=O)(=O)Cc1ccccc1)C(=O)N1CCC[C@H]1C(=O)NCc1cc(Cl)ccc1CN] | a) 1.46 | 646.3/647.2 (M + H)+ | 60.0 HPLC 2 |

TABLE 6-continued

| # | Structure | Precursors | MS calculated/ found | HPLC % B |
|---|---|---|---|---|
| 2.17 | 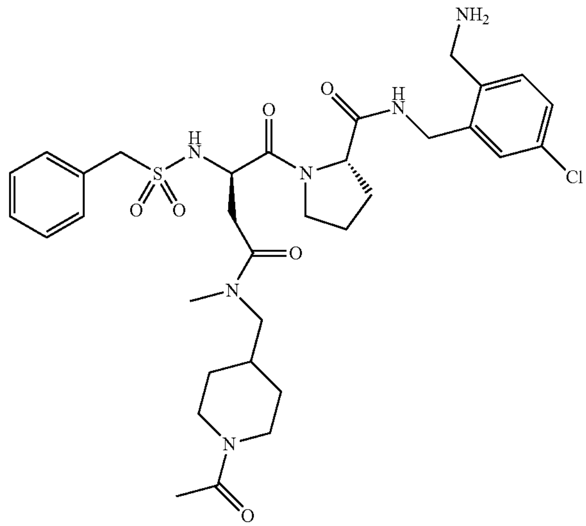 [SMILES: CC(=O)N1CCC(CN(C)C(=O)C[C@@H](NS(=O)(=O)Cc2ccccc2)C(=O)N2CCC[C@H]2C(=O)NCc2cc(Cl)ccc2CN)CC1] | a) 1.66 | 688.3/688.9 (M + H)+ | 77.4 HPLC 2 |
| 2.18 | 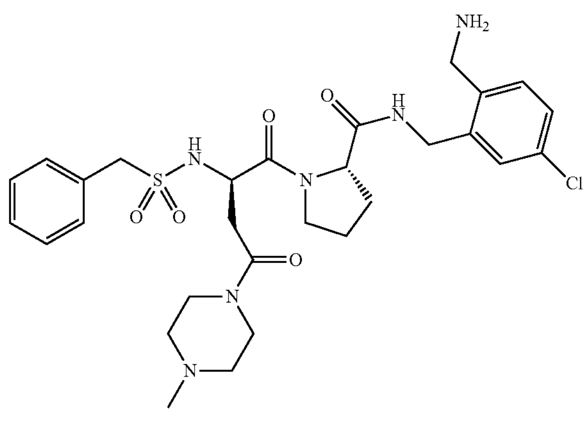 [SMILES: CN1CCN(C(=O)C[C@@H](NS(=O)(=O)Cc2ccccc2)C(=O)N2CCC[C@H]2C(=O)NCc2cc(Cl)ccc2CN)CC1] | a) 1.49 | 618.2/619.1 (M + H)+ | 50.1 HPLC 1 |
| 2.19 | 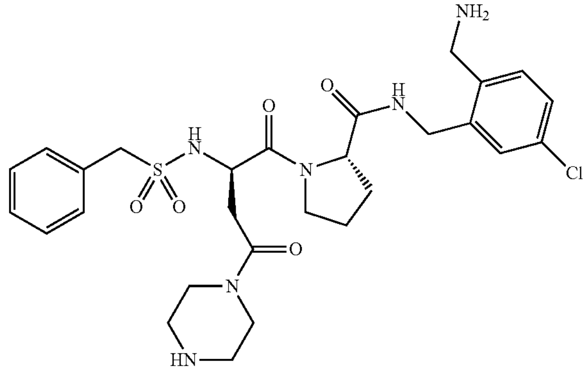 [SMILES: NCc1ccc(Cl)cc1CNC(=O)[C@@H]1CCCN1C(=O)[C@@H](CC(=O)N1CCNCC1)NS(=O)(=O)Cc1ccccc1] | a) 1.43 | 604.2/605.2 (M + H)+ | 49.6 HPLC 1 |

TABLE 6-continued
| # | Structure | Precursors | MS calculated/ found | HPLC % B |
|---|---|---|---|---|
| 2.20 | 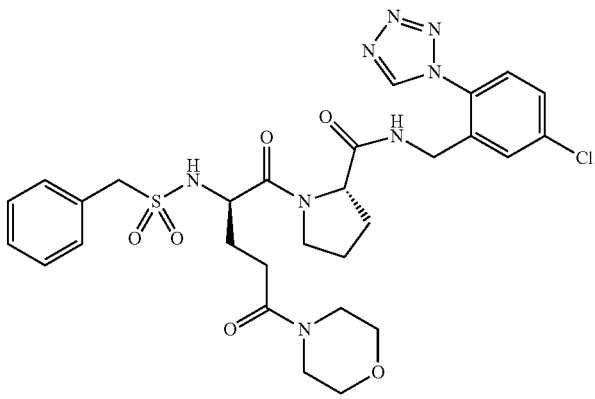 [SMILES: O=C(NCc1cc(Cl)ccc1-n1cnnn1)[C@@H]1CCCN1C(=O)[C@@H](CCC(=O)N1CCOCC1)NS(=O)(=O)Cc1ccccc1] | a) 1.28<br>b) CAS 449756-95-0 instead of CAS 439116-15-1 | 658.2/659.1 (M + H)+ | 61.2 HPLC 1 |
| 2.21 | 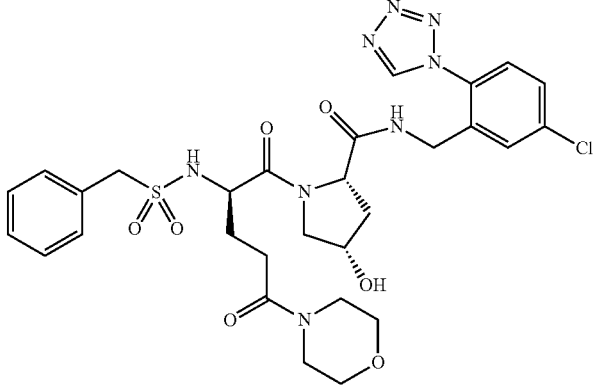 [SMILES: O=C(NCc1cc(Cl)ccc1-n1cnnn1)[C@@H]1C[C@H](O)CN1C(=O)[C@@H](CCC(=O)N1CCOCC1)NS(=O)(=O)Cc1ccccc1] | a) 1.29<br>b) CAS 449756-95-0 instead of CAS 439116-15-1 | 674.2/675.3 (M + H)+ | 58.2 HPLC 1 |
| 2.22 | 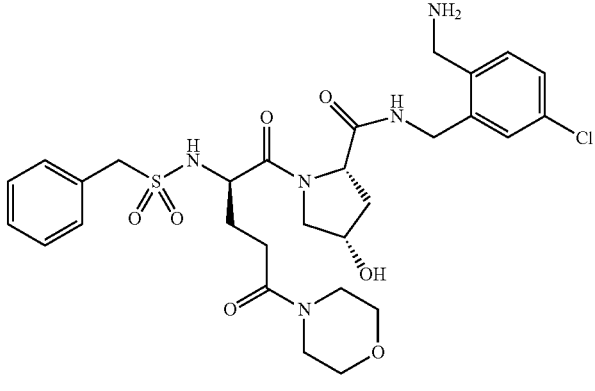 [SMILES: NCc1ccc(Cl)cc1CNC(=O)[C@@H]1C[C@H](O)CN1C(=O)[C@@H](CCC(=O)N1CCOCC1)NS(=O)(=O)Cc1ccccc1] | a) 1.29 | 635.2/636.2 (M + H)+ | 51.0 HPLC 1 |
| 2.23 | 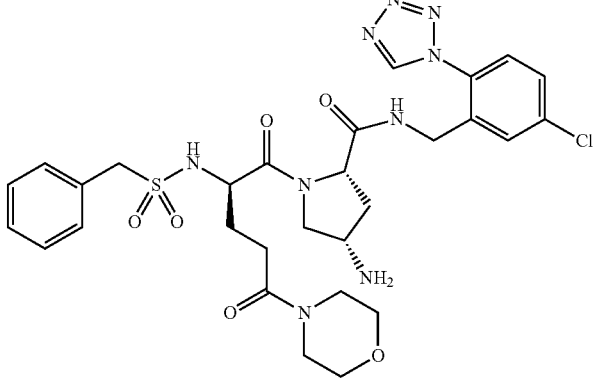 | a) 1.30<br>b) CAS 449756-95-0 instead of CAS 439116-15-1 | 673.2/674.2 (M + H)+ | 52.9 HPLC 1 |

TABLE 6-continued
| # | Structure | Precursors | MS calculated/ found | HPLC % B |
|---|---|---|---|---|
| 2.24 | 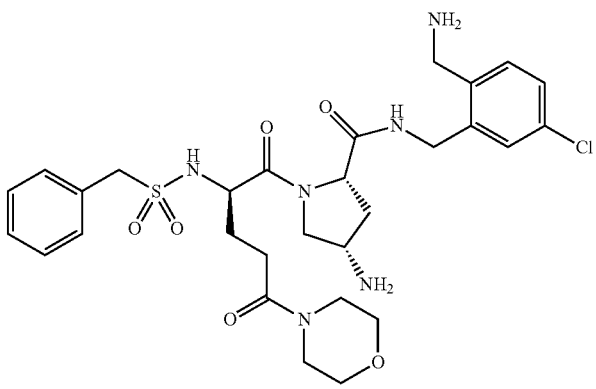 [SMILES: NCc1ccc(Cl)cc1CNC(=O)[C@@H]1C[C@H](N)CN1C(=O)[C@@H](CCC(=O)N1CCOCC1)NS(=O)(=O)Cc1ccccc1] | a) 1.30 | 634.2/635.2 (M + H)⁺ | 43.9 HPLC 1 |
| 2.25 | 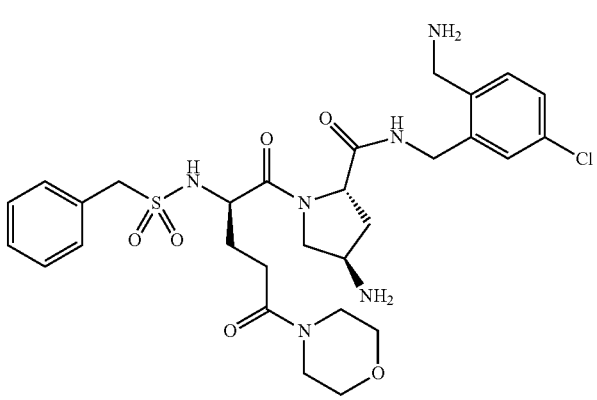 [SMILES: NCc1ccc(Cl)cc1CNC(=O)[C@@H]1C[C@@H](N)CN1C(=O)[C@@H](CCC(=O)N1CCOCC1)NS(=O)(=O)Cc1ccccc1] | a) 1.31 | 634.2/635.1 (M + H)⁺ | 45.7 HPLC 1 |
| 2.26 | 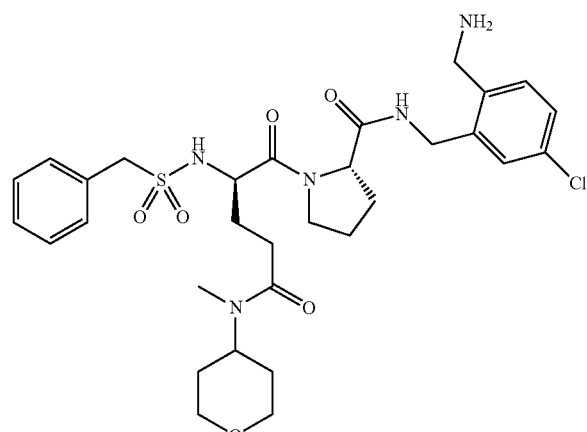 | a) 1.40 | 647.3/648.3 (M + H)⁺ | 56.4 HPLC 1 |

TABLE 6-continued
| # | Structure | Precursors | MS calculated/ found | HPLC % B |
|---|---|---|---|---|
| 2.27 | 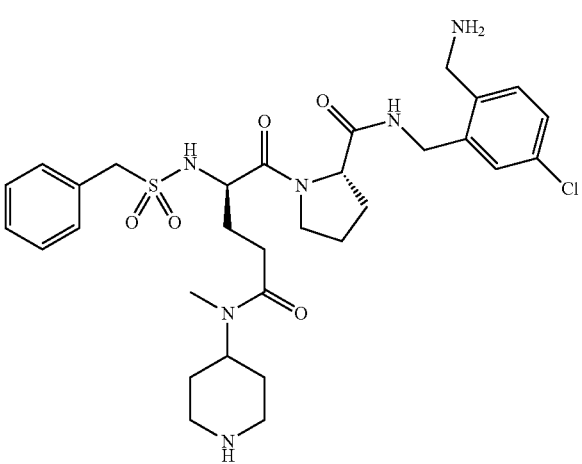 [SMILES: CN(C(=O)CC[C@@H](NS(=O)(=O)Cc1ccccc1)C(=O)N1CCC[C@H]1C(=O)NCc1cc(Cl)ccc1CN)C1CCNCC1] | a) 1.33 | 646.2/647.3 (M + H)+ | 47.2 HPLC 1 |
| 2.28 | 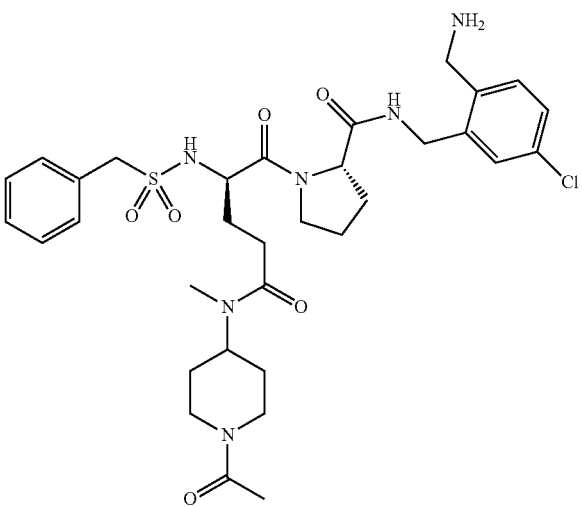 [SMILES: CC(=O)N1CCC(N(C)C(=O)CC[C@@H](NS(=O)(=O)Cc2ccccc2)C(=O)N2CCC[C@H]2C(=O)NCc2cc(Cl)ccc2CN)CC1] | a) 1.67 | 688.3/689.2 (M + H)+ | 55.0 HPLC 1 |
| 2.29 | 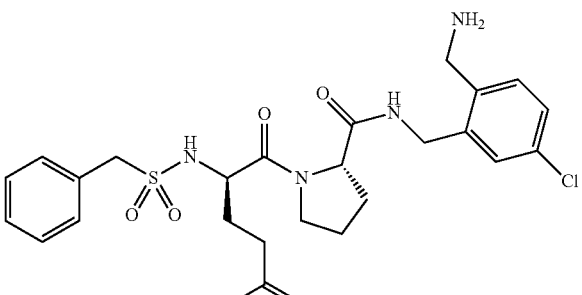 | a) 1.56 | 550.2/551.1 (M + H)+ | 44.1 HPLC 1 |

TABLE 6-continued

| # | Structure | Precursors | MS calculated/ found | HPLC % B |
|---|---|---|---|---|
| 2.30 | 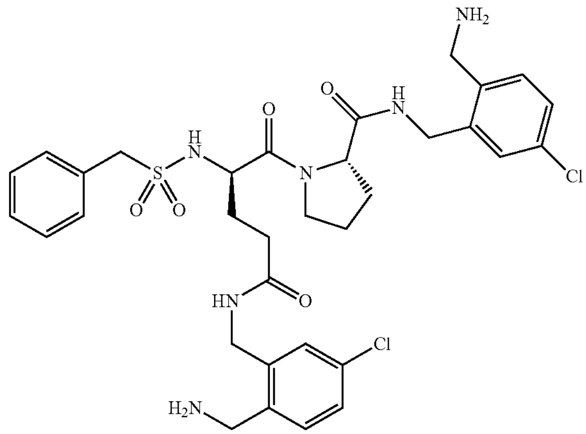 [SMILES: NCc1ccc(Cl)cc1CNC(=O)CC[C@@H](NS(=O)(=O)Cc1ccccc1)C(=O)N1CCC[C@H]1C(=O)NCc1cc(Cl)ccc1CN] | a) 1.57<br>b) 2eq CAS 439116-15-1 | 702.2/703.2 (M + H)+ | 57.2 HPLC 1 |
| 2.31 | 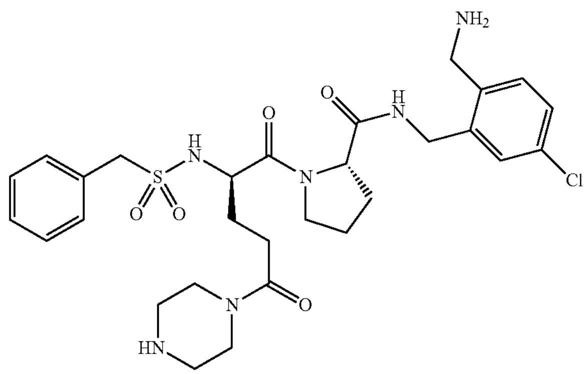 [SMILES: NCc1ccc(Cl)cc1CNC(=O)[C@@H]1CCCN1C(=O)[C@@H](CCC(=O)N1CCNCC1)NS(=O)(=O)Cc1ccccc1] | a) 1.60 | 618.2/619.0 (M + H)+ | 46.3 HPLC 1 |
| 2.32 | 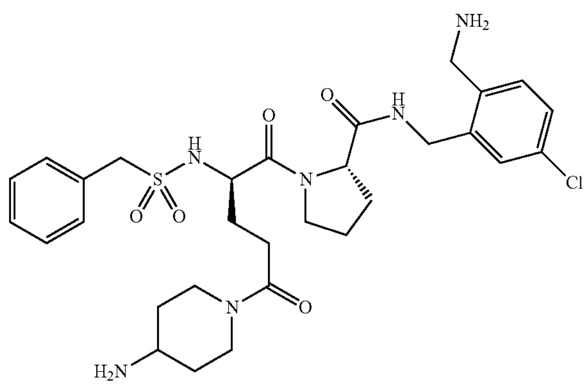 [SMILES: NCc1ccc(Cl)cc1CNC(=O)[C@@H]1CCCN1C(=O)[C@@H](CCC(=O)N1CCC(N)CC1)NS(=O)(=O)Cc1ccccc1] | a) 1.61 | 632.3/633.1 (M + H)+ | 46.9 HPLC 1 |
| 2.33 | 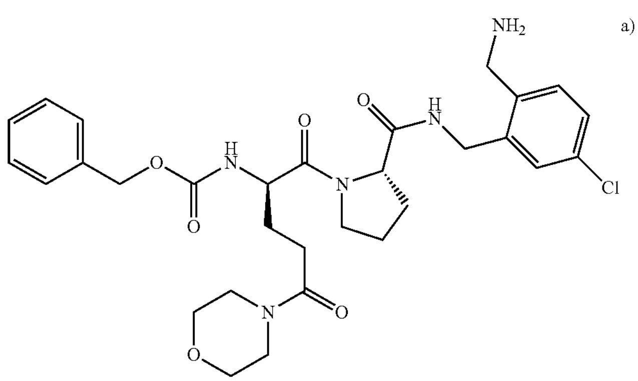 | a) 1.63 | 599.3/600.2 (M + H)+ | 59.4 HPLC 1 |

TABLE 6-continued

| # | Structure | Precursors | MS calculated/ found | HPLC % B |
|---|---|---|---|---|
| 2.34 | 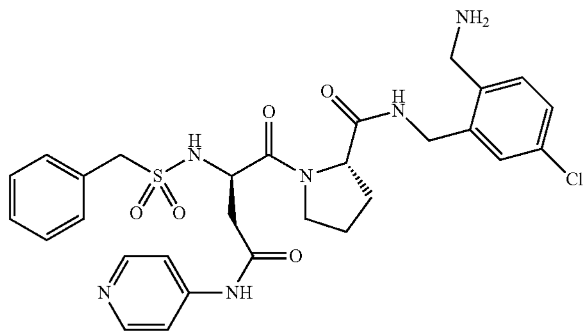 [SMILES: NCc1ccc(Cl)cc1CNC(=O)[C@@H]1CCCN1C(=O)[C@@H](CC(=O)Nc1ccncc1)NS(=O)(=O)Cc1ccccc1] | a) 1.27 | 612.2/614.2 (M + H)+ | 91.4 HPLC 2 |
| 2.35 | 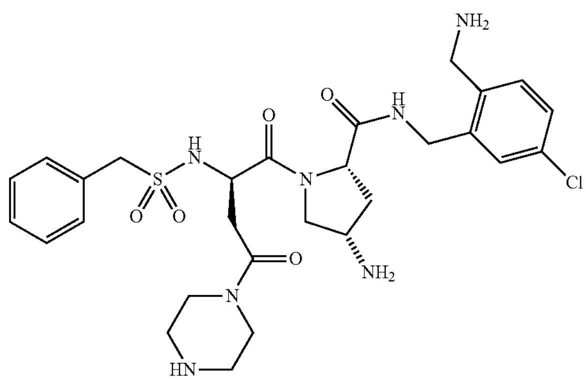 [SMILES: NCc1ccc(Cl)cc1CNC(=O)[C@@H]1C[C@H](N)CN1C(=O)[C@@H](CC(=O)N1CCNCC1)NS(=O)(=O)Cc1ccccc1] | a) 1.37 | 619.2/620.2 (M + H)+ | 75.0 HPLC 1 |
| 2.36 | 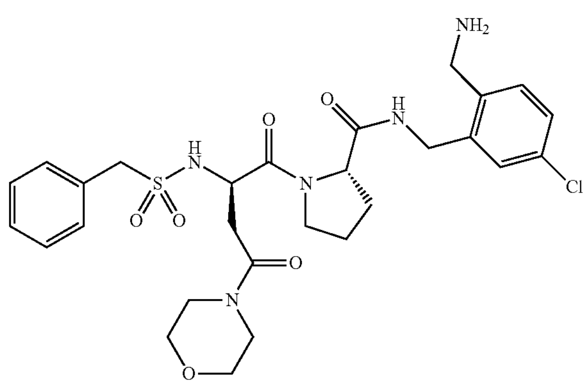 [SMILES: NCc1ccc(Cl)cc1CNC(=O)[C@@H]1CCCN1C(=O)[C@@H](CC(=O)N1CCOCC1)NS(=O)(=O)Cc1ccccc1] | a) 1.42 | 605.2/606.2 (M + H)+ | 68.9 HPLC 1 |
| 2.37 | 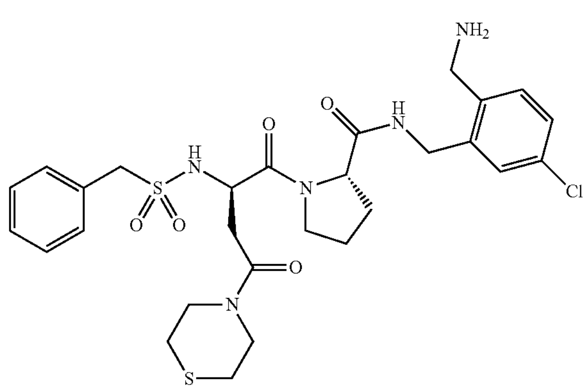 [SMILES: NCc1ccc(Cl)cc1CNC(=O)[C@@H]1CCCN1C(=O)[C@@H](CC(=O)N1CCSCC1)NS(=O)(=O)Cc1ccccc1] | a) 1.68 | 621.2/622.1 (M + H)+ | 60.9 HPLC 1 |

TABLE 6-continued

| # | Structure | Precursors | MS calculated/ found | HPLC % B |
|---|---|---|---|---|
| 2.38 | 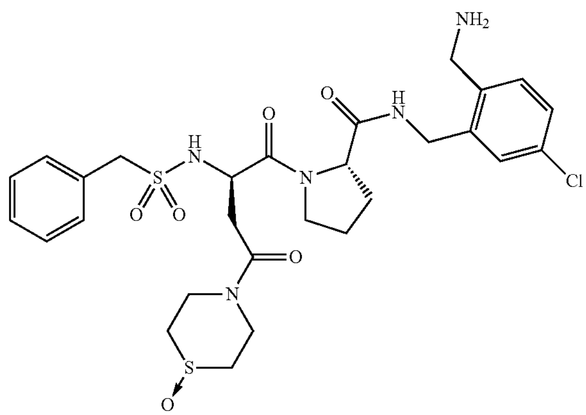 [SMILES: NCc1ccc(Cl)cc1CNC(=O)[C@@H]1CCCN1C(=O)[C@@H](CC(=O)N1CCS(=O)CC1)NS(=O)(=O)Cc1ccccc1] | a) 1.69 | 637.2/638.1 (M + H)⁺ | 57.9 HPLC 1 |
| 2.39 | 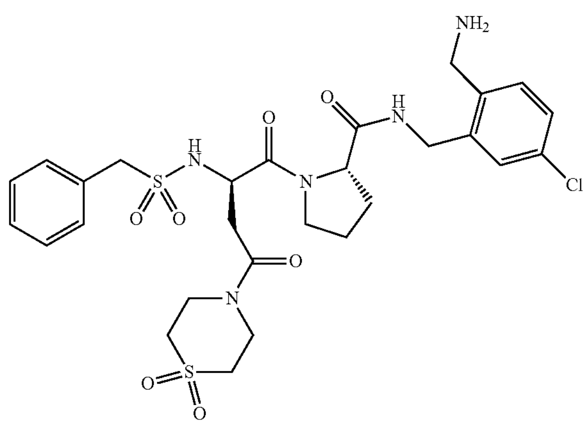 [SMILES: NCc1ccc(Cl)cc1CNC(=O)[C@@H]1CCCN1C(=O)[C@@H](CC(=O)N1CCS(=O)(=O)CC1)NS(=O)(=O)Cc1ccccc1] | a) 1.70 | 653.2/654.1 (M + H)⁺ | 55.4 HPLC 1 |
| 2.40 | 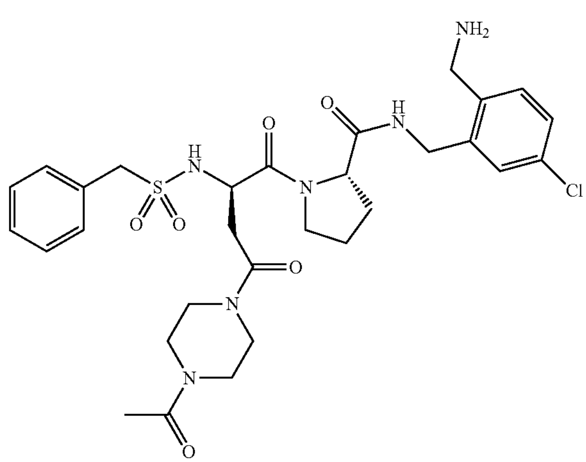 [SMILES: CC(=O)N1CCN(C(=O)C[C@@H](NS(=O)(=O)Cc2ccccc2)C(=O)N2CCC[C@H]2C(=O)NCc2cc(Cl)ccc2CN)CC1] | a) 1.62 | 646.2/647.2 (M + H)⁺ | 54.1 HPLC 1 |

| # | Structure | Precursors | MS calculated/ found | HPLC % B |
|---|---|---|---|---|
| 2.41 | 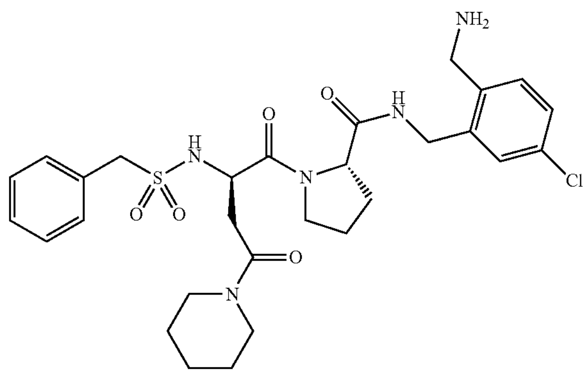 [SMILES: NCc1ccc(Cl)cc1CNC(=O)[C@@H]1CCCN1C(=O)[C@@H](CC(=O)N1CCCCC1)NS(=O)(=O)Cc1ccccc1] | a) 1.48 | 603.2/604.2 (M + H)+ | 59.4 HPLC 1 |
| 2.42 | 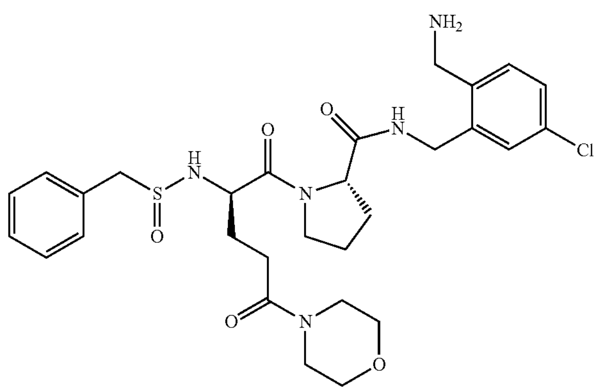 [SMILES: NCc1ccc(Cl)cc1CNC(=O)[C@@H]1CCCN1C(=O)[C@@H](CCC(=O)N1CCOCC1)NS(=O)Cc1ccccc1] | a) 1.41 | 583.3/584.3 (M + H)+ | 54.9 HPLC 1 |
| 2.43 | 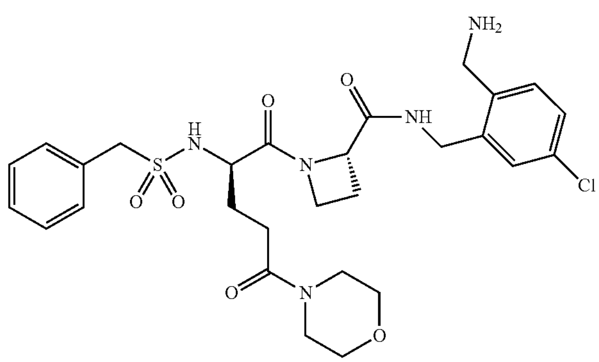 [SMILES: NCc1ccc(Cl)cc1CNC(=O)[C@@H]1CCN1C(=O)[C@@H](CCC(=O)N1CCOCC1)NS(=O)(=O)Cc1ccccc1] | a) 1.4 b) CAS: 439118-00-0 instead of CAS 439116-15-1 | 605.2/606.1 (M + H)+ | 62.6 HPLC 2 |
| 2.44 | 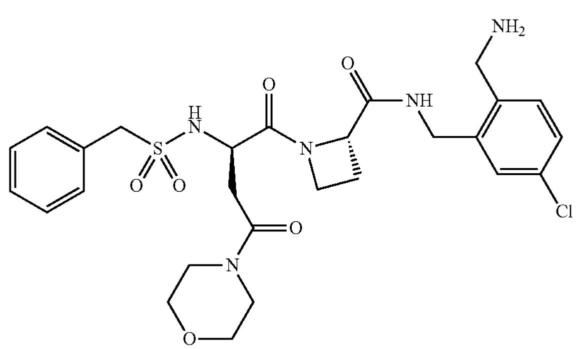 [SMILES: NCc1ccc(Cl)cc1CNC(=O)[C@@H]1CCN1C(=O)[C@@H](CC(=O)N1CCOCC1)NS(=O)(=O)Cc1ccccc1] | a) 1.14 b) CAS: 439118-00-0 instead of CAS 439116-15-1 | 591.2/592.0 (M + H)+ | 63.7 HPLC 2 |

TABLE 6-continued

| # | Structure | Precursors | MS calculated/found | HPLC % B |
|---|---|---|---|---|
| 2.45 | 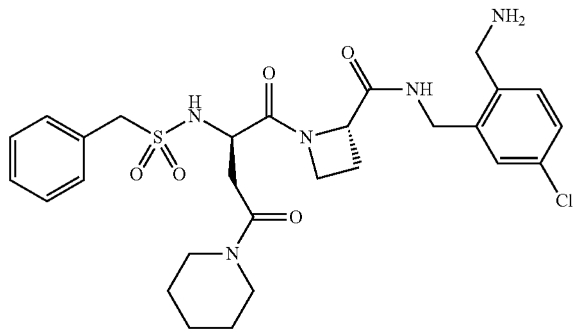 [SMILES: NCc1ccc(Cl)cc1CNC(=O)[C@@H]1CCN1C(=O)[C@@H](CC(=O)N1CCCCC1)NS(=O)(=O)Cc1ccccc1] | a) 1.16<br>b) CAS: 439118-00-0 instead of CAS 439116-15-1 | 589.2/590.2 (M + H)+ | 72.4 HPLC 2 |
| 2.46 | 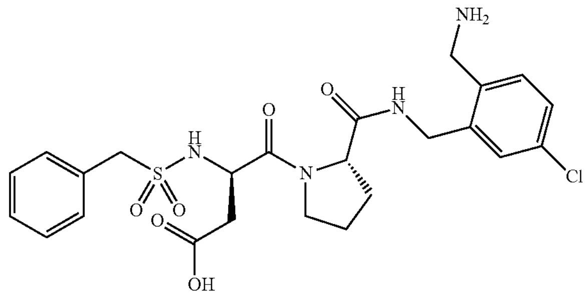 [SMILES: NCc1ccc(Cl)cc1CNC(=O)[C@@H]1CCCN1C(=O)[C@@H](CC(=O)O)NS(=O)(=O)Cc1ccccc1] | a) 1.22<br>b) CAS 439117-44-9 instead of CAS 439116-15-1 | 536.2/537.1 (M + H)+ | 67.7 HPLC 2 |

2.47 Bzls-D-Asp((tetrahydro-2H-pyran-4-yl)-N-methyl-methanamine)-L-Pro-Amb(2-AMe-5-Cl)×2 TFA 2.48 Bzls-D-Asp(1-oxido-4-amino-pyridine)-L-Pro-Amb(2-AMe-5-Cl)

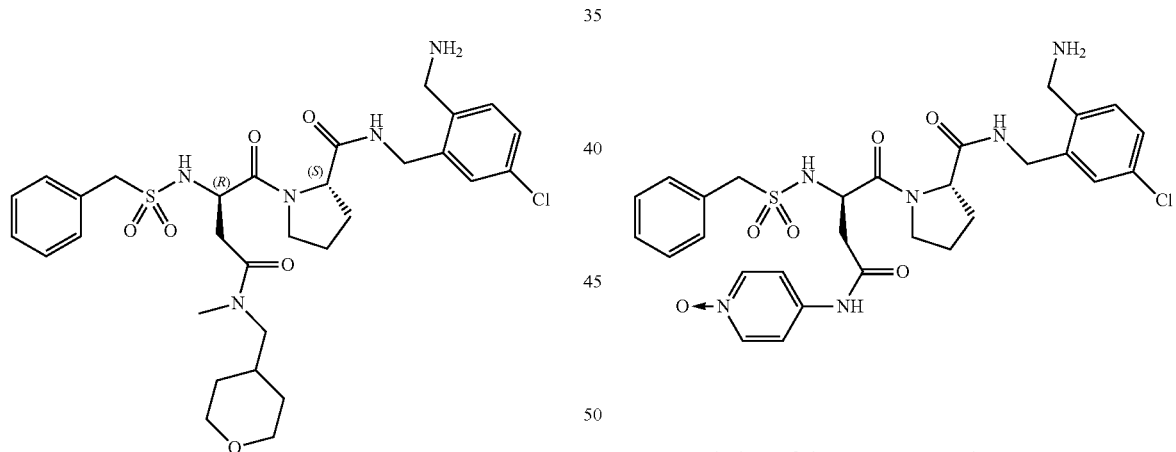

Compound 1.47 (256 mg, 0.52 mmol) and (2-Aminomethyl-4-chlorobenzyl)-carbamic acid tert-butyl ester (CAS 439116-15-1) were coupled according to the procedure described for compound 1.1. The resulting intermediate (0.49 mmol) was dissolved in 6 mL of 4 M HCl in dioxane and stirred at room temperature for 17 h. The mixture was then concentrated in vacuo and purified by preparative reversed phase HPLC to afford the title compound.

Yield: 223 mg (57%, white solid)
HPLC: 78.0% B HPLC 2; MS calc.: 647.2, found 648.1 (M+H)+

To a solution of the Boc protected precursor to 2.342.34 (121 mg, 0.17 mmol) in DCM (10 mL) was added 75% mCPBA (44 mg, 0.19 mmol) at room temperature and the mixture was stirred for 4 h. Additional 75% mCPBA (165 mg, 0.72 mmol) was added in 3 portions every 4 h. The mixture was dissolved in 50 mL DCM and 50 mL water. The organic layer was separated and washed with 2×50 mL $NaHSO_3$, 3×50 mL sat. $NaHCO_3$ and 2× brine, dried over $Na_2SO_4$ and evaporated in vacuo. The resulting intermediate was deprotected according to the procedure described for compound 1.2 and purified by preparative reversed phase HPLC to afford the title compound.

Yield: 2 mg (2%, white solid)
HPLC: 67.9% B HPLC 2; MS calc.: 628.2, found 629.2 (M+H)+

2.49 H-D-Glu(morpholino)-L-Pro-Amb(2-AMe-5-Cl)×2 TFA

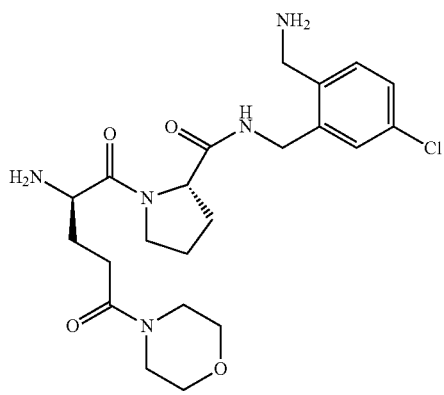 [SMILES: NCc1ccc(Cl)cc1CNC(=O)[C@@H]1CCCN1C(=O)[C@H](N)CCC(=O)N1CCOCC1]

2 mL HBr/HOAc (32%) were added to compound 2.33 (81 mg, 0.1 mmol). The mixture was stirred at room temperature for 4 h. The solvent was evaporated in vacuo and the remaining solid was dissolved in 2 mL MeOH. 50 mL Ether was added and the precipitate was collected. The crude product was purified by preparative reversed phase HPLC to afford the title compound.

Yield: 33 mg (42%, white solid)

HPLC: 35.3% B HPLC 1; MS calc.: 465.2, found 466.1 (M+H)$^+$ 2.50 Bzls-D-Asp(piperazinyl)-L-Aze-Amb(2-AMe-5-Cl)×2 TFA

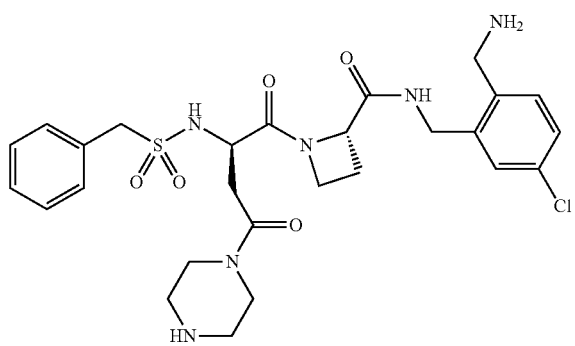 [SMILES: NCc1ccc(Cl)cc1CNC(=O)[C@@H]1CCN1C(=O)[C@@H](CC(=O)N1CCNCC1)NS(=O)(=O)Cc1ccccc1]

Compound 1.15 (126 mg, 0.22 mmol) and [[2-[[[(2S)-2-Azetidinyl-carbonyl]amino]methyl]-4-chlorophenyl]methyl]-carbamic acid-1,1-dimethylethyl ester (CAS: 439118-00-0) were coupled according to the procedure described for compound 1.1. To a solution of the resulting intermediate in dry DMF (2 mL) was added piperidine (0.2 mL) and the mixture was stirred at room temperature for 3.5 h. The solvent was evaporated in vacuo and the residue was dissolved in 2.0 mL DCM. TFA (2.0 mL) was added and the mixture was stirred at room temperature for 1 h. The solvent was evaporated in vacuo and the crude product was purified by preparative reversed phase HPLC to afford the title compound.

Yield: 34 mg (19%, white solid)

HPLC: 56.5% B HPLC 2; MS calc.: 590.2, found 589.0 (M−H)$^−$

Example 2

Determination of the Inhibition Constants for Human Factor IIa (h FIIa) and Human Factor Xa (h FXa)

The inhibitory effect against the individual purified enzymes was determined in analogy to a previously disclosed method (Stürzebecher et al., *J. Med. Chem.*, 40, 3091-3099 (1997)). The reactions to determine the inhibition of human factor IIa and human factor Xa were carried out in the following mixture at 25° C.:

200 μL of TBS (0.05 M trishydroxymethylaminomethane; 0.154 M NaCl, 2% ethanol, pH 8.0)

25 μL of substrate (2 mM, 1 mM and 0.5 mM Mes-d-Cha-Gly-Arg-pNA (Pefachrome tPA from DSM nutritional products, Pentapharm division) for factor IIa and MeOCO-d-Cha-Gly-Arg-pNA (Pefachrome FXa from DSM nutritional products, Pentapharm division) for factor Xa, dissolved in H$_2$O)

2 μL of a solution of the test compound in water

50 μL of a solution of the enzyme (human alpha-thrombin from Enzyme Research Laboratories at 0.05 to 0.1 NIH U/mL in 0.154 M NaCl+0.1% BSA m/v; human Factor Xa from Enzyme Research Laboratories at 2.5 to 5 mIU/mL in 0.154 M NaCl+0.1% BSA m/v)

The release of p-nitroaniline (p-NA, the chromogenic product of the proteolytic activity), was determined by change in absorbance at 405 nm. The equilibrium rates were used to calculate the inhibitor/enzyme dissociation constant (K$_i$ values) by parameter fitting in accordance with the rate equation for competitive inhibition using GraFit (version 4 from Erithacus). The results are reported as K$_i$ values (nanomolar) in table 7 and are the average of at least three determinations.

These data clearly show that the compounds of the invention are very potert inhibitors of both thrombin and factor Xa. Dissociation constants are in the nanomolar range, and in general less than 50 nM.

Example 3

Determination of Inhibition Constants for Reference Enzymes

Human Activated Protein C (h aPC): Inhibition of human aPC was determined by the method described in example 2 using human activated protein C from Enzyme Research Laboratories at 2.2 nM and H-D-Lys(Cbo)-Pro-Arg-pNA (Pefachrome PCa from DSM nutritional products, Pentapharm division) at 2 mM, 1 mM, and 0.5 mM as substrate; results are reported as Ki values (nanomolar) in table 7.

Human urinary kallikrein (h uKK): Inhibition of human uKK was determined by the method described in example 2 using human urinary kallikrein from Lee Biosolutions at 7.5 nM and H-D-Val-Leu-Arg-pNA (S-2266 from Chromogenix) at 1 mM, 0.5 mM, and 0.25 mM as substrate; results are reported as Ki values (nanomolar) in table 7.

Subcomponent "s" of Human Complement Component 1 (h C1s): Inhibition of human C1s was determined by the method described in [example 2 using native human activated C1s complement component from Calbiochem at 29 nM and H-D-Val-Ser-Arg-pNA (S-2314 from Chromogenix) at 8 mM, 6 mM, and 4 mM as substrate; results are reported as Ki values (nanomolar) in table 7.

Subcomponent "r" of Human Complement Component 1 (h C1r): Inhibition of human C1r was determined by the method described in example 2 using native human activated C1r complement component from Calbiochem at 100 nM and Val-Ser-Arg-pNA (S-2314 from Chromogenix) at 16 mM, 12 mM, and 8 mM as substrate; results are reported as Ki values (nanomolar) in table 7.

Human urokinase type plasminogen activator (h u-PA): Inhibition of human uPA was determined by the method described in example 2 using u-pa "Urokinase HS medac" from MEDAC GmbH at 100 units/ml and H-Glu-Gly-Arg-pNA (L-1455 from Bachem) as substrate at 2 mM; 1 mM, 0.5 mM as substrate; results are reported as Ki values (nanomolar) in table 7.

Human tissue-type plasminogen activator (h t-PA): Inhibition of human t-PA was determined by the method described in example 2 using recombinant human tissue-type plasminogen activator (Actilyse®) from Boehringer Ingelheim at 200 U/mL and Mes-d-Cha-Gly-Arg-pNA (Pefachrome tPA from DSM nutritional products, Pentapharm division) at 4 mM, 2 mM, and 1 mM as substrate; results are reported as Ki values (nanomolar) in table 7.

Human plasmin (h plasmin): Inhibition of human plasmin was determined by the method described in example 2 using activated human plasmin from Calbiochem at 1.7 mU/mL and tosyl-Gly-Pro-Lys-pNA (Chromozym PL from Roche Applied Science) at 4 mM, 2 mM, and 1 mM as substrate; results are reported as Ki values (nanomolar) in table 7.

Human plasma kallikrein (h PK): Inhibition of human PK was determined by the method described in example 2 using activated human plasma kallikrein from Enzyme Research Laboratories at 62 ng/mL and H-D-Pro-Phe-Arg-pNA (S2302 from Chromogenix) at 3 mM, 1.5 mM, and 1 mM as substrate; results are reported as Ki values (nanomolar) in table 7.

Dissociation constants were calculated as described herein. Results for exemplary compounds of the invention are shown in Table 7.

These data presented in table 7 show that the dissociation constants of the compounds of the invention towards thrombin and factor Xa are at least one order of magnitude lower than those towards other reference proteases involved in the coagulation cascade. In fact, the inhibitory activity towards thrombin and factor Xa is generally 100 fold greater than towards any other comparator protease, and in some cases, such as compounds 2.1, 2.6, 2.8, 2.13, 2.24, 2.36, 2.41 and 2.45, there is at least 1000 fold greater inhibitory activity towards thrombin and factor Xa than towards any of the other comparator proteases.

TABLE 7

Dissociation constants ($K_i$) of the exemplary compounds towards thrombin, factor Xa and key reference proteases.

| Compound | Structure | Enzyme assayed | $K_i$ (nm) |
|---|---|---|---|
| 2.1 | 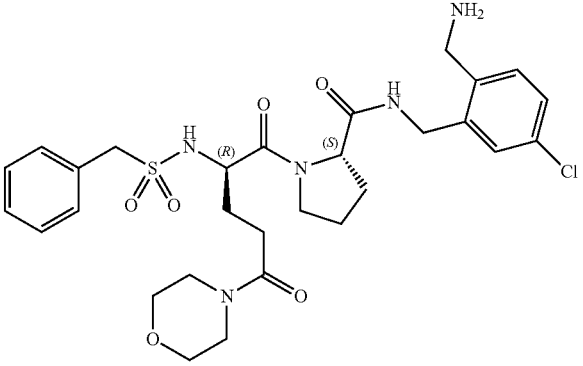 | h FIIa<br>h FXa<br>h aPC<br>h plasmin<br>h PK<br>h t-PA<br>h u-PA<br>h C1s<br>h C1r<br>h uKK | 0.43<br>1.1<br>>100,000<br>>28,000<br>1,860<br>>20,000<br>>40,000<br>>80,000<br>>200,000<br>>60,000 |
| 2.2 | 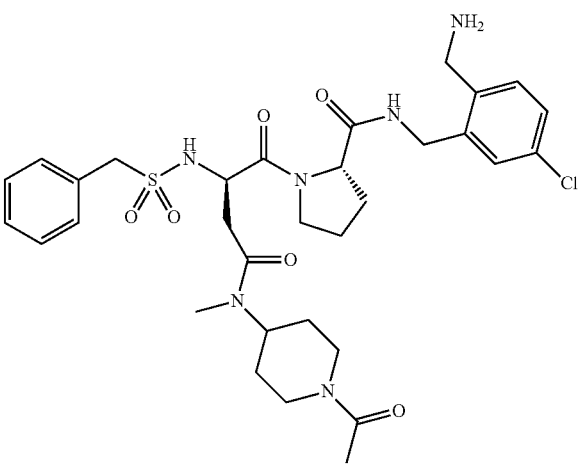 [SMILES: CC(=O)N1CCC(N(C)C(=O)C[C@@H](NS(=O)(=O)Cc2ccccc2)C(=O)N2CCC[C@H]2C(=O)NCc2cc(Cl)ccc2CN)CC1] | h FIIa<br>h FXa<br>h aPC<br>h plasmin<br>h PK<br>h t-PA<br>h u-PA<br>h C1s<br>h C1r<br>h uKK | 3.1<br>23<br>>90,000<br>>10,000<br>4,460<br>>100,000<br>>50,000<br>>100,000<br>>50,000<br>>10,000 |

TABLE 7-continued

Dissociation constants ($K_i$) of the exemplary compounds towards thrombin, factor Xa and key reference proteases.

| Compound | Structure | Enzyme assayed | $K_i$ (nm) |
|---|---|---|---|
| 2.3 | 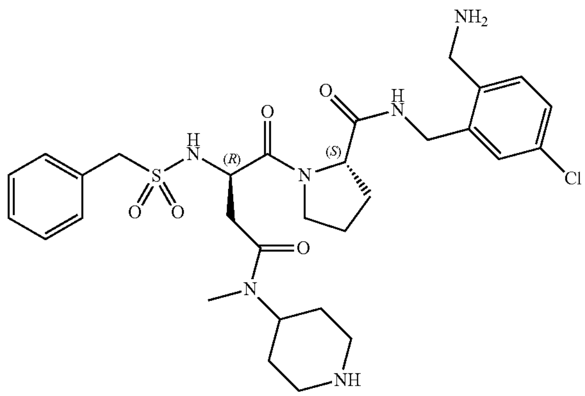 | h FIIa | 3 |
| | | h FXa | 23 |
| | | h aPC | >10,000 |
| | | h plasmin | >100,000 |
| | | h PK | 5,314 |
| | | h t-PA | >50,000 |
| | | h u-PA | >100,000 |
| | | h Cls | >20,000 |
| | | h Clr | >100,000 |
| | | h uKK | >50,000 |
| 2.4 | 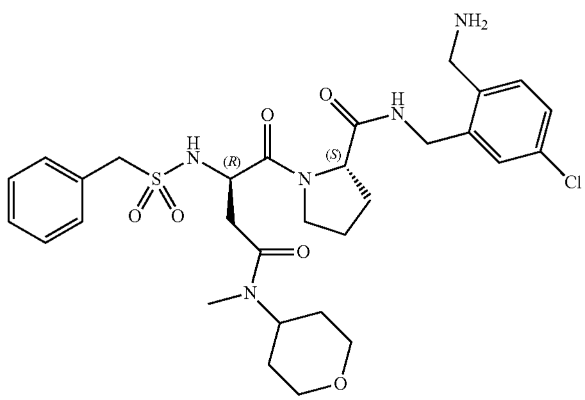 | h FIIa | 0.56 |
| | | h FXa | 1.3 |
| | | h aPC | >10,000 |
| | | h plasmin | >20,000 |
| | | h PK | 262 |
| | | h t-PA | >100,000 |
| | | h u-PA | >40,000 |
| | | h Cls | >25,000 |
| | | h Clr | >10,000 |
| | | h uKK | >50,000 |
| 2.5 | 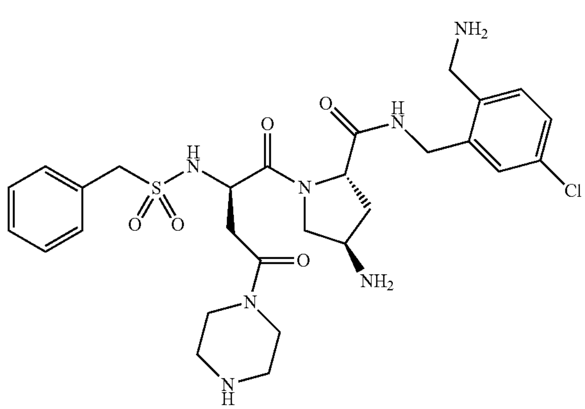 [SMILES: NCc1ccc(Cl)cc1CNC(=O)[C@@H]1C[C@@H](N)CN1C(=O)[C@@H](CC(=O)N1CCNCC1)NS(=O)(=O)Cc1ccccc1] | h FIIa | 18 |
| | | h FXa | 2.8 |
| | | h aPC | >20,000 |
| | | h plasmin | >10,000 |
| | | h PK | 639 |
| | | h t-PA | 9,270 |
| | | h u-PA | >100,000 |
| | | h Cls | >20,000 |
| | | h Clr | >100,000 |
| | | h uKK | >100,000 |

TABLE 7-continued

Dissociation constants (K$_i$) of the exemplary compounds towards thrombin, factor Xa and key reference proteases.

| Compound | Structure | Enzyme assayed | K$_i$ (nm) |
|---|---|---|---|
| 2.6 | 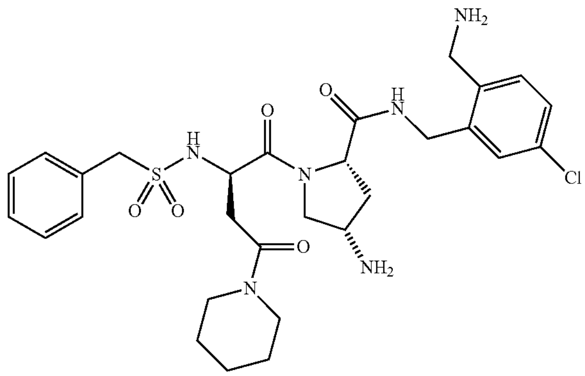 [SMILES: NCc1ccc(Cl)cc1CNC(=O)[C@@H]1C[C@H](N)CN1C(=O)[C@@H](CC(=O)N1CCCCC1)NS(=O)(=O)Cc1ccccc1] | h FIIa<br>h FXa<br>h aPC<br>h plasmin<br>h PK<br>h t-PA<br>h u-PA<br>h Cls<br>h Clr<br>h uKK | 0.18<br>0.049<br>>100,000<br>8,745<br>335<br>5,050<br>>30,000<br>>20,000<br>>20,000<br>>50,000 |
| 2.7 | 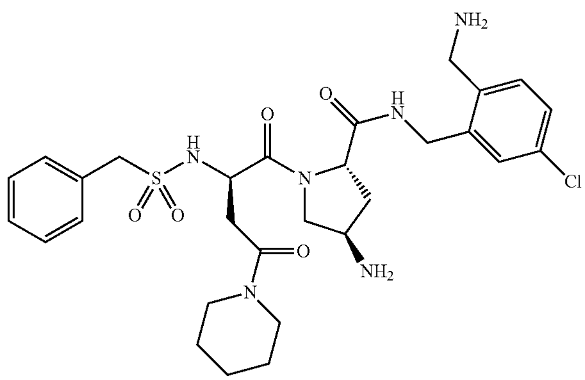 [SMILES: NCc1ccc(Cl)cc1CNC(=O)[C@@H]1C[C@@H](N)CN1C(=O)[C@@H](CC(=O)N1CCCCC1)NS(=O)(=O)Cc1ccccc1] | h FIIa<br>h FXa<br>h aPC<br>h plasmin<br>h PK<br>h t-PA<br>h u-PA<br>h Cls<br>h Clr<br>h uKK | 0.57<br>0.18<br>>50,000<br>11,860<br>322<br>15,275<br>>50,000<br>>30,000<br>>20,000<br>>50,000 |
| 2.8 | 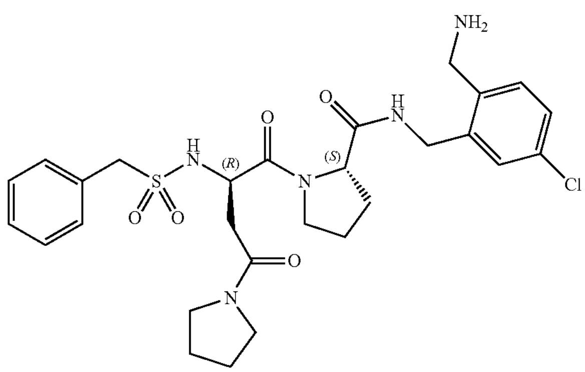 | h FIIa<br>h FXa<br>h aPC<br>h plasmin<br>h PK<br>h t-PA<br>h u-PA<br>h Cls<br>h Clr<br>h uKK | 0.21<br>0.13<br>>40,000<br>>20,000<br>337<br>>10,000<br>>80,000<br>>50,000<br>>100,000<br>>100,000 |
| 2.9 | 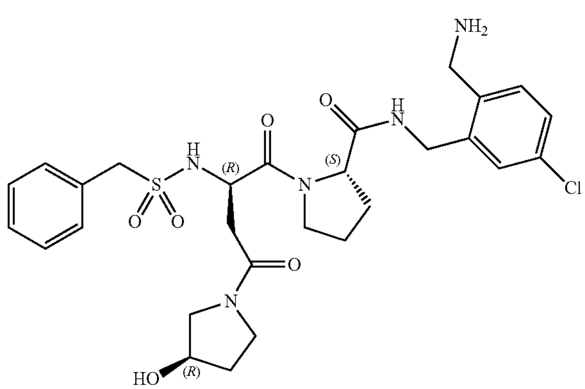 | h FIIa<br>h FXa<br>h aPC<br>h plasmin<br>h PK<br>h t-PA<br>h u-PA<br>h Cls<br>h Clr<br>h uKK | 1.2<br>2.5<br>>25,000<br>>10,000<br>930<br>>20,000<br>>100,000<br>>50,000<br>>50,000<br>>200,000 |

TABLE 7-continued

Dissociation constants (K$_i$) of the exemplary compounds towards thrombin, factor Xa and key reference proteases.

| Compound | Structure | Enzyme assayed | K$_i$ (nm) |
|---|---|---|---|
| 2.10 | 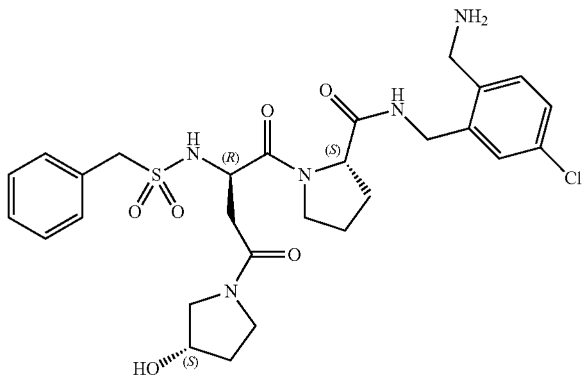 | h FIIa | 0.9 |
| | | h FXa | 1.1 |
| | | h aPC | >20,000 |
| | | h plasmin | >10,000 |
| | | h PK | 830 |
| | | h t-PA | >10,000 |
| | | h u-PA | >100,000 |
| | | h CIs | >20,000 |
| | | h CIr | >20,000 |
| | | h uKK | >100,000 |
| 2.11 | 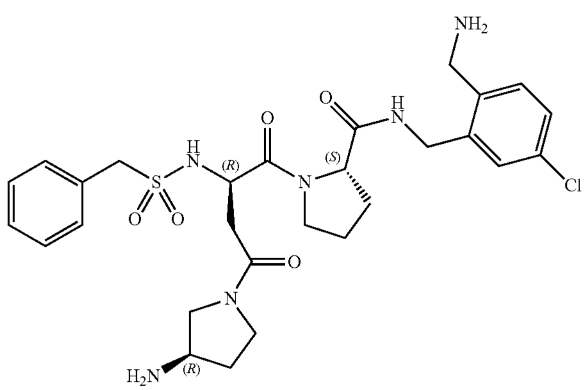 | h FIIa | 5.9 |
| | | h FXa | 14 |
| | | h aPC | >50,000 |
| | | h plasmin | >100,000 |
| | | h PK | 3,352 |
| | | h t-PA | >100,000 |
| | | h u-PA | >20,000 |
| | | h CIs | >100,000 |
| | | h CIr | >50,000 |
| | | h uKK | >50,000 |
| 2.12 | 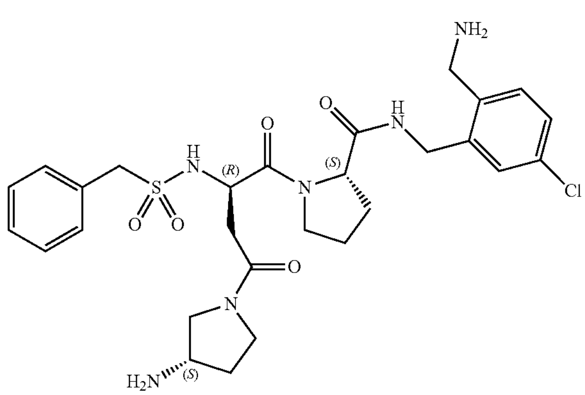 | h FIIa | 2.9 |
| | | h FXa | 14 |
| | | h aPC | >25,000 |
| | | h plasmin | >25,000 |
| | | h PK | 1,690 |
| | | h t-PA | >100,000 |
| | | h u-PA | >50,000 |
| | | h CIs | >30,000 |
| | | h CIr | >100,000 |
| | | h uKK | >20,000 |

TABLE 7-continued

Dissociation constants (K$_i$) of the exemplary compounds towards thrombin, factor Xa and key reference proteases.

| Compound | Structure | Enzyme assayed | K$_i$ (nm) |
|---|---|---|---|
| 2.13 | 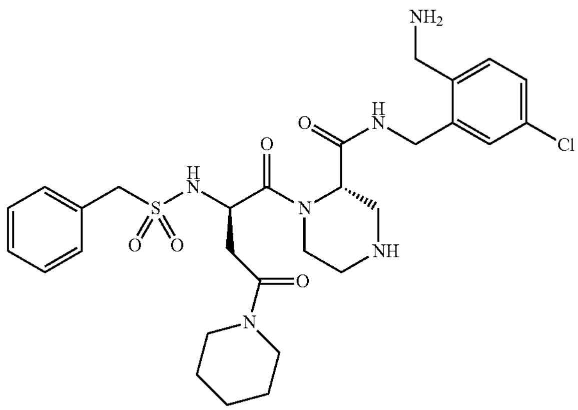 [SMILES: NCc1ccc(Cl)cc1CNC(=O)[C@@H]1CNCCN1C(=O)[C@@H](CC(=O)N1CCCCC1)NS(=O)(=O)Cc1ccccc1] | h FIIa<br>h FXa<br>h aPC<br>h plasmin<br>h PK<br>h t-PA<br>h u-PA<br>h Cls<br>h Clr<br>h uKK | 5.1<br>1.4<br>>30,000<br>>100,000<br>8,560<br>>40,000<br>>100,000<br>>60,000<br>>30,000<br>>20,000 |
| 2.14 | 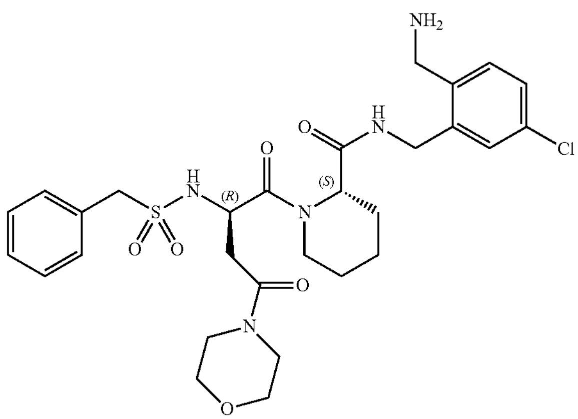 | h FIIa<br>h FXa<br>h aPC<br>h plasmin<br>h PK<br>h t-PA<br>h u-PA<br>h Cls<br>h Clr<br>h uKK | 0.3<br>8.3<br>>20,000<br>>50,000<br>4,530<br>>50,000<br>>50,000<br>>50,000<br>>50,000<br>>20,000 |
| 2.15 | 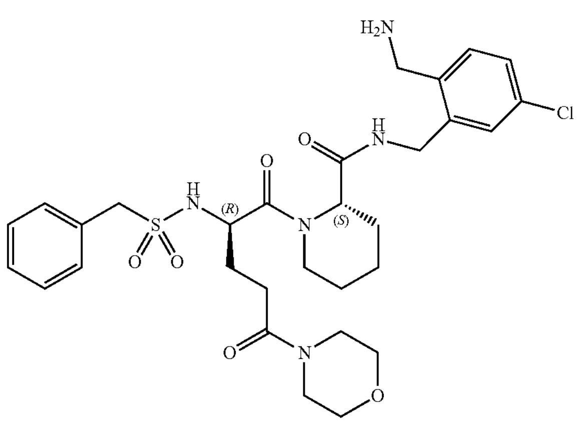 | h FIIa<br>h FXa<br>h aPC<br>h plasmin<br>h PK<br>h t-PA<br>h u-PA<br>h Cls<br>h Clr<br>h uKK | 0.7<br>9.4<br>>10,000<br>>5,000<br>7,200<br>>10,000<br>>50,000<br>>50,000<br>>20,000<br>>10,000 |

TABLE 7-continued

Dissociation constants ($K_i$) of the exemplary compounds towards thrombin, factor Xa and key reference proteases.

| Compound | Structure | Enzyme assayed | $K_i$ (nm) |
|---|---|---|---|
| 2.16 | 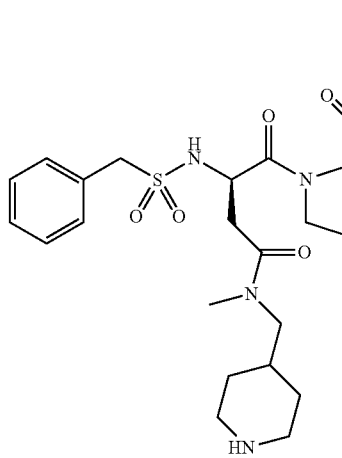 | h FIIa<br>h FXa<br>h aPC<br>h plasmin<br>h PK<br>h t-PA<br>h u-PA<br>h Cls<br>h Clr<br>h uKK | 0.30<br>1.5<br>>100,000<br>>5,000<br>417<br>>50,000<br>>100,000<br>>50,000<br>>10,000<br>>50,000 |
| 2.17 | 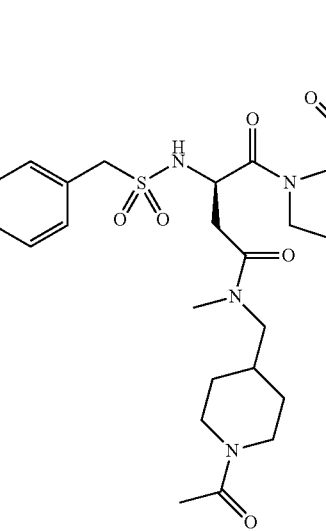 | h FIIa<br>h FXa<br>h aPC<br>h plasmin<br>h PK<br>h t-PA<br>h u-PA<br>h Cls<br>h Clr<br>h uKK | 0.2<br>3.7<br>>40,000<br>>5,000<br>417<br>>100,000<br>>40,000<br>>100,000<br>>10,000<br>>20,000 |
| 2.18 | 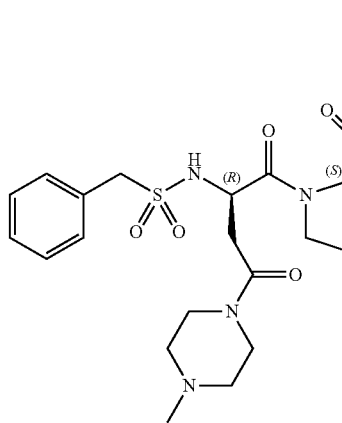 | h FIIa<br>h FXa<br>h aPC<br>h plasmin<br>h PK<br>h t-PA<br>h u-PA<br>h Cls<br>h Clr<br>h uKK | 1.5<br>7.9<br>>100,000<br>>10,000<br>170<br>>50,000<br>>100,000<br>>50,000<br>>25,000<br>>20,000 |

TABLE 7-continued

Dissociation constants (K$_i$) of the exemplary compounds towards thrombin, factor Xa and key reference proteases.

| Compound | Structure | Enzyme assayed | K$_i$ (nm) |
|---|---|---|---|
| 2.19 | 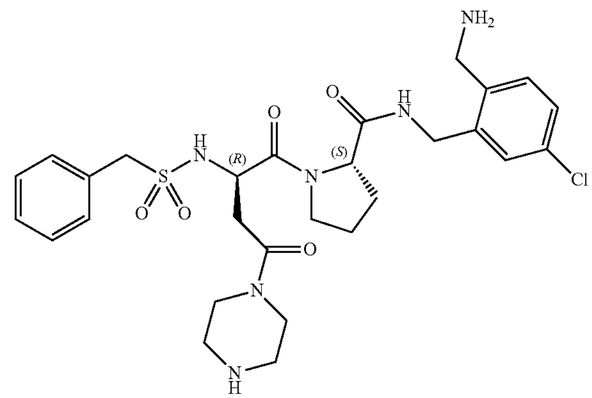 | h FIIa<br>h FXa<br>h aPC<br>h plasmin<br>h PK<br>h t-PA<br>h u-PA<br>h Cls<br>h Clr<br>h uKK | 2.4<br>1.5<br>>30,000<br>>4,600<br>1,024<br>>5,000<br>>15,000<br>>100,000<br>>50,000<br>>5,000 |
| 2.20 | 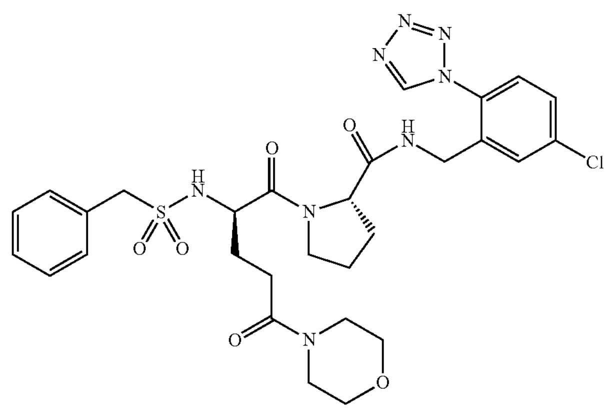 [SMILES: O=C(NCc1cc(Cl)ccc1-n1cnnn1)[C@@H]1CCCN1C(=O)[C@@H](CCC(=O)N1CCOCC1)NS(=O)(=O)Cc1ccccc1] | h FIIa<br>h FXa<br>h aPC<br>h plasmin<br>h PK<br>h t-PA<br>h u-PA<br>h Cls<br>h Clr<br>h uKK | 3.1<br>3.8<br>>30,000<br>7,270<br>740<br>>15,000<br>>100,000<br>>75,000<br>>30,000<br>>50,000 |
| 2.21 | 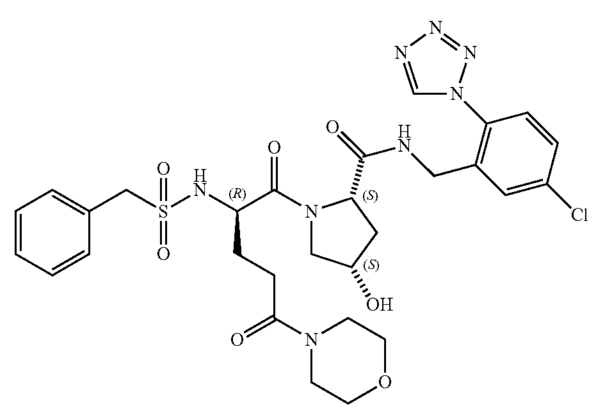 | h FIIa<br>h FXa<br>h aPC<br>h plasmin<br>h PK<br>h t-PA<br>h u-PA<br>h Cls<br>h Clr<br>h uKK | 159<br>5.3<br>>50,000<br>10,800<br>1,200<br>>20,000<br>>100,000<br>>50,000<br>>100,000<br>>100,000 |

TABLE 7-continued

Dissociation constants (K_i) of the exemplary compounds towards thrombin, factor Xa and key reference proteases.

| Compound | Structure | Enzyme assayed | $K_i$ (nm) |
|---|---|---|---|
| 2.22 | 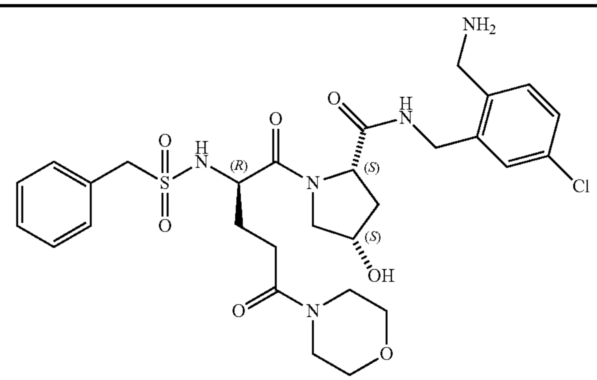 | h FIIa | 85 |
| | | h FXa | 0.68 |
| | | h aPC | >25,000 |
| | | h plasmin | >100,000 |
| | | h PK | 2,690 |
| | | h t-PA | >100,000 |
| | | h u-PA | >100,000 |
| | | h Cls | >50,000 |
| | | h Clr | >100,000 |
| | | h uKK | >100,000 |
| 2.23 | 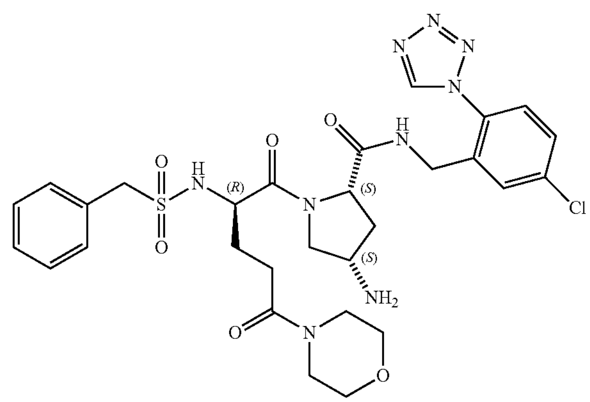 | h FIIa | 6.7 |
| | | h FXa | 0.32 |
| | | h aPC | 6,700 |
| | | h plasmin | 1,990 |
| | | h PK | 390 |
| | | h t-PA | 4,800 |
| | | h u-PA | >100,000 |
| | | h Cls | >70,000 |
| | | h Clr | >40,000 |
| | | h uKK | >50,000 |
| 2.24 | 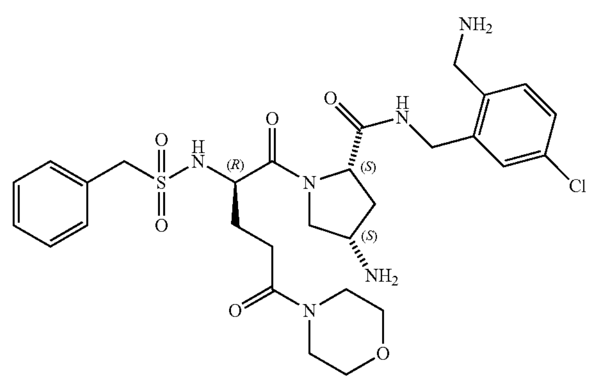 | h FIIa | 1.28 |
| | | h FXa | 0.19 |
| | | h aPC | >200,000 |
| | | h plasmin | >15,000 |
| | | h PK | 1,207 |
| | | h t-PA | >15,000 |
| | | h u-PA | >100,000 |
| | | h Cls | >60,000 |
| | | h Clr | >50,000 |
| | | h uKK | >50,000 |
| 2.25 | 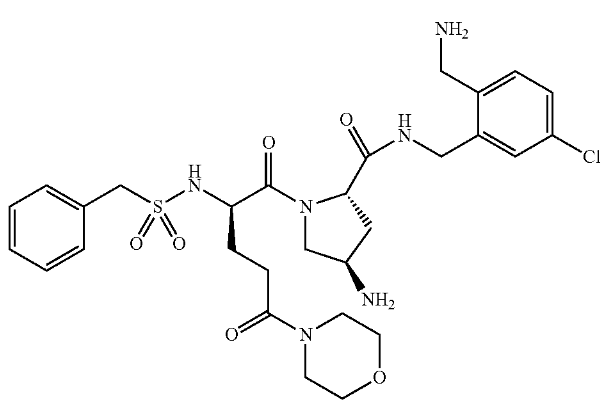 [SMILES: NCc1ccc(Cl)cc1CNC(=O)[C@@H]1C[C@@H](N)CN1C(=O)[C@@H](CCC(=O)N1CCOCC1)NS(=O)(=O)Cc1ccccc1] | h FIIa | 4.7 |
| | | h FXa | 1.1 |
| | | h aPC | >100,000 |
| | | h plasmin | >10,000 |
| | | h PK | 2,584 |
| | | h t-PA | >50,000 |
| | | h u-PA | >30,000 |
| | | h Cls | >100,000 |
| | | h Clr | >20,000 |
| | | h uKK | >50,000 |

TABLE 7-continued

Dissociation constants (K$_i$) of the exemplary compounds towards thrombin, factor Xa and key reference proteases.

| Compound | Structure | Enzyme assayed | K$_i$ (nm) |
|---|---|---|---|
| 2.26 | 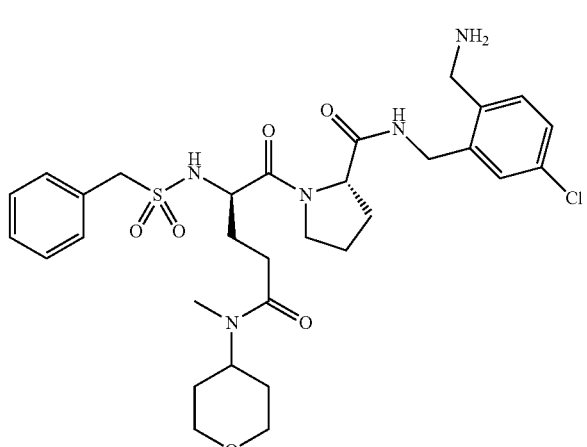 | h FIIa<br>h FXa<br>h aPC<br>h plasmin<br>h PK<br>h t-PA<br>h u-PA<br>h Cls<br>h Clr<br>h uKK | 1.0<br>6.9<br>>50,000<br>>30,000<br>2,550<br>>100,000<br>>100,000<br>>10,000<br>>100,000<br>>50,000 |
| 2.27 | 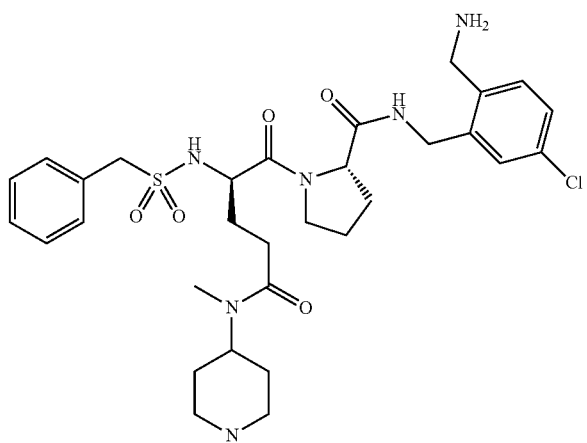 [SMILES: CN(C(=O)CC[C@@H](NS(=O)(=O)Cc1ccccc1)C(=O)N1CCC[C@H]1C(=O)NCc1cc(Cl)ccc1CN)C1CCOCC1] | h FIIa<br>h FXa<br>h aPC<br>h plasmin<br>h PK<br>h t-PA<br>h u-PA<br>h Cls<br>h Clr<br>h uKK | 0.8<br>18<br>>50,000<br>>10,000<br>1,650<br>>100,000<br>>100,000<br>>100,000<br>>100,000<br>>100,000 |
| 2.28 | 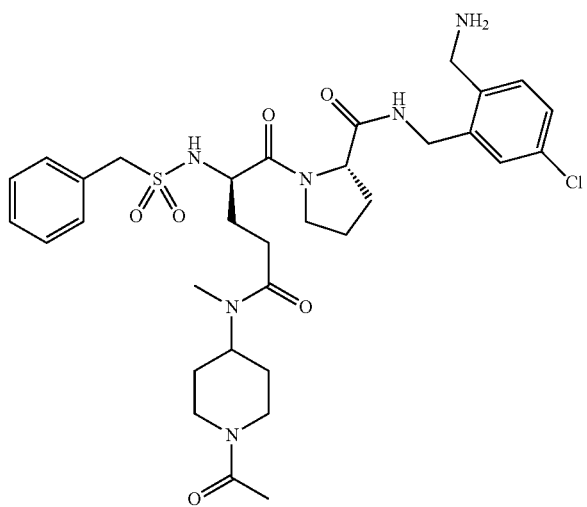 [SMILES: CC(=O)N1CCC(N(C)C(=O)CC[C@@H](NS(=O)(=O)Cc2ccccc2)C(=O)N2CCC[C@H]2C(=O)NCc2cc(Cl)ccc2CN)CC1] | h FIIa<br>h FXa<br>h aPC<br>h plasmin<br>h PK<br>h t-PA<br>h u-PA<br>h Cls<br>h Clr<br>h uKK | 0.57<br>36<br>>50,000<br>5,565<br>5,000<br>>100,000<br>>20,000<br>>20,000<br>>100,000<br>>100,000 |

TABLE 7-continued

Dissociation constants ($K_i$) of the exemplary compounds towards thrombin, factor Xa and key reference proteases.

| Compound | Structure | Enzyme assayed | $K_i$ (nm) |
|---|---|---|---|
| 2.29 | 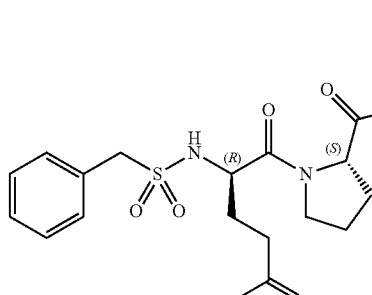 | h FIIa<br>h FXa<br>h aPC<br>h plasmin<br>h PK<br>h t-PA<br>h u-PA<br>h Cls<br>h Clr<br>h uKK | 3.3<br>93<br>>25,000<br>>15,000<br>>20,000<br>>20,000<br>>100,000<br>>50,000<br>>10,000 |
| 2.30 | 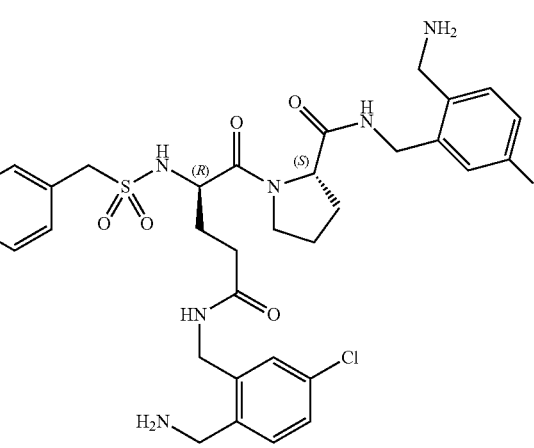 | h FIIa<br>h FXa<br>h aPC<br>h plasmin<br>h PK<br>h t-PA<br>h u-PA<br>h Cls<br>h Clr<br>h uKK | 0.99<br>8.6<br>>25,000<br>>5,000<br>432<br>>20,000<br>>40,000<br>>80,000<br>>30,000<br>>20,000 |
| 2.31 | 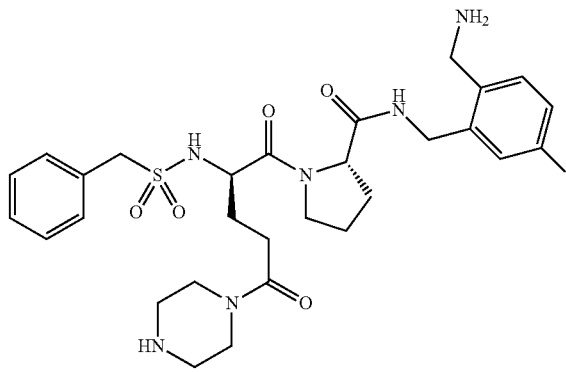 | h FIIa<br>h FXa<br>h aPC<br>h plasmin<br>h PK<br>h t-PA<br>h u-PA<br>h Cls<br>h Clr<br>h uKK | 0.48<br>21<br>>100,000<br>>10,000<br>4,000<br>>20,000<br>>100,000<br>>100,000<br>>100,000<br>>100,000 |
| 2.32 | 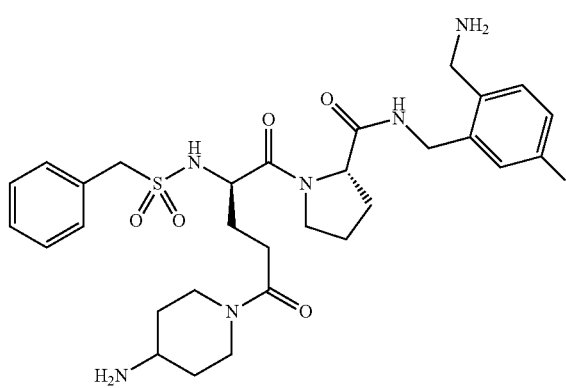 | h FIIa<br>h FXa<br>h aPC<br>h plasmin<br>h PK<br>h t-PA<br>h u-PA<br>h Cls<br>h Clr<br>h uKK | 0.15<br>33<br>>100,000<br>>20,000<br>3,060<br>>50,000<br>>100,000<br>>100,000<br>>100,000<br>>10,000 |

TABLE 7-continued

Dissociation constants (K$_i$) of the exemplary compounds towards thrombin, factor Xa and key reference proteases.

| Compound | Structure | Enzyme assayed | K$_i$ (nm) |
|---|---|---|---|
| 2.33 | 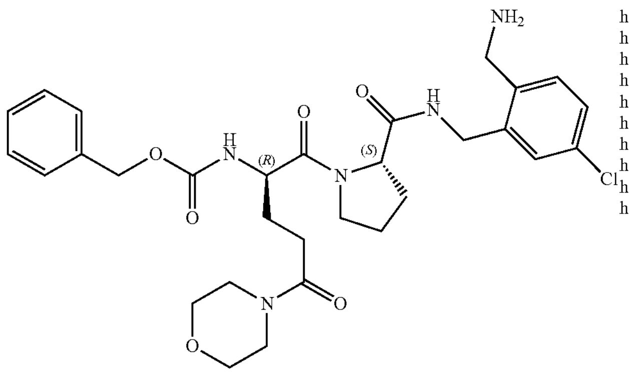 | h FIIa<br>h FXa<br>h aPC<br>h plasmin<br>h PK<br>h t-PA<br>h u-PA<br>h Cls<br>h Clr<br>h uKK | 1.4<br>8.8<br>>30,000<br>>20,000<br>6,061<br>>20,000<br>>50,000<br>>50,000<br>>100,000<br>>40,000 |
| 2.34 | 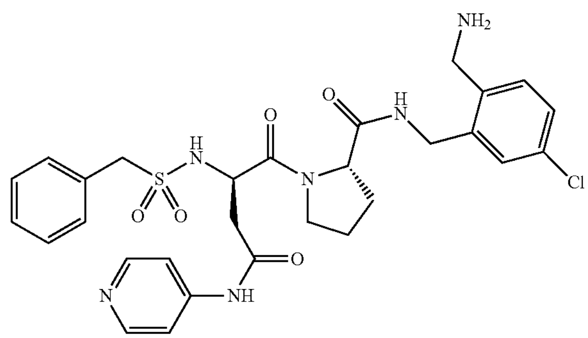 [SMILES: NCc1ccc(Cl)cc1CNC(=O)[C@@H]1CCCN1C(=O)[C@@H](CC(=O)Nc1ccncc1)NS(=O)(=O)Cc1ccccc1] | h FIIa<br>h FXa<br>h aPC<br>h plasmin<br>h PK<br>h t-PA<br>h u-PA<br>h Cls<br>h Clr<br>h uKK | 1.7<br>21<br>>100,000<br>>20,000<br>1,760<br>>100,000<br>>100,000<br>>100,000<br>>100,000<br>>100,000 |
| 2.35 | 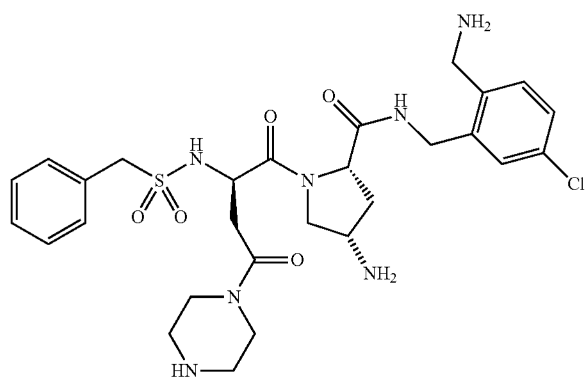 [SMILES: NCc1ccc(Cl)cc1CNC(=O)[C@@H]1C[C@H](N)CN1C(=O)[C@@H](CC(=O)N1CCNCC1)NS(=O)(=O)Cc1ccccc1] | h FIIa<br>h FXa<br>h aPC<br>h plasmin<br>h PK<br>h t-PA<br>h u-PA<br>h Cls<br>h Clr<br>h uKK | 4.4<br>0.79<br>>100,000<br>>3,000<br>351<br>1,000<br>>20,000<br>>15,000<br>>100,000<br>>50,000 |
| 2.36 | 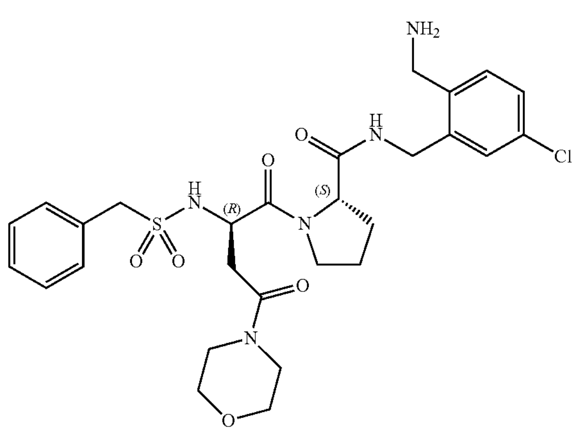 | h FIIa<br>h FXa<br>h aPC<br>h plasmin<br>h PK<br>h t-PA<br>h u-PA<br>h Cls<br>h Clr<br>h uKK | 0.34<br>0.38<br>>100,000<br>>12,000<br>565<br>18,000<br>>40,000<br>>100,000<br>>30,000 |

TABLE 7-continued

Dissociation constants ($K_i$) of the exemplary compounds towards thrombin, factor Xa and key reference proteases.

| Compound | Structure | Enzyme assayed | $K_i$ (nm) |
|---|---|---|---|
| 2.37 | 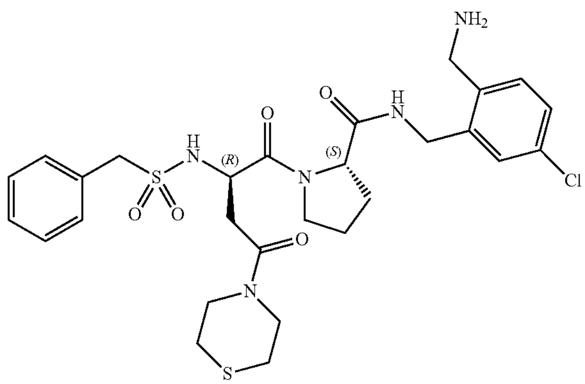 | h FIIa | 0.49 |
| | | h FXa | 0.54 |
| | | h aPC | >40,000 |
| | | h plasmin | 6,000 |
| | | h PK | 413 |
| | | h t-PA | 19,000 |
| | | h u-PA | >20,000 |
| | | h Cls | >80,000 |
| | | h Clr | >200,000 |
| | | h uKK | n.d. |
| 2.38 | 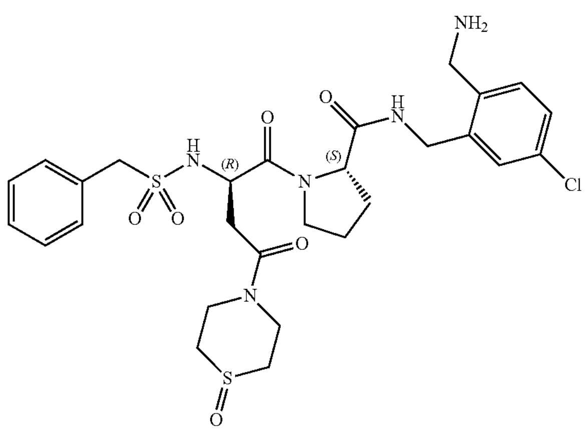 | h FIIa | 7.8 |
| | | h FXa | 5.5 |
| | | h aPC | >50,000 |
| | | h plasmin | 15,000 |
| | | h PK | 614 |
| | | h t-PA | >20,000 |
| | | h u-PA | >60,000 |
| | | h Cls | >80,000 |
| | | h Clr | >200,000 |
| | | h uKK | n.d. |
| 2.39 | 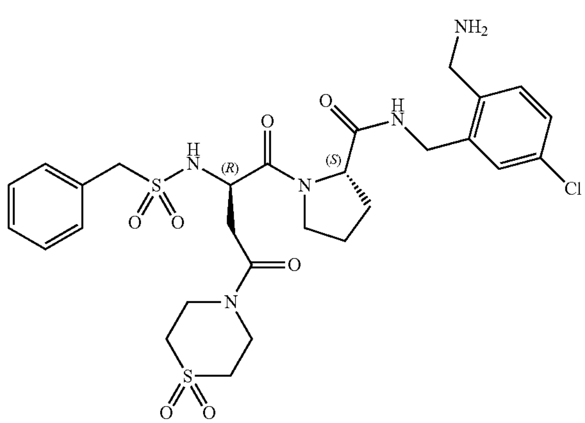 | h FIIa | 18.6 |
| | | h FXa | 15.4 |
| | | h aPC | >500 |
| | | h plasmin | n.d. |
| | | h PK | n.d. |
| | | h t-PA | n.d. |
| | | h u-PA | n.d. |
| | | h Cls | n.d. |
| | | h Clr | n.d. |
| | | h uKK | n.d. |

TABLE 7-continued

Dissociation constants ($K_i$) of the exemplary compounds towards thrombin, factor Xa and key reference proteases.

| Compound | Structure | Enzyme assayed | $K_i$ (nm) |
|---|---|---|---|
| 2.40 | 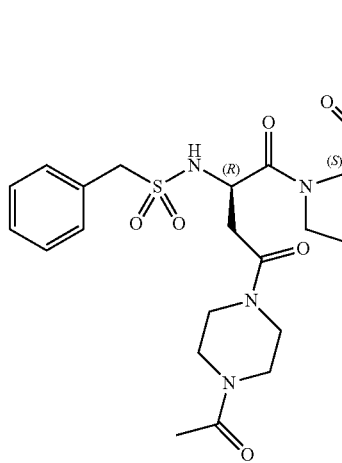 | h FIIa<br>h FXa<br>h aPC<br>h plasmin<br>h PK<br>h t-PA<br>h u-PA<br>h Cls<br>h Clr<br>h uKK | 6.3<br>2.4<br>>100,000<br>9,000<br>478<br>>20,000<br>>50,000<br>>80,000<br>>50,000<br>n.d. |
| 2.41 | 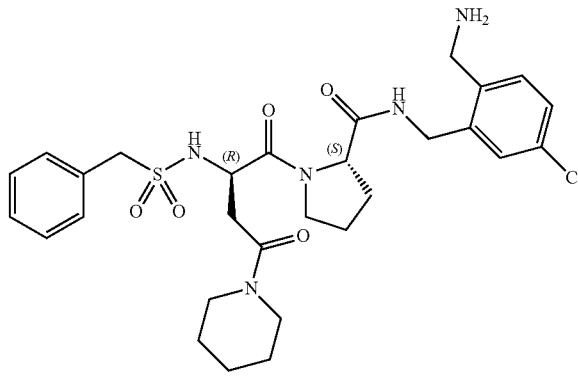 | h FIIa<br>h FXa<br>h aPC<br>h plasmin<br>h PK<br>h t-PA<br>h u-PA<br>h Cls<br>h Clr<br>h uKK | 0.11<br>0.12<br>>100,000<br>8,000<br>605<br>>15,000<br>>50,000<br>>80,000<br>>50,000<br>>40,000 |
| 2.42 | 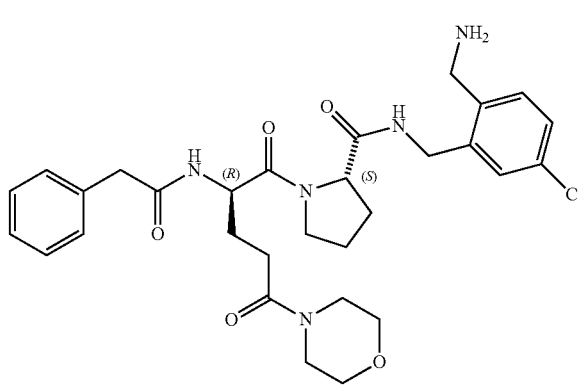 | h FIIa<br>h FXa<br>h aPC<br>h plasmin<br>h PK<br>h t-PA<br>h u-PA<br>h Cls<br>h Clr<br>h uKK | 88<br>965<br>>10,000<br>>50,000<br>>50,000<br>>50,000<br>>100,000<br>>100,000<br>>20,000<br>>20,000 |

TABLE 7-continued

Dissociation constants ($K_i$) of the exemplary compounds towards thrombin, factor Xa and key reference proteases.

| Compound | Structure | Enzyme assayed | $K_i$ (nm) |
|---|---|---|---|
| 2.43 | 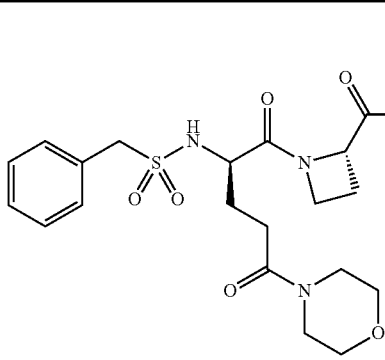 | h FIIa<br>h FXa<br>h aPC<br>h plasmin<br>h PK<br>h t-PA<br>h u-PA<br>h Cls<br>h Clr<br>h uKK | 9.7<br>1.7<br>>100,000<br>>40,000<br>5,807<br>>80,000<br>>20,000<br>>80,000<br>>30,000<br>>10,000 |
| 2.44 | 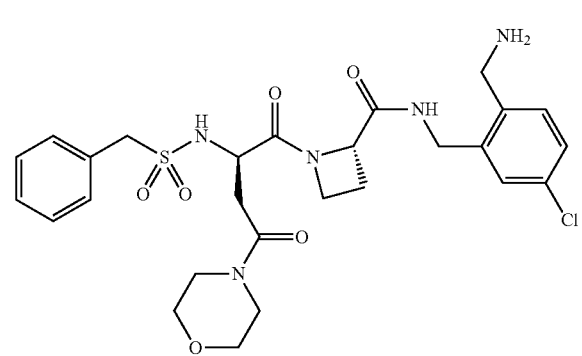 [SMILES: NCc1ccc(Cl)cc1CNC(=O)[C@@H]1CCN1C(=O)[C@@H](CC(=O)N1CCOCC1)NS(=O)(=O)Cc1ccccc1] | h FIIa<br>h FXa<br>h aPC<br>h plasmin<br>h PK<br>h t-PA<br>h u-PA<br>h Cls<br>h Clr<br>h uKK | 4.0<br>0.87<br>>100,000<br>>10,000<br>1,830<br>>35,000<br>>50,000<br>>100,000<br>>100,000<br>>20,000 |
| 2.45 | 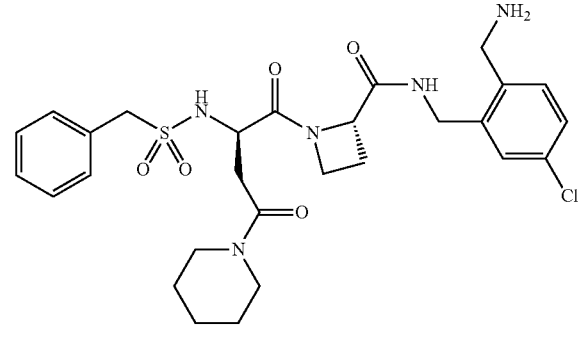 [SMILES: NCc1ccc(Cl)cc1CNC(=O)[C@@H]1CCN1C(=O)[C@@H](CC(=O)N1CCCCC1)NS(=O)(=O)Cc1ccccc1] | h FIIa<br>h FXa<br>h aPC<br>h plasmin<br>h PK<br>h t-PA<br>h u-PA<br>h Cls<br>h Clr<br>h uKK | 0.72<br>0.22<br>>100,000<br>>20,000<br>1,860<br>>20,000<br>>20,000<br>>100,000<br>>30,000<br>>10,000 |
| 2.46 | 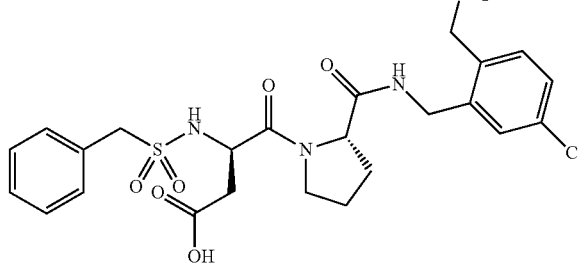 | h FIIa<br>h FXa<br>h aPC<br>h plasmin<br>h PK<br>h t-PA<br>h u-PA<br>h Cls<br>h Clr<br>h uKK | 12.2<br>1,324<br>>40,000<br>>10,000<br>>50,000<br>>50,000<br>>50,000<br>>50,000<br>>100,000<br>>20,000 |

TABLE 7-continued

Dissociation constants (K$_i$) of the exemplary compounds towards thrombin, factor Xa and key reference proteases.

| Compound | Structure | Enzyme assayed | K$_i$ (nm) |
|---|---|---|---|
| 2.47 | 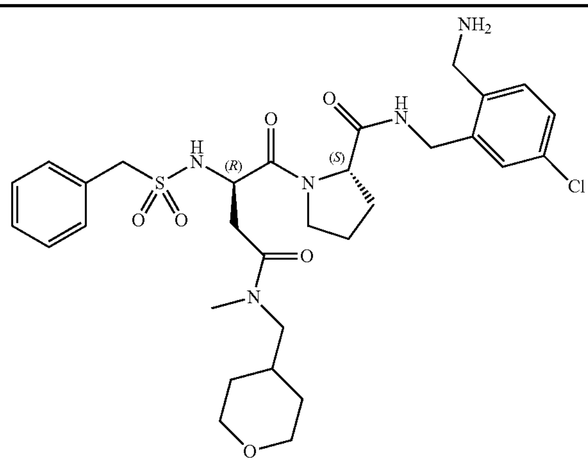 | h FIIa<br>h FXa<br>h aPC<br>h plasmin<br>h PK<br>h t-PA<br>h u-PA<br>h Cls<br>h Clr<br>h uKK | 0.32<br>2.0<br>>100,000<br>>15,000<br>304<br>>50,000<br>>100,000<br>>100,000<br>>10,000<br>>20,000 |
| 2.48 | 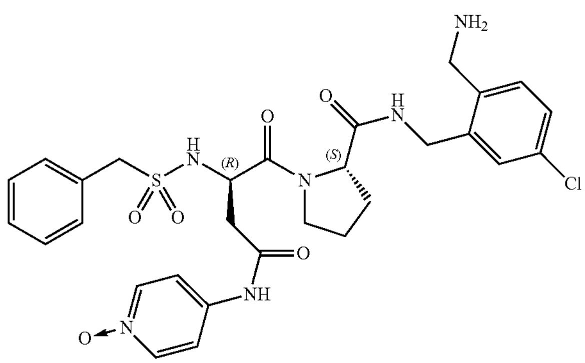 | h FIIa<br>h FXa<br>h aPC<br>h plasmin<br>h PK<br>h t-PA<br>h u-PA<br>h Cls<br>h Clr<br>h uKK | 2.5<br>17<br>>10,000<br>500<br>800<br>26,800<br>>100,000<br>>20,000<br>>100,000<br>>100,000 |
| 2.49 | 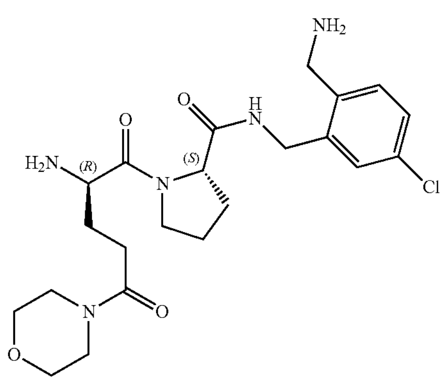 | h FIIa<br>h FXa<br>h aPC<br>h plasmin<br>h PK<br>h t-PA<br>h u-PA<br>h Cls<br>h Clr<br>h uKK | 8.0<br>134<br>>10,000<br>>100,000<br>>10,000<br>>100,000<br>>100,000<br>>100,000<br>>10,000<br>>100,000 |
| 2.50 | 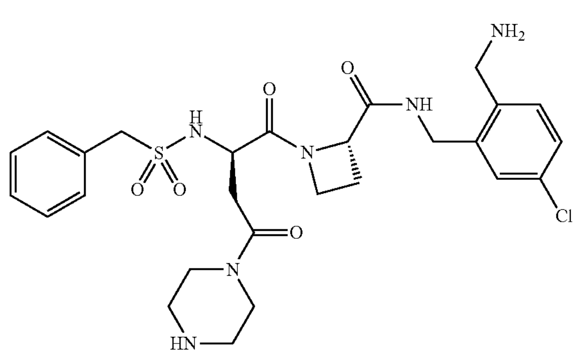 [SMILES: NCc1ccc(Cl)cc1CNC(=O)[C@@H]1CCN1C(=O)[C@@H](CC(=O)N1CCNCC1)NS(=O)(=O)Cc1ccccc1] | h FIIa<br>h FXa<br>h aPC<br>h plasmin<br>h PK<br>h t-PA<br>h u-PA<br>h Cls<br>h Clr<br>h uKK | 14<br>5.2<br>>100,000<br>>15,000<br>3,341<br>>20,000<br>>25,000<br>>100,000<br>>100,000<br>>100,000 |

The invention claimed is:

1. A compound having the following formula

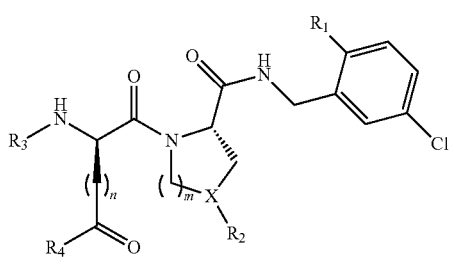

or a pharmaceutically acceptable salt thereof;
wherein:
n is an integer between 1 and 2 inclusively;
m is an integer between 0 and 2 inclusively;
X is selected from the group consisting of CH or N;
$R_1$ is selected from the group consisting of —$CH_2NH_2$, and

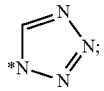

$R_2$ is selected from the group consisting of —H, —OH, —$NH_2$ and acetyl;
$R_3$ is selected from the group consisting of —H, benzyloxycarbonyl and benzylsulfonyl; and
$R_4$ is selected from the group consisting of —OH,

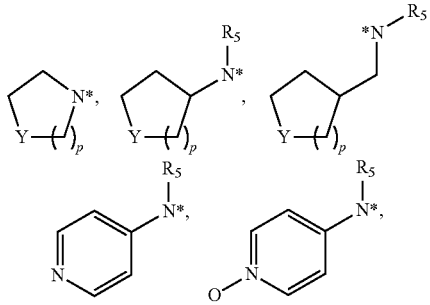

wherein p is an integer between 0 and 2 inclusively, Y is selected from the group consisting of —O—, —S—, —S(=O)—, —$SO_2$—, methylene, —CH(OH)—, —CH($NH_2$)—, —CH($CH_2$—OH)—, —CH($CH_2$—$NH_2$)— or —N($R_6$)—, $R_5$ is selected from the group consisting of —H or a simple ($C_1$-$C_3$) alkyl and $R_6$ is selected from the group consisting of —H; a simple ($C_1$-$C_3$) alkyl or a simple ($C_1$-$C_3$) acyl.

2. A compound according to claim 1, wherein $R_3$ is selected from the group consisting of benzyloxycarbonyl and benzylsulfonyl.

3. A compound according to claim 1, wherein $R_4$ is

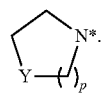

4. A compound according to claim 1, wherein $R_4$ is selected from the group of

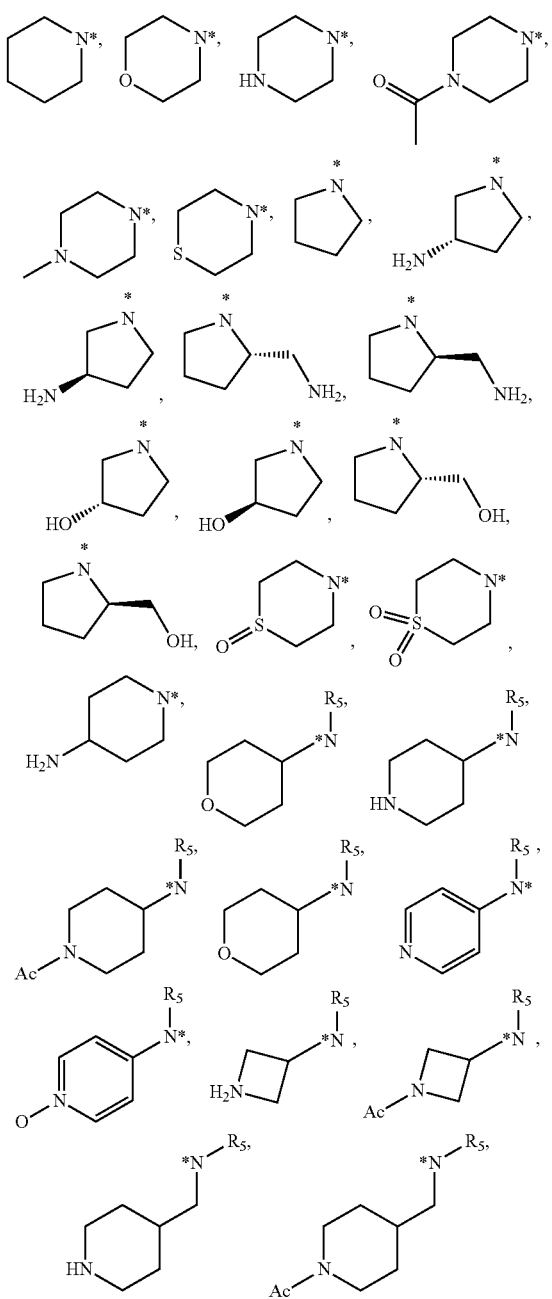

wherein $R_5$ is —H or methyl.

5. A compound according to claim 4, wherein R₄ is

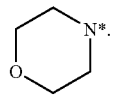

6. A compound according to claim 1, wherein n is 2.
7. A compound according to claim 1, wherein m is 1.
8. A compound according to claim 1, wherein X is CH, and R₂ is —H or —NH₂.
9. A compound according to claim 1, wherein R₁ is —CH₂NH₂.
10. A compound according to claim 1, wherein R₁ is —CH₂NH₂, n is 1 or 2 and R₄ is selected from the group of

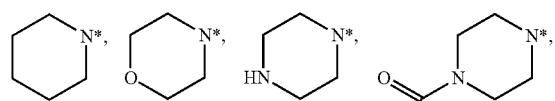

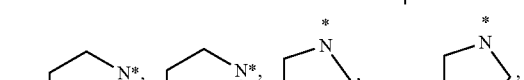

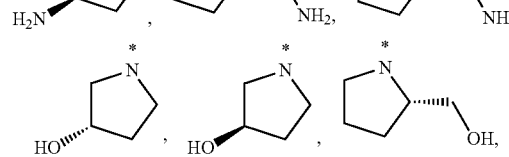

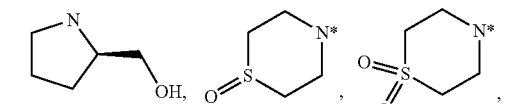

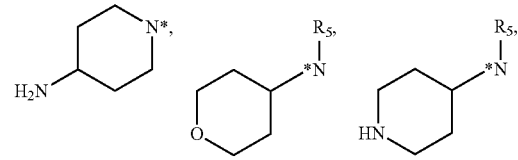

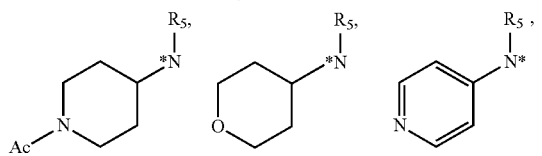

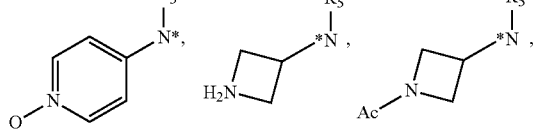

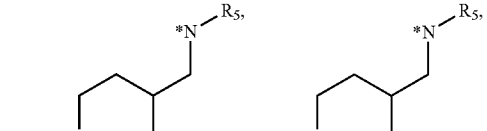

and R₅ is —H or methyl.

11. The compound of claim 1, selected from the group of

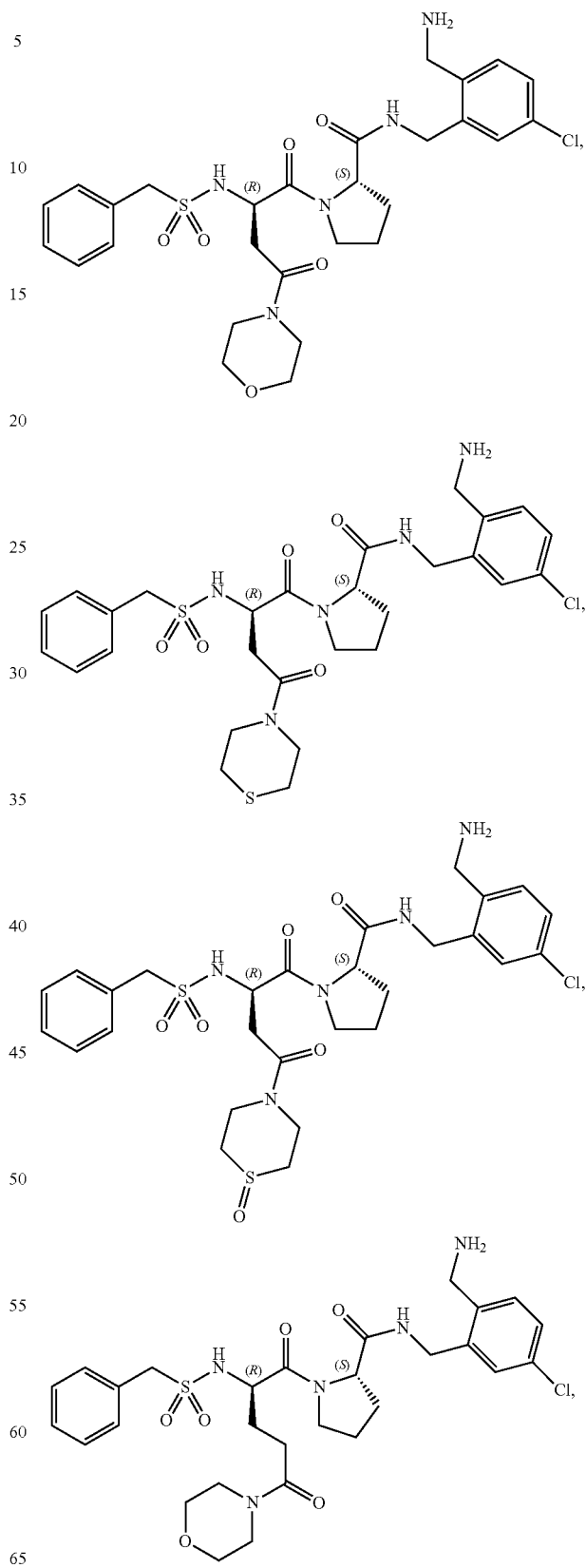

131
-continued
132
-continued
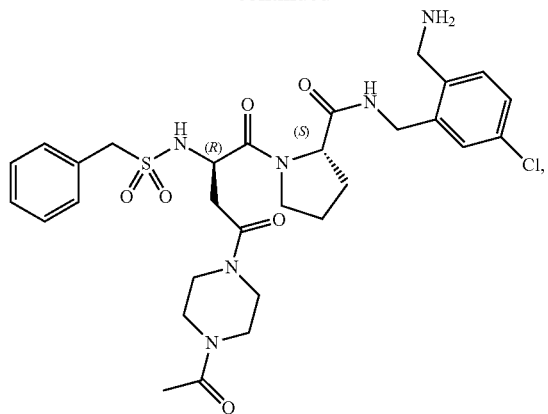
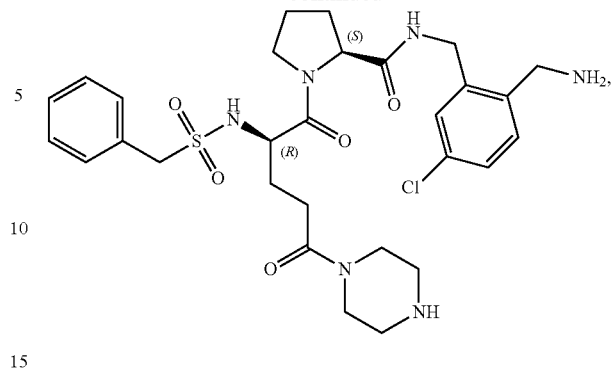
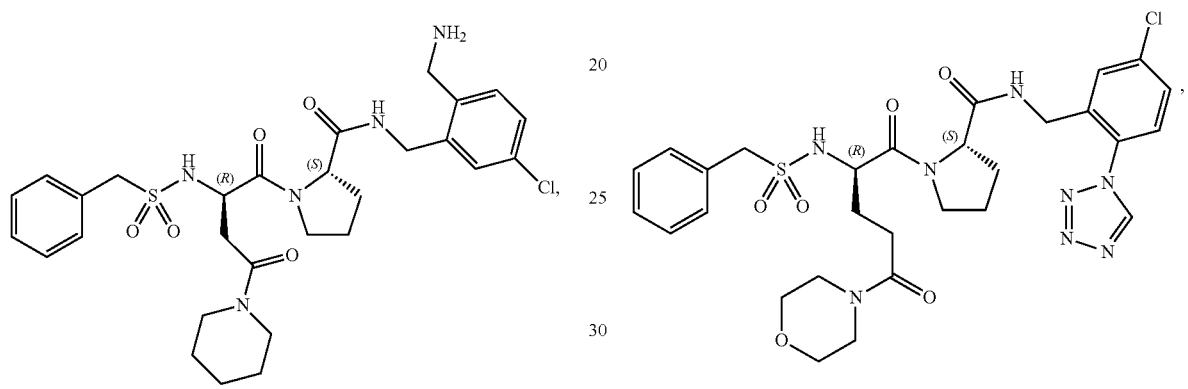
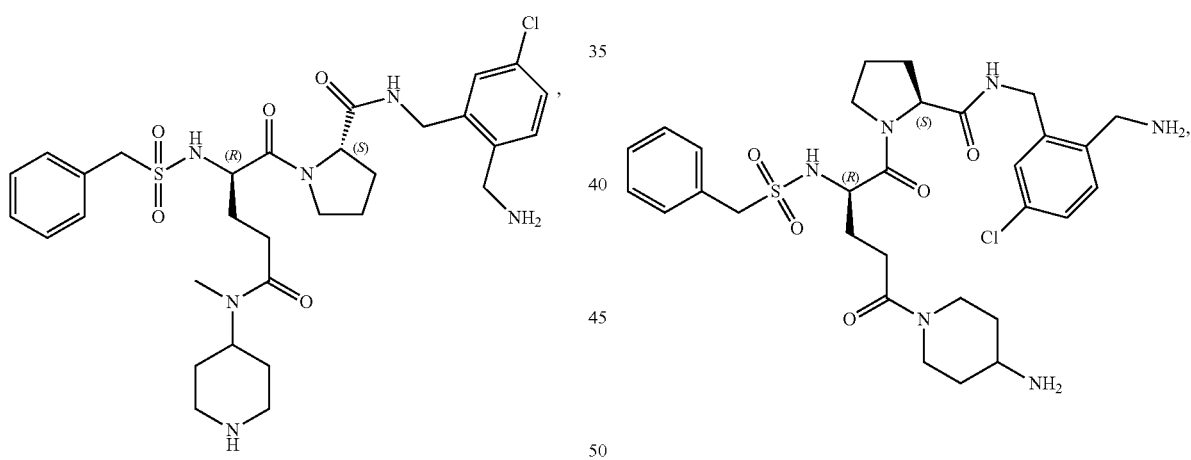
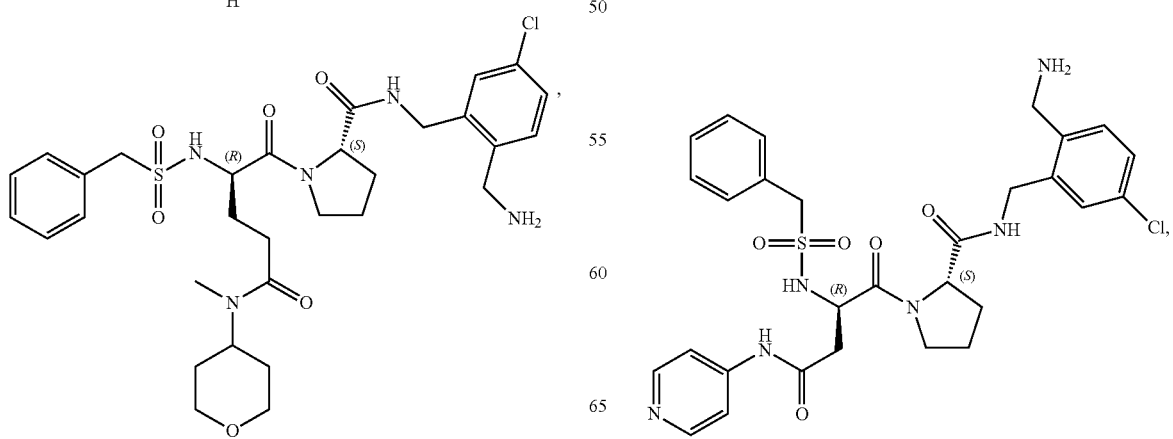

133
-continued
134
-continued
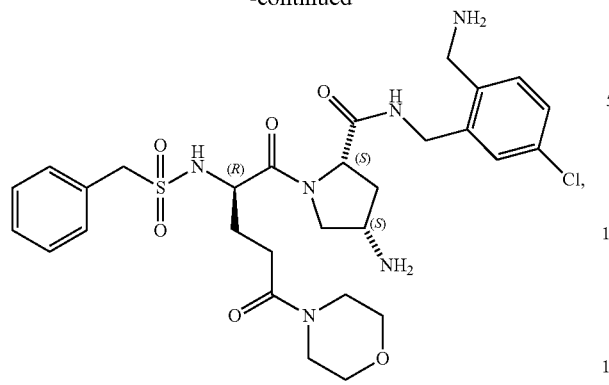
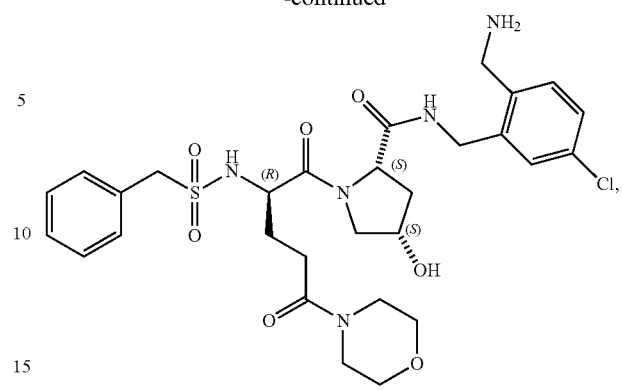
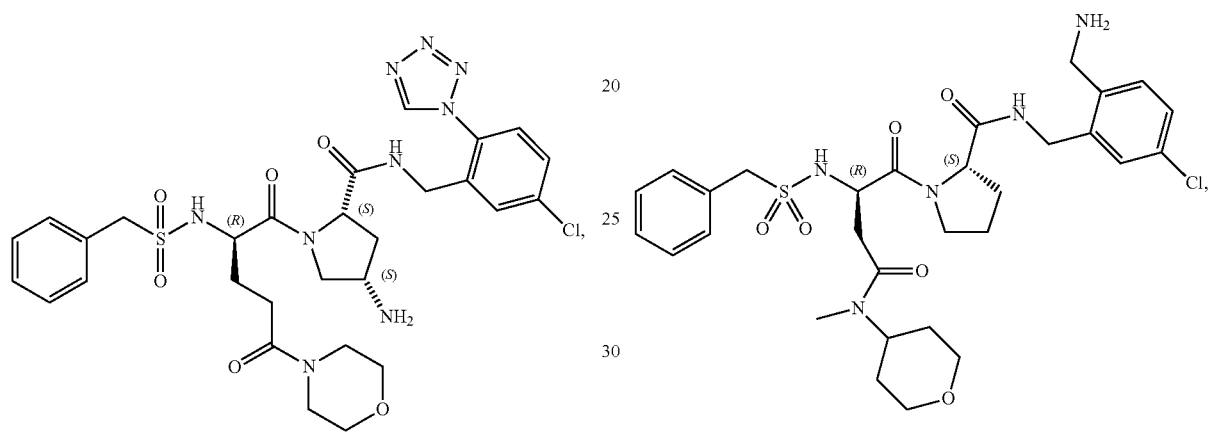
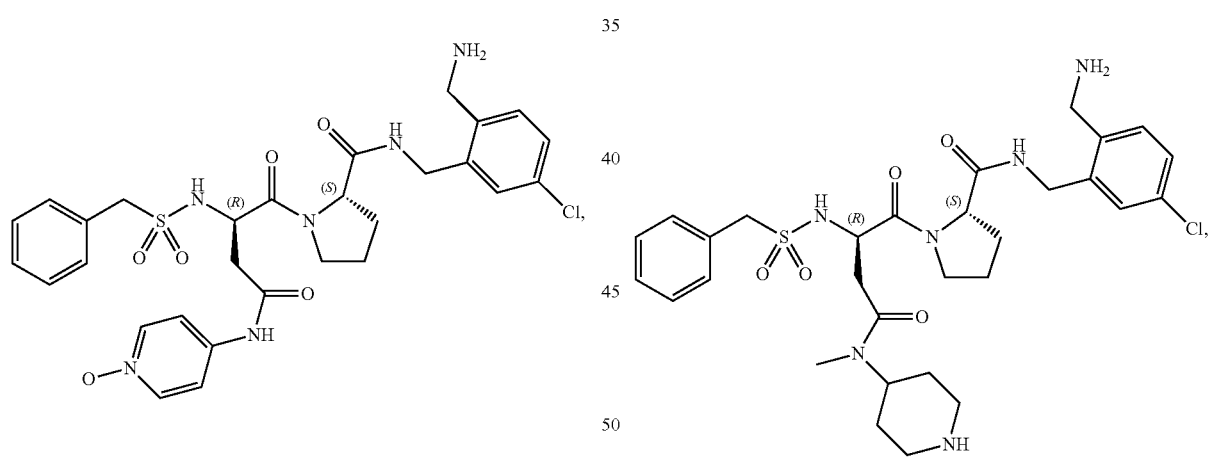
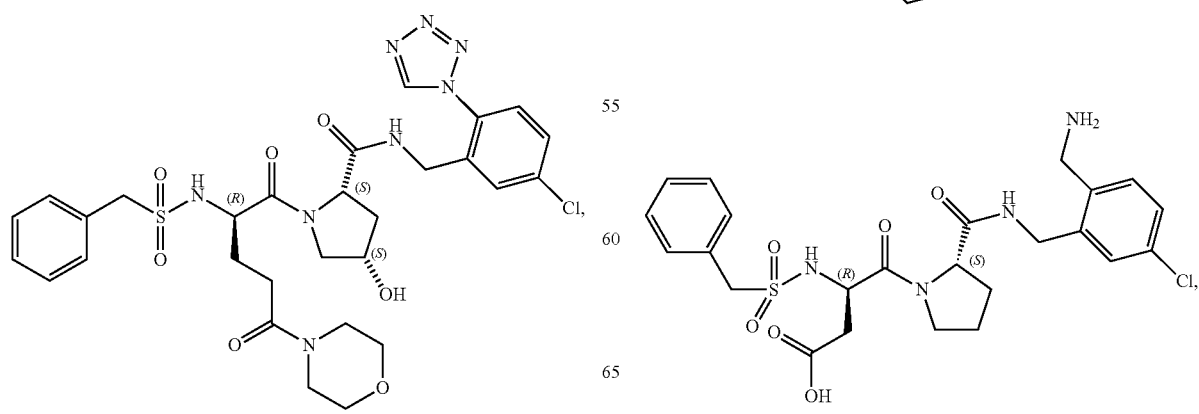

135
-continued
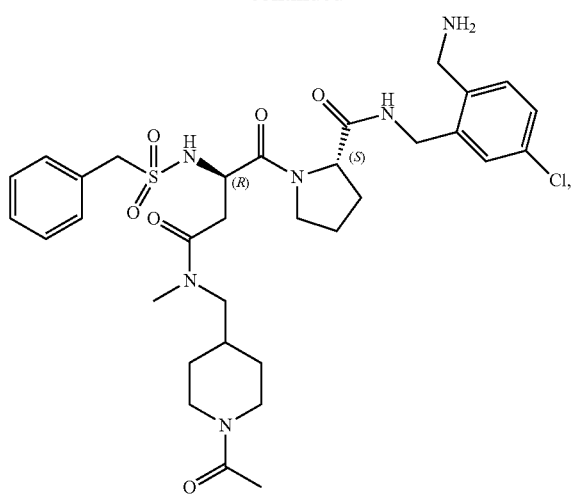
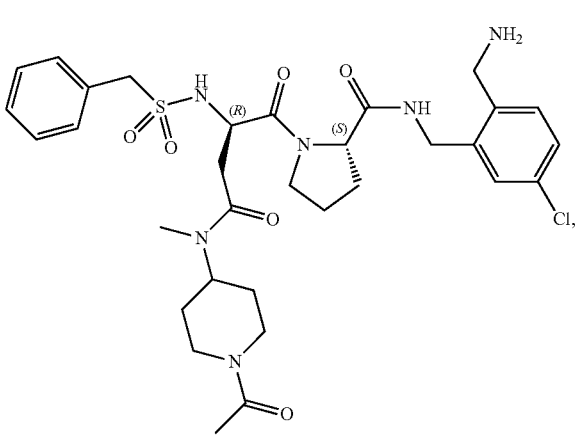
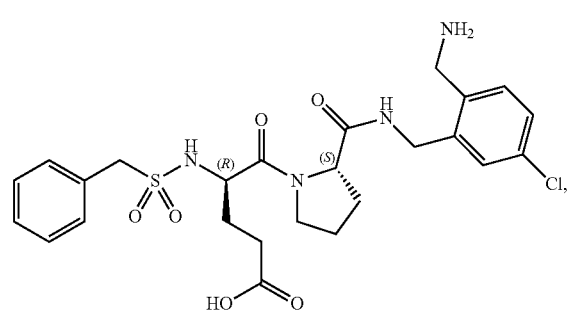
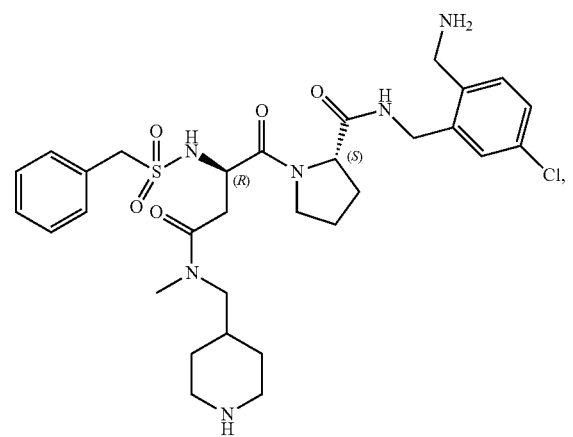
136
-continued
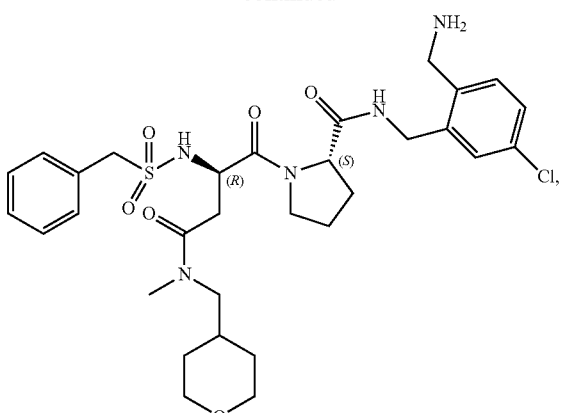
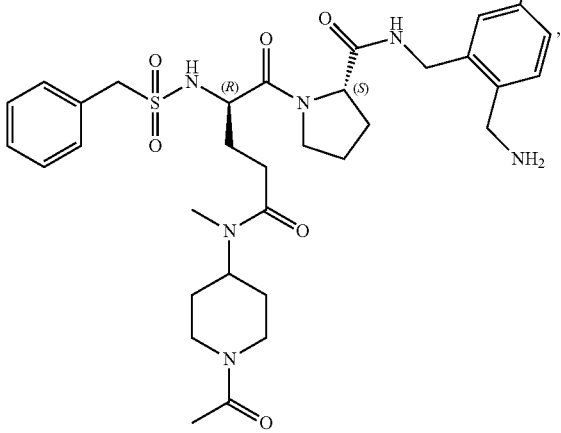
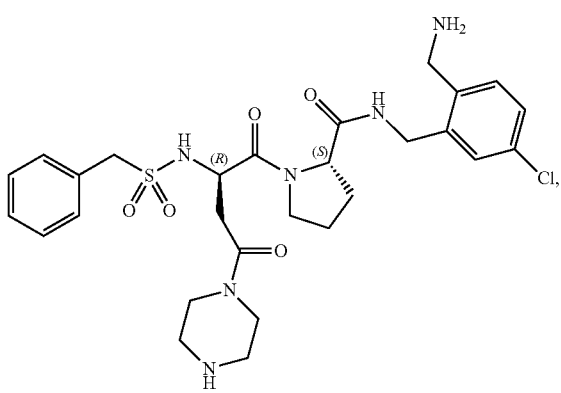
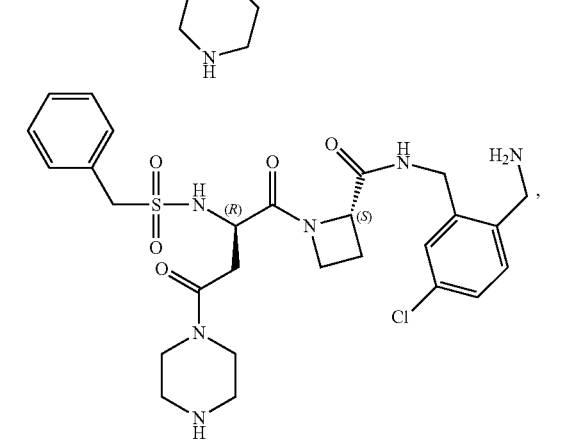

137
-continued
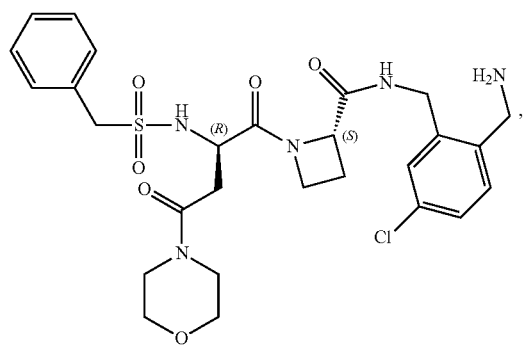
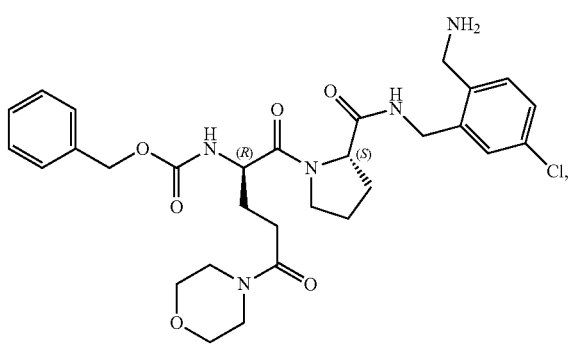
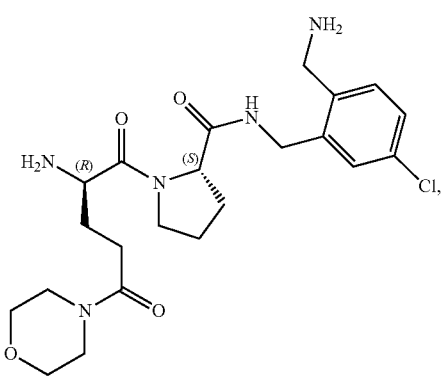
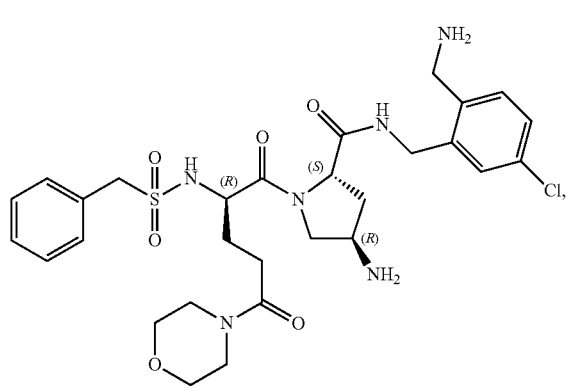
138
-continued
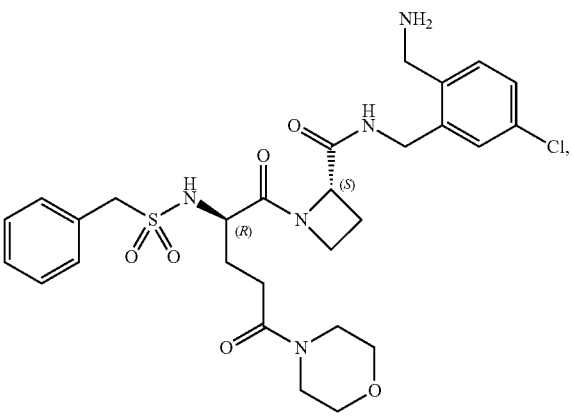
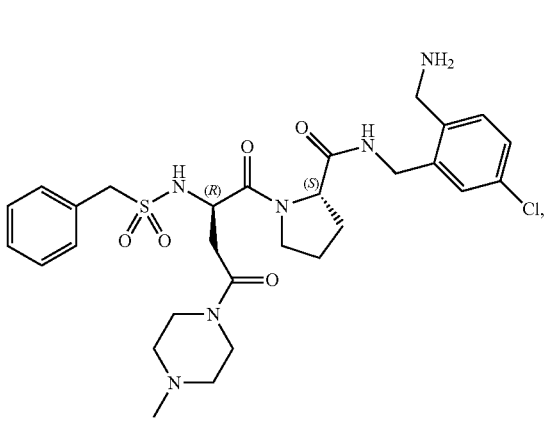
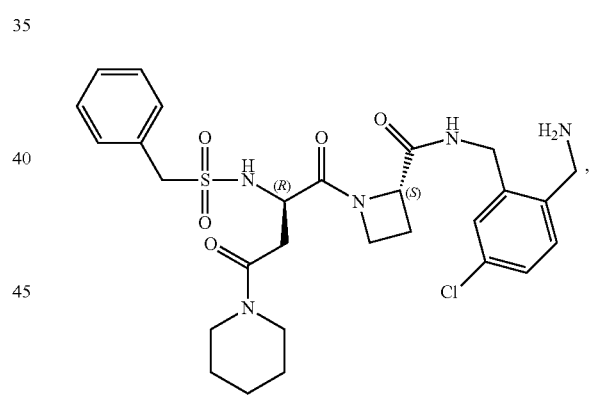
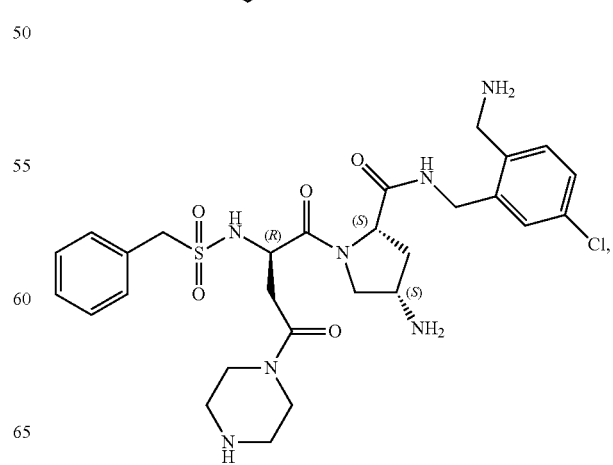

139
-continued
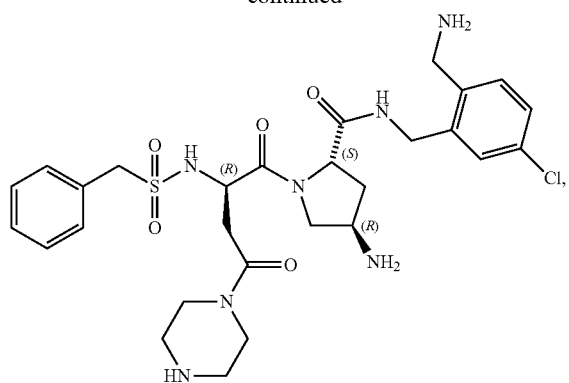
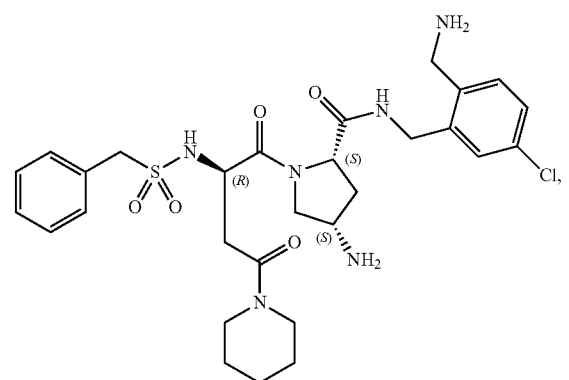
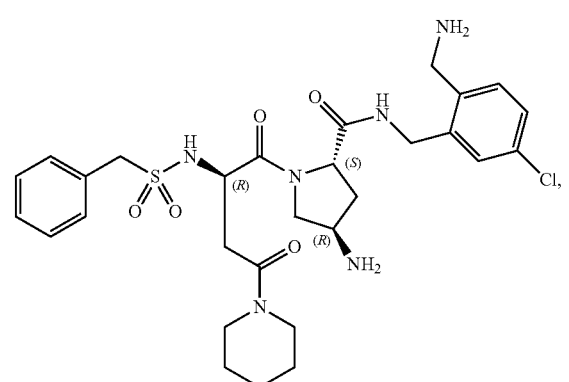
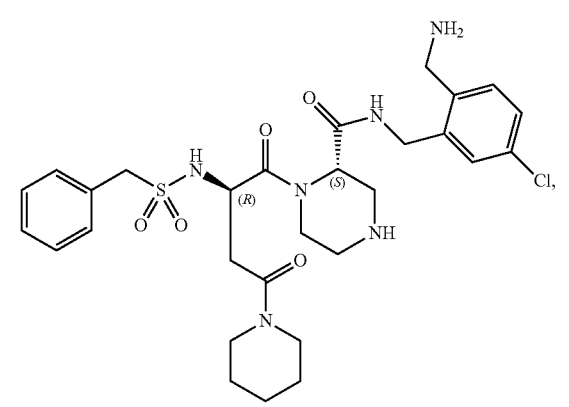
140
-continued
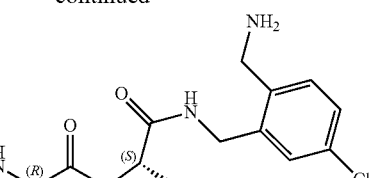
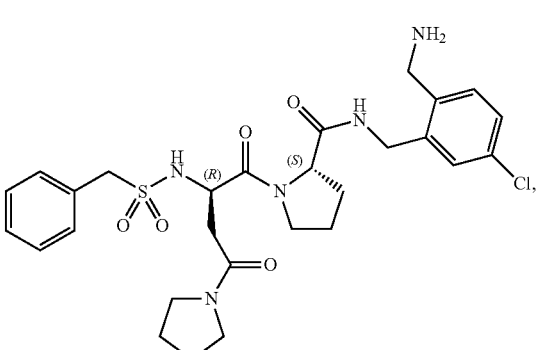
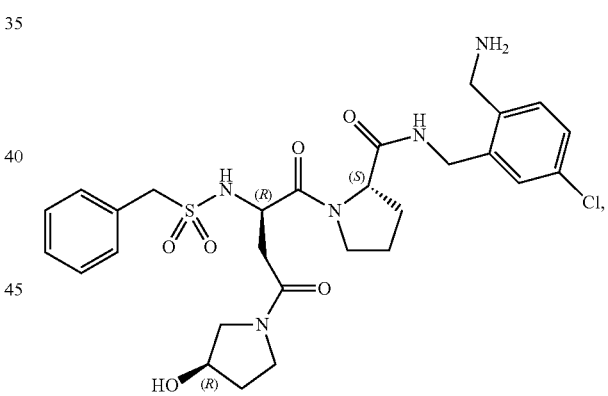
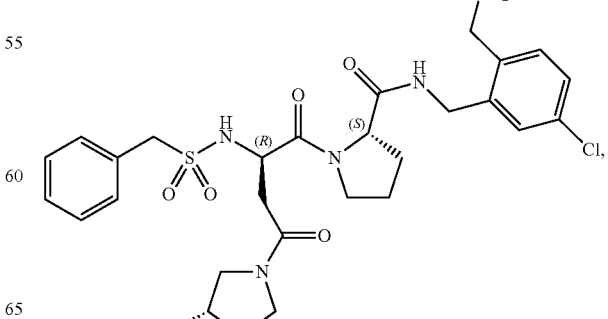

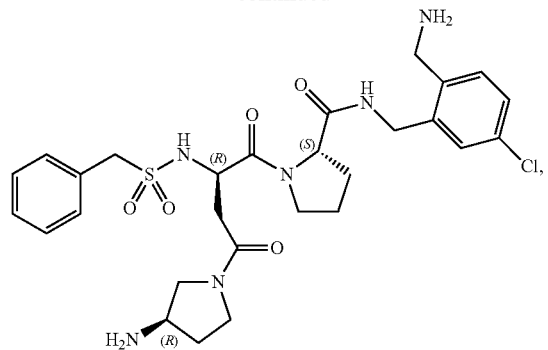
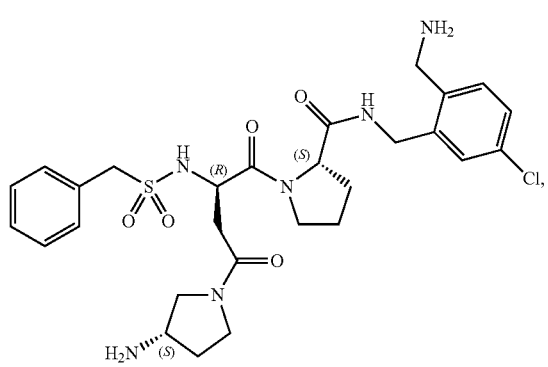
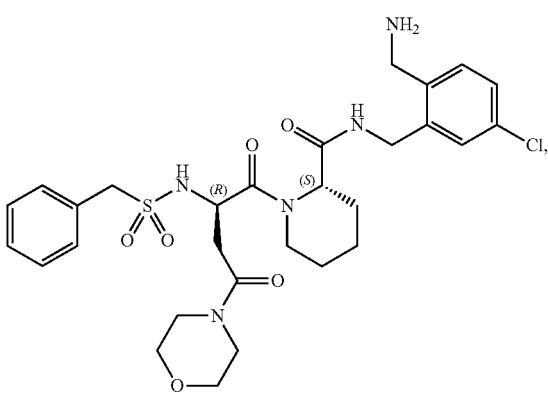
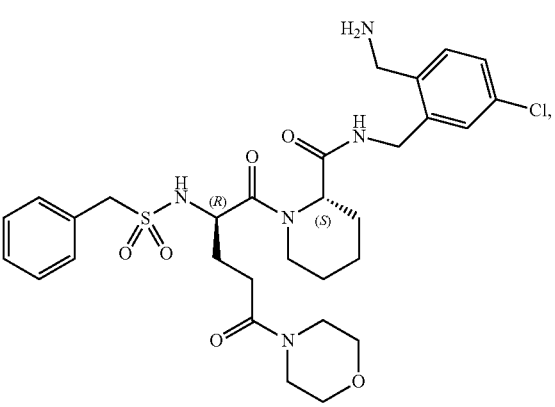
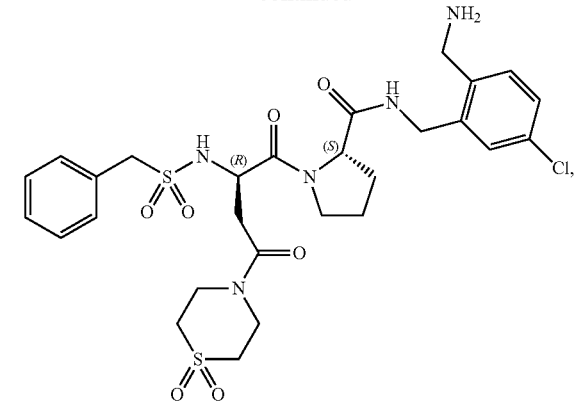
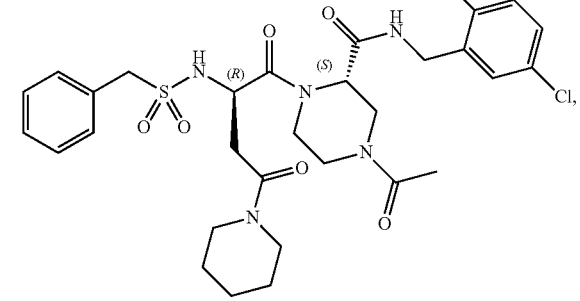
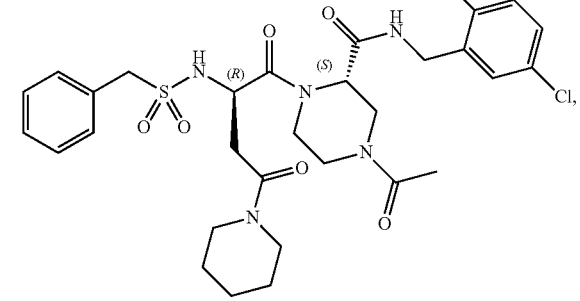
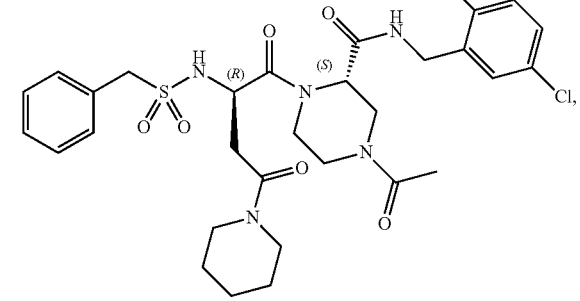
or a pharmaceutically acceptable salt thereof.
12. A pharmaceutical composition comprising one or more compounds according to claim 1, further comprising one or more pharmaceutically acceptable carriers or excipients.
* * * * *

UNITED STATES PATENT AND TRADEMARK OFFICE
CERTIFICATE OF CORRECTION

PATENT NO. : 8,497,245 B2
APPLICATION NO. : 13/332900
DATED : July 30, 2013
INVENTOR(S) : Peter Herold et al.

It is certified that error appears in the above-identified patent and that said Letters Patent is hereby corrected as shown below:

Title Page: Item 56, replace "WO 02/059065 8/2002" with --WO 2002/059065 /02002--.

In the Specification

Column 2, Line 63, replace "(Donneke" with --(Dönneke--.

Column 7, Line 67, replace "or methyl" with --or methyl.--.

Column 22, Line 27-28, replace "carboxyxlic" with --carboxylic--.

Column 31, Line 31, replace "compounds having the" with --compounds having the general formula F--.

Column 33, Line 15-16, replace "hemomstatic" with --hemostatic--.

Column 38, Line 23, replace "dried over over $Na_2SO_4$" with --dried over $Na_2SO_4$--.

Column 91, Table 6, in Compound 2.42, replace

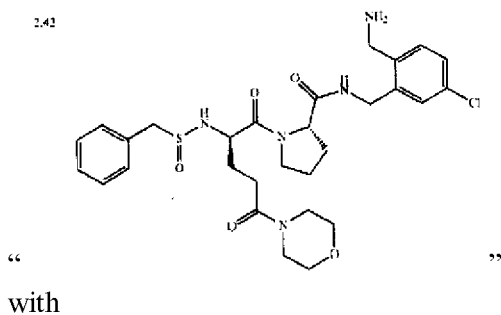

"with"

Signed and Sealed this
Sixteenth Day of June, 2015

Michelle K. Lee
*Director of the United States Patent and Trademark Office*

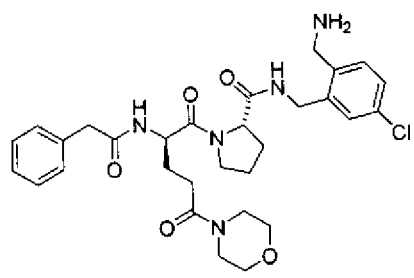
Column 96, Line 36, replace "potert" with --potent--.
Column 116, Table 7, in Compound 2.29, replace
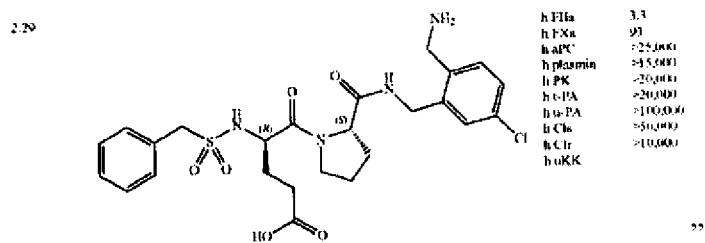
with
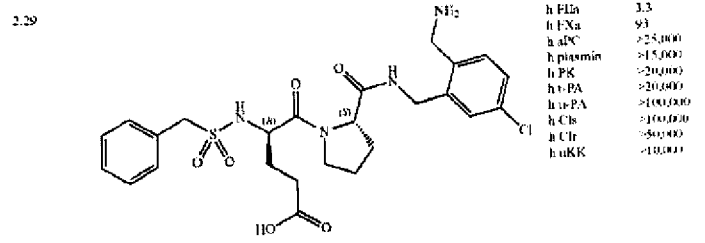
Column 118, Table 7, in Compound 2.36, replace
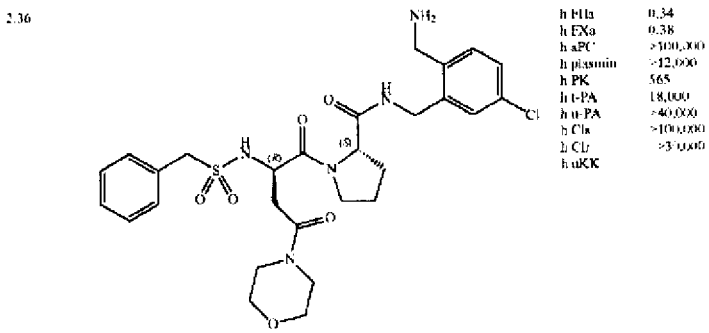
with

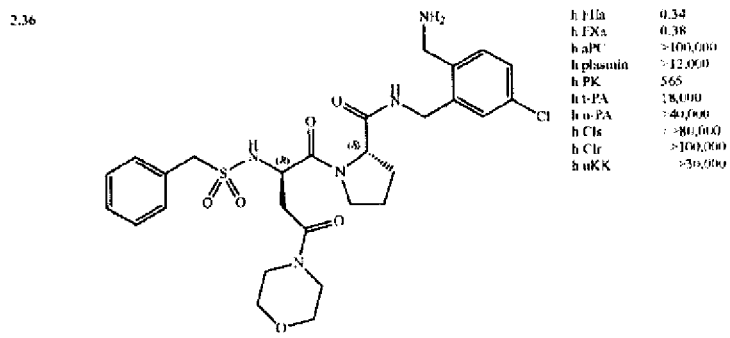
In the Claims
Column 127, Line 30, replace "the group consisting of CH or N" with --the group consisting of CH and N--.
Column 127, Line 66-67, replace "a simple ($C_1$-$C_3$) alkyl or a simple ($C_1$-$C_3$) acyl." with --a simple ($C_1$-$C_3$) alkyl and a simple ($C_1$-$C_3$) acyl.--.